United States Patent
Goto

(10) Patent No.: US 9,011,988 B2
(45) Date of Patent: *Apr. 21, 2015

(54) LIQUID-CRYSTAL COMPOUND, LIQUID-CRYSTAL COMPOSITION, LIGHT ABSORPTION ANISOTROPIC FILM, AND LIQUID-CRYSTAL DISPLAY DEVICE

(75) Inventor: Ryoji Goto, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 180 days.

This patent is subject to a terminal disclaimer.

(21) Appl. No.: 13/638,327

(22) PCT Filed: Mar. 28, 2011

(86) PCT No.: PCT/JP2011/057690
§ 371 (c)(1),
(2), (4) Date: Dec. 4, 2012

(87) PCT Pub. No.: WO2011/125620
PCT Pub. Date: Oct. 13, 2011

(65) Prior Publication Data
US 2013/0187090 A1 Jul. 25, 2013

(30) Foreign Application Priority Data
Mar. 31, 2010 (JP) ................. 2010-081026

(51) Int. Cl.
| | |
|---|---|
| C09K 19/60 | (2006.01) |
| C09K 19/16 | (2006.01) |
| C09K 19/20 | (2006.01) |
| C09K 19/22 | (2006.01) |
| C09K 19/24 | (2006.01) |
| G02B 5/30 | (2006.01) |
| C07C 43/215 | (2006.01) |
| G02F 1/1335 | (2006.01) |
| C09K 19/04 | (2006.01) |

(52) U.S. Cl.
CPC ......... *C09K 19/24* (2013.01); *C09K 2019/0448* (2013.01); *C07C 43/215* (2013.01); *C09K 2019/0496* (2013.01); *C09K 19/601* (2013.01); *G02F 1/133528* (2013.01)

(58) Field of Classification Search
USPC .................. 428/1.1, 1.31; 252/299.68, 299.1; 534/577, 649, 666, 670, 843
See application file for complete search history.

(56) References Cited

U.S. PATENT DOCUMENTS

| | | |
|---|---|---|
| 4,401,369 A | 8/1983 | Jones |
| 5,659,020 A | 8/1997 | Ogino et al. |
| 6,563,640 B1 | 5/2003 | Ignatov et al. |
| 8,728,976 B2 * | 5/2014 | Morishima .................. 503/227 |
| 2013/0070899 A1 * | 3/2013 | Morishima et al. ............. 378/71 |
| 2013/0083276 A1 * | 4/2013 | Iwahashi et al. ............... 349/117 |
| 2013/0107195 A1 * | 5/2013 | Morishima et al. ........... 349/194 |
| 2013/0120676 A1 * | 5/2013 | Iwahashi et al. ................ 349/15 |
| 2013/0169896 A1 * | 7/2013 | Iwahashi et al. ................ 349/15 |

FOREIGN PATENT DOCUMENTS

| | | |
|---|---|---|
| JP | 58-79077 | 5/1983 |
| JP | 60-215079 | 10/1985 |
| JP | 04-80726 | 3/1992 |
| JP | H09-132726 A | 5/1997 |
| JP | 2002-180052 | 6/2002 |
| JP | 2002-528758 | 9/2002 |
| JP | 2002-338838 | 11/2002 |

OTHER PUBLICATIONS

International Search Report issued on Jun. 28, 2011, by the Japanese Patent Office for International Appl. No. PCT/JP2011/057690.
Written Opinion issued on Jun. 28, 2011, by the Japanese Patent Office for International Appl. No. PCT/JP2011/057690.
John F. Dreyer, "Light Polarization from Films of Lyotropic Nematic Liquid Crystals", Journal de Physique, 1969, 4, 114.
H. Seki, "Japanese Journal of Applied Physics", vol. 24, No., 5, May 24, 1985, L299.
W.S.Park, "Effect of molecular structure of a dichroic dye and the ordering of a liquid crystal on the dichroism of the dye-liquid crystal binary mixtures", vol. 5, No. 5, 1989.
T.J. Nishizawa, "Highly Uniaxial Orientation in Oligo (p-phenylenevinylene) Films induced during Wet-Coating Process", J. Am. Chem. Soc., vol. 131, No. 7, 2009, 131, 2464.
Office Action issued in corresponding Japanese Patent Application No. 2010-081026 dated Nov. 19, 2013, with partial English Translation.

* cited by examiner

*Primary Examiner* — Shean C Wu
(74) *Attorney, Agent, or Firm* — Buchanan, Ingersoll & Rooney PC

(57) ABSTRACT

A liquid-crystal compound denoted by general formula (I) below wherein each of the groups is defined and Dye denotes an azo dye residue denoted by general formula (II) with X and n also being defined.

$$\text{Dye-L}^1 - \underset{R^2}{\underset{|}{\overset{R^1}{\overset{|}{\bigcirc}}}} - L^1\text{-Dye} \qquad (I)$$

$$X - \bigcirc - (N = N - Ar)_n - * \qquad (II)$$

The azo liquid-crystal compound is capable of orientation with a high degree of orientation order.

20 Claims, No Drawings

LIQUID-CRYSTAL COMPOUND, LIQUID-CRYSTAL COMPOSITION, LIGHT ABSORPTION ANISOTROPIC FILM, AND LIQUID-CRYSTAL DISPLAY DEVICE

TECHNICAL FIELD

The present invention relates to a liquid-crystal compound and composition that are useful in the manufacturing of various optical elements such as light absorption anisotropic films. The present invention further relates to a light absorption anisotropic film that is manufactured using the liquid-crystal compound and liquid-crystal composition, and to a liquid-crystal display device having this light absorption anisotropic film.

BACKGROUND ART

In cases where the attenuating function, polarizing function, scattering function, blocking function, and the like of irradiated light including laser beams and natural light are required, devices operating based on different principles have been conventionally allocated for each of these functions. As a result, products corresponding to these functions have been manufactured by different manufacturing processes for each of these functions.

For example, a linear polarizer, circular polarization plate, or the like is employed in a liquid-crystal element (LCD) to control optical rotation and birefringence in the display. A circular polarization plate is employed in an organic electroluminescent element (OLED) to prevent reflection of external light. Conventionally, iodine is widely employed in these polarizing plates (polarizing elements) as a dichroic substance. However, since iodine sublimates readily, it affords inadequate heat resistance and light resistance when employed in a polarizing element. The quenching color becomes deep blue, rendering the element less than ideal as a colorless polarizing element over the entire region of the visible spectrum.

Polarizing elements in which dichroic substances are employed as organic dyes have been investigated. However, these organic dyes present problems in that they yield only polarizing elements with a dichroic property that is considerably inferior to that of iodine. In particular, in LCDs in which the rotational or birefringent property of light is utilized as a display principle, the polarizing element is an important constituent component. In recent years, the development of new polarizing elements has progressed with the goal of enhancing display performance and the like.

One method of achieving this is, for example, in the same manner as in a polarizing element containing iodine, to dissolve or adsorb a dichroic organic dye (dichroic dye) in a polymer material such as a polyvinyl alcohol and stretch the film in one direction to orient the dichroic dye. However, this method presents problems in that processes such as stretching entail time and effort.

Accordingly, other methods have recently garnered attention. As such a method, in Nonpatent Reference 1, the intermolecular interaction of organic dye molecules on a substrate such as glass or a transparent film is utilized to orient the dichroic dye and form an anisotropic dye film such as a polarizing film. However, the method described in this reference is known to present a problem in terms of heat resistance.

Further, a wet film-forming method is employed to achieve the above orientation of the dichroic dye through the intermolecular interaction of organic dye molecules on a substrate such as glass or a transparent film. When manufacturing an anisotropic dye film by such a wet film-forming method, it is necessary to employ a dye that is suited to the process of wet film formation as well as to the high dichroism of the dye molecules as the dye employed in the dye film. Examples of wet film formation methods are methods of depositing and orienting the dye on a substrate and methods of controlling the orientation of the dye. Accordingly, many of the dyes that can be employed in polarizing elements obtained by the above conventional stretching process are unsuited to wet film forming methods. Patent References 1 to 3 propose materials that are suited to the process set forth above. However, even though suited to this process, these materials present a problem in that they are incapable of exhibiting a high degree of dichroism.

a) The fact that the angle formed between the moment of inertia and the transition moment is small, b) the fact that they have a high molecular aspect ratio, and the like are known means of obtaining highly dichroic dyes (Nonpatent References 2 and 3). Azo dyes, anthraquinone dyes, and the like are known to have dye skeletons that meet such characteristics. In particular, polyazo dyes having multiple azo groups in the long axis direction of the molecule are employed as skeletons manifesting desired and high light absorption coefficients. Symmetrical polyazo dyes with a single skeleton bonded through a single bond or linking group are an example of a means of conveniently synthesizing a polyazo dye with a high aspect ratio. A number of such dyes are described in Nonpatent Reference 4.

However, symmetrical polyazo dyes normally exhibit problems in the form of high crystallinity and poor solubility.

Additionally, Nonpatent Reference 5 describes a method of forming an anisotropic film having a high degree of order by coating an oligophenylene-vinylene compound of specific structure on an alignment film as a method of obtaining an anisotropic film using molecules other than dyes. However, when employed as a dye, this compound has a short wavelength and tends to fade when irradiated with light.

PRIOR ART REFERENCES

Patent References

[Patent Reference 1] Japanese Unexamined Patent Publication (KOKAI) No. 2002-180052
[Patent Reference 2] Published Japanese Translation (TOKUHYO) No. 2002-528758 of a PCT International Application
[Patent Reference 3] Japanese Unexamined Patent Publication (KOKAI) No. 2002-338838

Nonpatent References

[Nonpatent Reference 1] Dreyer, J. F., Journal de Physique, 1969, 4, 114.
[Nonpatent Reference 2] Seki, H., Jpn. J. Appl. Phys., 1985, 24, L299.
[Nonpatent Reference 3] Park, W. S., Liq. Cryst., 1989, 5, 1405.
[Nonpatent Reference 4] lvashchenko, A. V., Dichroic Dyes for Liquid Crystal Displays, 1994, CRC Press, Inc.
[Nonpatent Reference 5] Nishizawa, T., J. Am. Chem. Soc., 2009, 131, 2464.

SUMMARY OF THE INVENTION

Problem to be Solved by the Invention

An object of the present invention is to provide a novel azo liquid-crystal compound that is capable of orientation with a high degree of orientation order, has a good polarizing property, and functions as a dichroic dye, and a novel liquid-crystal composition that is useful in the manufacturing of light absorption anisotropic films.

A further object of the present invention is to provide a light absorption anisotropic film that is manufactured using the above liquid-crystal compound or liquid-crystal composition, and a liquid-crystal display device comprising this light absorption anisotropic film.

SUMMARY OF THE INVENTION

The method for solving the above-mentioned problem is as follows.

[1] The liquid-crystal compound denoted by general formula I) below:

[Chem. 1]

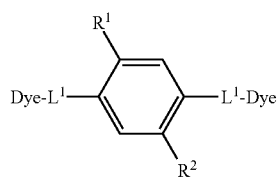

(I)

wherein each of $R^1$ and $R^2$ denotes a hydrogen atom, alkyl group, alkoxy group, or substituent denoted by -$L^2$-Y, with at least one of the two denoting a group other than a hydrogen atom; $L^2$ denotes an alkylene group in which one $CH_2$ group, or two or more nonadjacent $CH_2$ groups, are optionally substituted with —O—, —COO—, —OCO—, —OCOO—, —NRCOO—, —OCONR—, —CO—, —S—, —$SO_2$—, —NR—, —$NRSO_2$—, or —$SO_2NR$— (where R denotes a hydrogen atom or an alkyl group with 1 to 4 carbon atoms); Y denotes a hydrogen atom, hydroxy group, alkoxy group, carboxyl group, halogen atom, or polymerizable group; each instance of $L^1$ denotes a linking group selected from the group consisting of azo groups (—N═N—), carbonyloxy groups (—C(═O)O—), oxycarbonyl groups (—O—C(═O)—) imino groups (—N═CH—), and vinylene groups (—C═C—); and each instance of Dye denotes an azo dye residue denoted by general formula (II):

[Chem. 2]

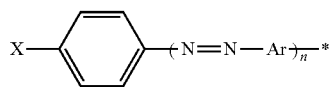

(II)

where in formula (II), * denotes a bond with $L^1$; X denotes a hydroxy group, a substituted or unsubstituted alkyl group, a substituted or unsubstituted alkoxy group, an unsubstituted amino group, or a mono or dialkylamine group; Ar denotes an optionally substituted aromatic hydrocarbon ring or optionally substituted aromatic hetero ring; and n denotes an integer of 1 to 3 such that when n is 2 or greater, the multiple instances of Ar may be identical or mutually different.

[2] The liquid-crystal compound according to [1], wherein in formula (I), $R^1$ denotes a hydrogen atom, an alkyl group with 1 to 10 carbon atoms, or an alkoxy group with 1 to 9 carbon atoms; $R^2$ denotes a substituent denoted by -$L^2$-Y, wherein $L^2$ denotes an alkylene group with 5 to 30 carbon atoms, in which one $CH_2$ group, or two or more nonadjacent $CH_2$ groups, are optionally substituted with —O—, —COO—, —OCO—, —OCOO—, —CO—, —S—, —$SO_2$—, —NR—, —$NRSO_2$—, or —$SO_2NR$— (where R denotes a hydrogen atom or an alkyl group with 1 to 4 carbon atoms); and Y denotes a hydrogen atom, hydroxy group, alkoxy group, carboxyl group, halogen atom, or polymerizable group.

[3] The liquid-crystal compound according to [1], wherein $L^1$ in general formula (I) is a vinylene group.

[4] The liquid-crystal compound according to [1], wherein $L^2$ in general formula (I) comprises a group denoted by —$(OCH_2CH_2)_p$— (where p denotes a number of 3 or greater).

[5] The liquid-crystal compound according to any one of [1] to [4], wherein Y in general formula (I) is a polymerizable group.

[6] A liquid-crystal composition comprising the liquid-crystal compound according to any one of [1] to [5].

[7] The liquid-crystal composition according to [6], further comprising one or more dichroic dyes.

[8] A film comprising the liquid-crystal composition according to [6] or [7].

[9] A light absorption anisotropic film comprising the liquid-crystal composition according to [6] or [7].

[10] The light absorption anisotropic film according to [9], wherein the light that is transmitted when a C light source is employed as the light source satisfies 0.28<x<0.36 and 0.28<y<0.36 in the xy chromaticity diagram.

[11] A liquid-crystal display device comprising the light absorption anisotropic film according to [9] or [10].

Effect of the Invention

The present invention provides a novel azo liquid-crystal compound that is capable of orientation with a high degree of orientation order, has a good polarizing property, and functions as a dichroic dye, and a novel liquid-crystal composition that is useful in the manufacturing of light absorption anisotropic films.

The present invention also provides a light absorption anisotropic film that is manufactured using the above liquid-crystal compound or liquid-crystal composition, and a liquid-crystal display device comprising this light absorption anisotropic film.

MODES OF CARRYING OUT THE INVENTION

The present invention will be described in detail below. In the present description, the word "to" is employed to mean that the preceding and succeeding numbers are included as lower and upper limits.

1. The Liquid-Crystal Compound of Formula (I)

The present invention relates to the liquid-crystal compound denoted by formula (I) below. In the liquid-crystal compound of formula (I), the polyazo skeleton constituting the long axis of the molecule is asymmetric. As a result, the crystallinity is lower than in conventional symmetric polyazo dyes. Generally, the lower the crystallinity of a compound, the lower the orientation order tends to be. However, research by the present inventors has revealed that by incorporating a substituent at a prescribed position on the benzene ring positioned at the center of the polyazo skeleton, almost no orientation order was lost despite lowering the crystallinity. That is, the compound denoted by formula (I) affords a high degree of order and can be employed as a dichroic dye. Further, because the crystallinity is lower than in a symmetric polyazo dye, it exhibits good solubility.

Among liquid-crystal compounds other than azo liquid-crystal compounds, such as oligophenylenevinylene liquid-crystal compounds, there are compounds that orient with a high degree of order. However, oligophenylenevinylene liquid-crystal compounds have short wavelengths when employed as dyes and afford inadequate color generation as dichroic dyes. They also present a problem in that they tend to fade in color when irradiated with light. The compound of formula (I) affords good light resistance and is useful as a material for optical elements such as polarizing films that are frequently exposed to light.

[Chem. 3]

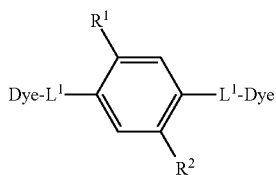

(I)

In the formula, each of $R^1$ and $R^2$ denotes a hydrogen atom, alkyl group, alkoxy group, or substituent denoted by -$L^2$-Y, with at least one of the two denoting a group other than a hydrogen atom. $L^2$ denotes an alkylene group in which one $CH_2$ group, or two or more nonadjacent $CH_2$ groups, are optionally substituted with —O—, —COO—, —OCO—, —OCOO—, —NRCOO—, —OCONR—, —CO—, —S—, —$SO_2$—, —NR—, —$NRSO_2$—, or —$SO_2NR$— (where R denotes a hydrogen atom or an alkyl group with 1 to 4 carbon atoms). Y denotes a hydrogen atom, hydroxy group, alkoxy group, carboxyl group, halogen atom, or polymerizable group.

Therein, it is desirable for one from among $R^1$ and $R^2$ to be a hydrogen atom or a short-chain substituent with about 1 to 4 carbon atoms, and the other from among $R^1$ and $R^2$ to be a long-chain substituent with about 5 to 30 carbon atoms so as to further enhance solubility. Generally, the molecular configuration, anisotropy of polarizability, and the like are known to greatly affect the expression of liquid crystallinity. This is described in detail in the Liquid Crystal Handbook (Maruzen (Ltd.), 2000). The typical skeleton of a rod-shaped liquid crystal molecule is comprised of a rigid mesogen and a terminal chain that is flexible in the long axis direction of the molecule. Generally, the lateral substituent groups in the short axis direction of the molecule, corresponding to $R^1$ and $R^2$ in formula (I), are either small substituents that do not impede rotation of the molecule, or are not substituted. As an example of imparting characteristics to lateral substituents, a hydrophilic (such as an ionic) lateral substituent can be incorporated. The case of a stabilized smectic phase is known, but the case of exhibiting a stable nematic phase is little known. In particular, the example of introducing a long-chain substituent at a specific substitution site on a rod-shaped crystalline molecule exhibiting a nematic phase to enhance solubility without lowering the degree of orientation order is completely unknown.

Examples of the alkyl group denoted by each of $R^1$ and $R^2$ are alkyl groups having 1 to 30 carbon atoms. As an example of the above short-chain alkyl group, 1 to 9 carbon atoms are desirable and 1 to 4 carbon atoms are preferable. Additionally, the above long-chain alkyl group desirably has 5 to 30 carbon atoms, preferably 10 to 30 carbon atoms, and more preferably, 10 to 20 carbon atoms.

Examples of the alkoxy group denoted by each of $R^1$ and $R^2$ are alkoxy groups having 1 to 30 carbon atoms. As an example of the above short-chain alkoxy group, 1 to 8 carbon atoms are desirable and 1 to 3 carbon atoms are preferred. Additionally, the above long-chain alkoxy group desirably has 5 to 30 carbon atoms, preferably 10 to 30 carbon atoms, and more preferably, 10 to 20 carbon atoms.

In the substituents denoted by -$L^2$-Y, one of which is denoted by each of $R^1$ and $R^2$, the alkylene group denoted by $L^2$ desirably has 5 to 30 carbon atoms, preferably 10 to 30 carbon atoms, and more preferably, 10 to 20 carbon atoms. One of the $CH_2$ groups or two or more of the nonadjacent $CH_2$ groups present in the alkylene group can be substituted with one or more members selected from among the group of divalent groups consisting of —O—, —COO—, —OCO—, —OCOO—, —NRCOO—, —OCONR—, —CO—, —S—, —$SO_2$—, —NR—, —$NRSO_2$—, and —$SO_2NR$— (where R denotes a hydrogen atom or an alkyl group with 1 to 4 carbon atoms). Naturally, it can also be substituted with two or more groups selected from this group of divalent groups. The $CH_2$ that is bonded to Y on the end of $L^2$ can also be substituted with any of the above divalent groups. The $CH_2$ that is bonded to the phenyl group that is on the end of $L^2$ can also be substituted with any of the above divalent groups.

In particular, from the perspective of enhancing solubility, it is desirable for $L^2$ to be an alkyleneoxy group or contain an alkyleneoxy group. It is preferable for $L^2$ to be the polyethyleneoxy group denoted by —($OCH_2OCH_2$)p- (where p denotes a number of 3 or greater, preferably 3 to 10, and more preferably, 3 to 6), or to contain a polyethyleneoxy group.

Examples of -$L^2$- are given below, but the following examples are not limitations. In the formulas below, q denotes a number of 1 or greater, desirably 1 to 10, and preferably, 2 to 6. r denotes 5 to 30, desirably 10 to 30, and preferably, 10 to 20.

—$(OCH_2CH_2)_p$—
—$(OCH_2CH_2)_p$—O—$(CH_2)_q$—
—$(OCH_2CH_2)_p$—OC(=O)—$(CH_2)_q$—
—$(OCH_2CH_2)_p$—OC(=O)NH—$(CH_2)_q$—
—$O(CH_2)_r$—
—$(CH_2)_r$—

In the substituents denoted by -$L^2$-Y, one of which is denoted by each of $R^1$ and $R^2$, Y denotes a hydrogen atom, hydroxy group, alkoxy group (an alkoxy group desirably having 1 to 10 carbon atoms, preferably 1 to 5 carbon atoms), a carboxyl group, a halogen atom, or a polymerizable group.

By combining $L^2$ and Y, the end of -$L^2$-Y can be made a substituent that strengthens intermolecular interaction, such as a carboxyl group, amino group, or ammonium group, or an elimination group such as a sulfonyloxy group or a halogen atom.

The end of -$L^2$-Y can be a substituent forming a covalent bond with other molecules, such as a crosslinking group or a polymerizable group. Examples are —O—C(=O)CH=$CH_2$ and —O—C(=O)CH=$CHCH_3$, and other polymerizable groups.

When used as a material in a cured film, Y is desirably a polymerizable group (where even when the compound denoted by formula (I) above does not contain a polymerizable group, if the compound that is combined is polymerizable, the polymerization reaction of this other compound can be made to progress to fix the orientation of the compound of formula (I)). The polymerization reaction is desirably addition polymerization (including ring-opening polymerization)

or condensation polymerization. That is, the polymerizable group is desirably a functional group capable of undergoing addition polymerization or condensation polymerization. Examples of polymerizable groups are given below.

[Chem. 4]

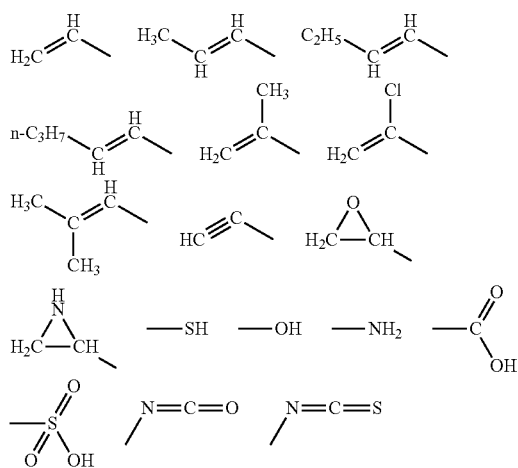

Further, the polymerizable group is preferably a functional group capable of undergoing addition polymerization. Desirable examples of such polymerizable groups are polymerizable ethylenic unsaturated groups and ring-opening polymerizable groups.

The polymerizable group denoted by the following formula is an example of polymerizable groups that are capable of undergoing addition polymerization.

[Chem. 5]

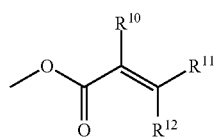

In the formula, each of $R^{10}$, $R^{11}$, and $R^{12}$ independently denotes a hydrogen atom or an alkyl group. The following groups are more specific examples. The alkyl group desirably has 1 to carbon atoms; a methyl group with one carbon atom is optimal. The acrylate group denoted by formula (M-1) below and the methacrylate group denoted by (M-2) below are examples of polymerizable groups denoted by the formula set forth above.

[Chem. 6]

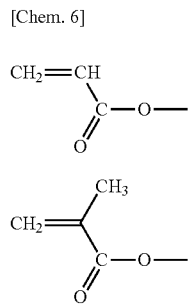

The groups denoted by formulas (M-3) to (M-6) below are additional examples of polymerizable groups that are capable of undergoing addition polymerization.

[Chem. 7]

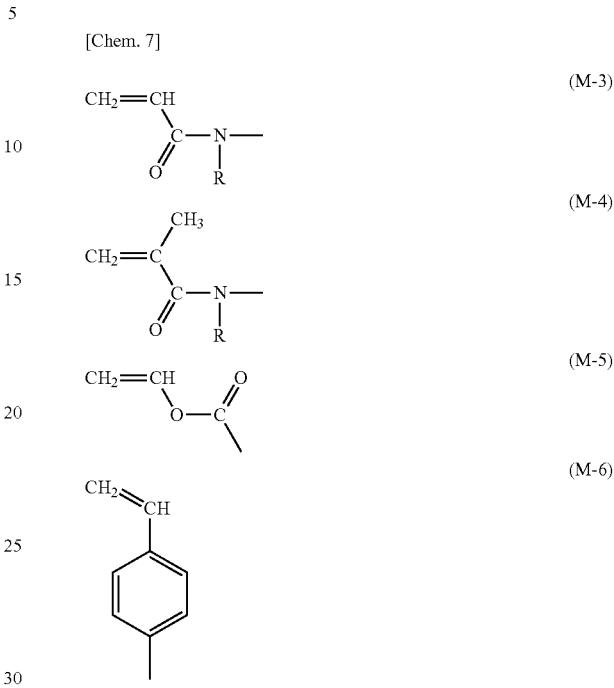

In formulas (M-3) and (M-4), R denotes a hydrogen atom or an alkyl group, desirably a hydrogen atom or a methyl group.

Among formulas (M-1) to (M-6), (M-1) or (M-2) is desirable and (M-1) is preferable.

The ring-opening polymerizable group is desirably a cyclic ether group, preferably an epoxy group or an oxetanyl group, and optimally an epoxy group.

In general formula (I), $L^1$ denotes a linking group selected from the group consisting of azo groups (—N=N—), carbonyloxy groups (—C(=O)O—), oxycarbonyl groups (—O—C(=O)—) imino groups (—N=CH—), and vinylene groups (—C=C—). Of these, vinylene groups are desirable.

In general formula (I), "Dye" denotes an azo dye residue denoted by general formula (II).

[Chem. 8]

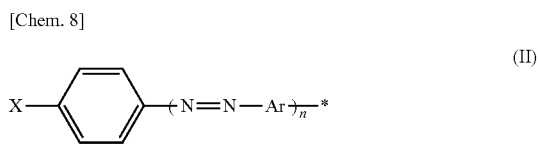

In formula (II), * denotes a bond with $L^1$; X denotes a hydroxy group a substituted or unsubstituted alkyl group, a substituted or unsubstituted alkoxy group, an unsubstituted amino group, or a mono or dialkylamino group; Ar denotes an optionally substituted aromatic hydrocarbon ring or optionally substituted aromatic hetero ring; and n denotes an integer of 1 to 3 such that when n is 2 or greater, the multiple instances of Ar may be identical or mutually different.

The alkyl group denoted by X is desirably an alkyl group having 1 to 12 carbon atoms, preferably 1 to 6 carbon atoms. Specific examples are methyl, ethyl, propyl, and butyl groups. The alkyl group may have a substituent, examples of which are hydroxy groups, carboxyl groups, and polymerizable groups. Desirable examples of polymerizable groups are the desirable examples of polymerizable groups given for Y above.

The alkoxy group denoted by X is an alkoxy group desirably having 1 to 20 carbon atoms, preferably 1 to 10 carbon atoms, and more preferably, 1 to 6 carbon atoms. Specific examples are methoxy groups, ethoxy groups, propoxy groups, butoxy groups, pentoxy groups, hexoxy groups, heptoxy groups, and octoxy groups. The alkoxy group may comprise a substituent, examples of which are hydroxy groups, carboxyl groups, and polymerizable groups. Desirable examples of polymerizable groups are the desirable examples of polymerizable groups given for Y above.

The substituted or unsubstituted amino group denoted by X is an amino group desirably having 0 to 20 carbon atoms, preferably having 0 to 10 carbon atoms, and more preferably, having 0 to 6 carbon atoms. Specific examples are unsubstituted amino groups, methylamino groups, dimethylamino groups, diethylamino groups, methyl and hexyl amino groups, and anilino groups.

Among these, X desirably denotes an alkoxy group.

In general formula (I) above, Ar denotes an optionally substituted aromatic hydrocarbon cyclic group or an aromatic heterocyclic group. Examples of aromatic hydrocarbon cyclic groups and aromatic heterocyclic groups are 1,4-phenylene groups, 1,4-naphthylene groups, pyridine ring groups, pyrimidine ring groups, pyrazine ring groups, quinoline ring groups, thiophene ring groups, thiazole ring groups, thiadiazole ring groups, and thienothiazole ring groups. Of these, 1,4-phenylene groups, 1,4-naphtylene groups, and thienothiazole ring groups are desirable, and 1,4-phenylene groups are optimal.

Alkyl groups with 1 to 10 carbon atoms, hydroxy groups, alkoxy groups with 1 to 10 carbon atoms, and cyano groups are desirable as substituents optionally present on Ar. Alkyl groups having 1 to 2 carbon atoms and alkoxy groups having 1 to 2 carbon atoms are preferred.

n desirably denotes 1 or 2, preferably 1.

The compounds denoted by general formula (Ia) below are examples of the compounds denoted by general formula (I) above. The meaning and desirable range of each of the symbols in the formula are identical to those in formula (I).

[Chem. 9]

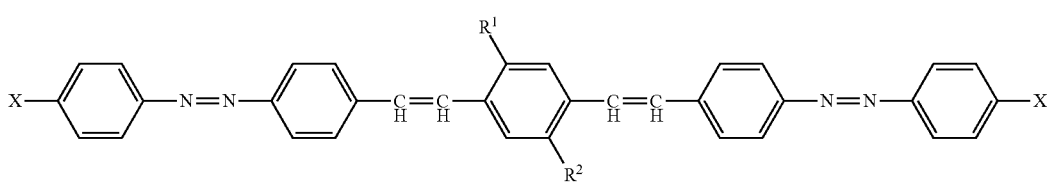

(Ia)

In the formula, the instances of X, which may be identical or different, desirably denote alkoxy groups with 1 to 12 carbon atoms. $R^1$ and $R^2$ are desirably different, with one from among $R^1$ or $R^2$ denoting a hydrogen atom or a short-chain substituent with 1 to 4 carbon atoms (an alkyl group, an alkoxy group, or the substituent denoted by $-L^2-Y$), and the other from among $R^1$ and $R^2$ desirably denoting a long-chain substituent with 5 to 30 carbon atoms (an alkyl group, an alkoxy group, or the substituent denoted by $-L^2-Y$). Alternatively, each of $R^1$ and $R^2$ may denote the substituent denoted by $-L^2-Y$, with $L^2$ desirably denoting an alkyleneoxy group or containing an alkyleneoxy group.

Examples of the compound denoted by general formula (I) above are given below. However, this compound is not limited the compounds given below.

[Chem. 10]

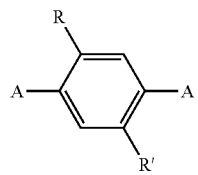

| | A | R | R' |
|---|---|---|---|
| A-1 | n-C₂H₅O—⟨⟩—N=N—⟨⟩—C=C—* (H H) | MeO | *—(OCH₂CH₂)₃—OMe |
| A-2 | n-C₄H₉O—⟨⟩—N=N—⟨⟩—C=C—* (H H) | MeO | *—(OCH₂CH₂)₃—OMe |

-continued
[Chem. 10]
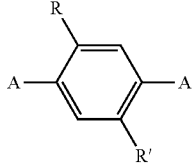
| | A | R | R' |
|---|---|---|---|
| A-3 | 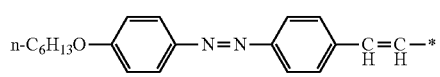 | MeO | *—(OCH$_2$CH$_2$)$_3$—OMe |
| A-4 | 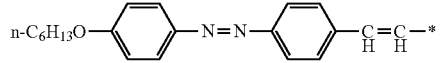 | MeO | *—(OCH$_2$CH$_2$)$_3$—OH |
| A-5 | 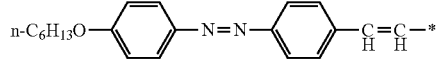 | MeO | *—(OCH$_2$CH$_2$)$_6$—OH |
| A-6 | 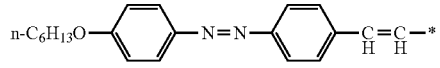 | MeO | 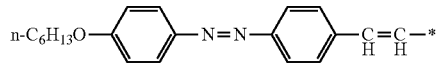 |
| A-7 | 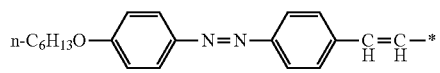 | MeO | 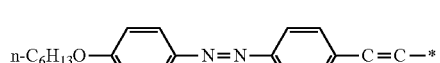 |
| A-8 | 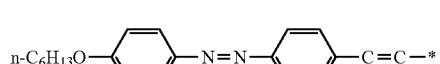 | MeO | 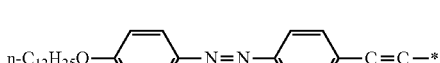 |
| A-9 |  | MeO | *—OC$_{18}$H$_{37}$-n |
| A-10 | 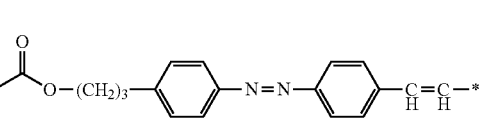 | *—(OCH$_2$CH$_2$)$_3$—OMe | *—(OCH$_2$CH$_2$)$_3$—OMe |
| A-11 | 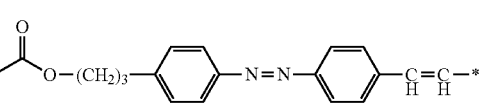 | MeO | *—(OCH$_2$CH$_2$)$_3$—OMe |
| A-12 | | MeO | *—(OCH$_2$CH$_2$)$_3$—OH |
| A-13 | | MeO | |
| A-14 | | MeO | *—(OCH$_2$CH$_2$)$_3$—OMe |

[Chem. 11]

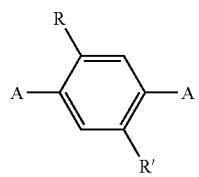

| | A | R | R' |
|---|---|---|---|
| A-15 | (Et)₂N–C₆H₄–N=N–C₆H₄–CH=CH–* | MeO | *—(OCH₂CH₂)₃—OH |
| A-16 | (Et)₂N–C₆H₄–N=N–C₆H₄–CH=CH–* | MeO | *—OC₁₈H₃₇-n |
| A-17 | (Me)(n-C₆H₁₃)N–C₆H₄–N=N–C₆H₄–CH=CH–* | MeO | *—(OCH₂CH₂)₃—OH |
| A-18 | (Et)₂N–C₆H₄–N=N–(naphthyl)–CH=CH–* | MeO | *—(OCH₂CH₂)₃—OH |
| A-19 | (Et)₂N–C₆H₄–N=N–(4-methylthiazol-2-yl)–CH=CH–* | MeO | *—(OCH₂CH₂)₃—OH |
| A-20 | (Et)₂N–C₆H₄–N=N–(thienothiazolyl)–CH=CH–* | MeO | *—(OCH₂CH₂)₃—OH |
| A-21 | (Et)₂N–C₆H₄–N=N–(2-methylphenylene)–N=N–C₆H₄–CH=CH–* | MeO | *—(OCH₂CH₂)₃—OH |
| A-22 | (Et)₂N–C₆H₄–N=N–(naphthalenediyl)–N=N–C₆H₄–CH=CH–* | MeO | *—(OCH₂CH₂)₃—OH |
| A-23 | (Et)₂N–C₆H₄–N=N–(thienothiazolyl)–N=N–C₆H₄–CH=CH–* | MeO | *—(OCH₂CH₂)₃—OH |

[Chem. 12]

structure: 1,4-disubstituted benzene with R (top), R' (bottom), and A groups at 2,5 positions

| | A | R | R' |
|---|---|---|---|
| A-24 | n-C6H13O—C6H4—N=N—C6H4—N=CH—* | MeO | *—(OCH2CH2)3—OH |
| A-25 | n-C6H13O—C6H4—N=N—C6H4—N=CH—* | MeO | *—OC12H25-n |
| A-26 | Et2N—C6H4—N=N—C6H4—N=CH—* | MeO | *—(OCH2CH2)3—OH |
| A-27 | n-C4H9O—C6H4—N=N—C6H4—C(=O)—O—* | MeO | *—(OCH2CH2)6—OH |
| A-28 | n-C4H9O—C6H4—N=N—C6H4—C(=O)—O—* | H | *—OC18H37-n |
| A-29 | (Me)(n-C6H13)N—C6H4—N=N—C6H4—C(=O)—O—* | MeO | *—(OCH2CH2)3—OMe |
| A-30 | Et2N—C6H4—N=N—(thienothiazole)—C(=O)—O—* | MeO | *—(OCH2CH2)3—OH |
| A-31 | n-C6H13O—C6H4—N=N—C6H4—N=N—* | MeO | *—(OCH2CH2)3—OH |
| A-32 | n-C6H13O—C6H4—N=N—C6H4—N=N—* | MeO | *—(OCH2CH2CH2)3—OH |
| A-33 | Et2N—C6H4—N=N—C6H4—N=N—* | MeO | *—(OCH2CH2)3—OMe |
| A-34 | n-C6H13O—C6H4—N=N—C6H4—CH=CH—* | MeO | MeO |

The crystallinity exhibited by the liquid-crystal compound denoted by general formula (I) above is not specifically limited. Liquid crystallinity can be thermotropic or lyotropic; either will do. Of these, a liquid crystal compound exhibiting thermotropic liquid crystallinity is desirable, and one exhibiting a nematic phase within a range of 100 to 300° C. is preferred.

The liquid-crystal compound that is denoted by formula (I) above has good solubility. Among compounds denoted by formula (I), there exist compounds having a solubility in chloroform of 2% by mass or greater, even 5% by mass or greater. Solubility to such concentration ranges facilitates preparation of a coating liquid and affords good handling properties.

The liquid-crystal compound denoted by formula (I) above is capable of orienting with a high degree of orientation order. There are compounds denoted by formula (I) that may have an orientation order S of 0.90 or higher, even 0.95 or higher.

The compound of the present invention functions as a dichroic dye. Thus, the orientation order can be calculated by forming a film of the compound and measuring the dichroic ratio of the film. Details of the measurement method are given in the embodiments.

The compound denoted by formula (I) can be synthesized by combining various organic synthesis methods. For example, compound A below can be used as starting material:

[Chem. 13]

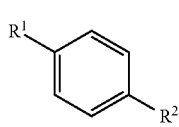

Compound A

Compound A is mixed with paraformaldehyde in an acetic acid solution of hydrobromic acid and heated to convert it to Compound B below.

[Chem. 14]

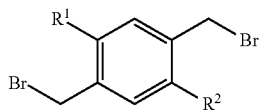

Compound B

Compound B is mixed with triethyl phosphate in toluene and heated to convert it to compound C below.

[Chem. 15]

Compound C

Compound C is converted to a phosphorus ylide with sodium hydroxide in toluene and reacted with compound D.

[Chem. 16]

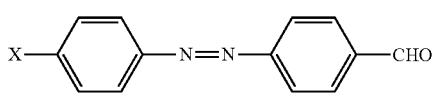

Compound D

That synthesizes a compound of formula (I) in which Ar is a phenylene group and $L^1$ is a vinylene group.

Compound A can also be reacted with iodine monochloride to convert it to compound E below.

[Chem. 17]

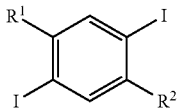

Compound E

Compound E can be reacted with ammonia in the presence of a copper catalyst to convert it to compound F below.

[Chem. 18]

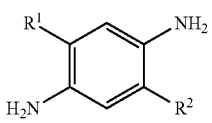

Compound F

Compound F can be reacted with compound D above.

That synthesizes a compound of formula (I) in which Ar is a phenylene group and $L^1$ is an imino group.

It is possible to synthesize a compound of formula (I) in which Ar is a phenylene group and $L^1$ is a carbonyloxy group or oxycarbonyl group.

Compound F can be converted to a diazo and reacted with an aniline derivative to convert it to compound G below.

[Chem. 19]

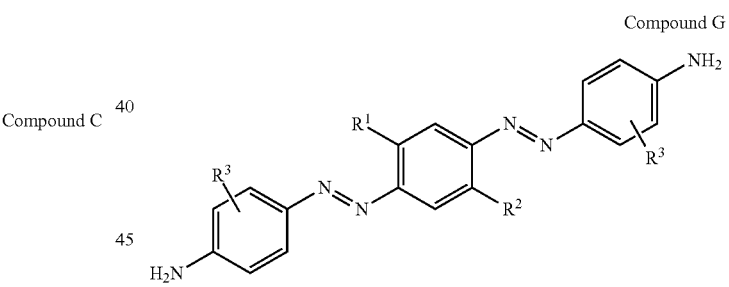

Compound G

Through repeated diazotization coupling, it is possible to synthesize a compound of formula (I) in which Ar is a phenylene group and $L^1$ is an azo group.

Further, compound F can be diazotized and then hydrolyzed in an acidic aqueous solution to convert it to compound H below.

[Chem. 20]

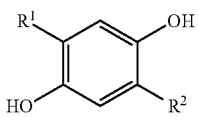

Compound H

Compound H can be reacted with the compound I derivative below.

Compound I

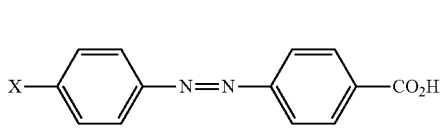

That synthesizes a compound of formula (I) in which Ar is a phenylene group and $L^1$ is a carbonyloxy group or oxycarbonyl group.

Compound A in which $R^2$ is a polyethyleneethyleneoxy group and the end is OH or an alkoxy group can be synthesized by reacting compound a below:

[Chem. 21]

Compound a

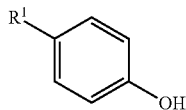

with polyethylene glycol monochlorohydrin, polyethylene glycol monochloromonoalkyl ether, or the like.

2. The Liquid-Crystal Composition

The present invention also relates to a liquid-crystal composition comprising at least one liquid-crystal compound denoted by formula (I). The liquid-crystal composition of the present invention is useful in the manufacturing of optical elements such as light absorption anisotropic films.

The liquid-crystal composition can comprise two or more liquid-crystal compounds denoted by formula (I), and can comprise other liquid-crystal compounds in addition to the liquid-crystal compound denoted by formula (I).

The color tone of the liquid-crystal composition of the present invention is not specifically limited. It can be prepared as a composition of various tones based on the application. For example, in a form employed to prepare a polarizer, two or more dyes are desirably mixed to obtain a black composition. The proportions of the dyes that are mixed are not specifically limited, and can be suitably selected based on the color tone of the dye employed and the desired color tone of the composition. When the liquid-crystal composition is being used to manufacture a light absorption anisotropic film such as a polarizing film, a compound that is black on its own or in combinations of two or more is desirably selected. The liquid-crystal compound denoted by formula (I) is an azo compound that absorbs light in the visible range. Although the wavelength of the maximum absorption peak will vary based on the type of substituents and the like, the compound will have a maximum absorption peak of about 400 to 600 nm. Accordingly, to achieve black, it is desirable to blend a dye having a maximum absorption peak of 600 nm or higher. Examples of dyes that can be combined for use are other azo dyes, cyanine dyes, azo-metal complexes, phthalocyanine dyes, pyrylium dyes, thiopyrylium dyes, azulenium dyes, squarylium dyes, naphthoquinone dyes, triphenylmethane dyes, and triarylmethane dyes.

For example, the dyes denoted by formulas (X) to (XIV) below are examples of dyes that can be employed in combination.

[Chem. 22]

General formula (X)

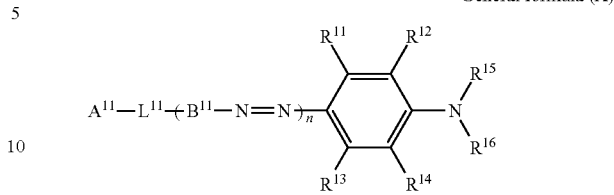

In the formula, each of $R^{11}$ to $R^{14}$ independently denotes a hydrogen atom or a substituent. Each of $R^{15}$ and $R^{16}$ independently denotes a hydrogen atom or an optionally substituted alkyl group. $L^{11}$ denotes —N=N—, —CH=N—, —N=CH—, —C(=O)O—, —OC(=O)—, or —CH=CH—. $A^{11}$ denotes an optionally substituted phenyl group, an optionally substituted naphthyl group, or an optionally substituted aromatic heterocyclic group. $B^{11}$ denotes an optionally substituted divalent aromatic hydrocarbon group or divalent aromatic heterocyclic group. n denotes an integer of from 1 to 5; when n is 2 or greater, the multiple instances of $B^{11}$ may be identical or different.

[Chem. 23]

General Formula (XI)

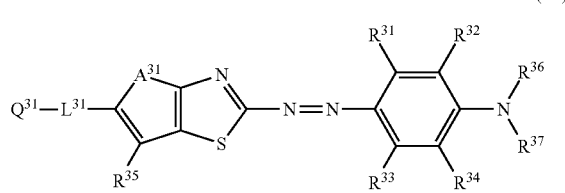

In the formula, each of $R^{31}$ to $R^{35}$ independently denotes a hydrogen atom or a substituent. Each of $R^{36}$ and $R^{37}$ independently denotes a hydrogen atom or an optionally substituted alkyl group. $Q^{31}$ denotes an optionally substituted aromatic hydrocarbon group, an aromatic heterocyclic group, or a cyclohexane ring group. $L^{31}$ denotes a divalent linking group. And $A^{31}$ denotes an oxygen atom or a sulfur atom.

[Chem. 24]

General Formula (XII)

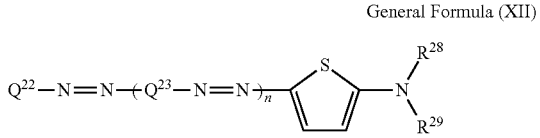

In the formula, each of $R^{28}$ and $R^{29}$ independently denotes a hydrogen atom or an optionally substituted alkyl group. $Q^{22}$ denotes an optionally substituted aromatic hydrocarbon group or an aromatic heterocyclic group. $Q^{23}$ denotes an optionally substituted divalent aromatic hydrocarbon group or a divalent aromatic heterocyclic group. n denotes an integer of from 1 to 4; when n is 2 or greater, the multiple instances of $Q^{23}$ may be identical or different.

[Chem. 25]

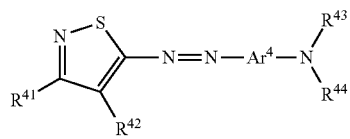

General Formula (XIII)

In the formula, each of $R^{41}$ and $R^{42}$ denotes a hydrogen atom or a substituent, and may be bonded together to form a ring. $Ar^4$ denotes an optionally substituted divalent aromatic hydrocarbon group or an optionally substituted aromatic heterocyclic group. Each of $R^{43}$ and $R^{44}$ denotes a hydrogen atom or an optionally substituted alkyl group, and may be bonded together to form a hetero ring.

[Chem. 26]

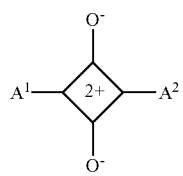

General Formula (XIV)

In the formula, each of $A^1$ and $A^2$ independently denotes an aromatic hydrocarbon ring group or aromatic heterocyclic group.

The combination of dyes that are blended is not specifically limited. However, they are desirably mixed so that the hue of the composition is black. In particular, with regard to general formula (I), general formula (X) is desirably blended to obtain a dye of long wavelength, general formula (XI) or (XII) is desirably blended to obtain a dye of longer wavelength, and general formula (XIII) or (XIV) is desirably blended to obtain a dye of even longer wavelength.

Examples of compounds denoted by general formulas (X) to (XIV) are given below. However, there is no limitation to the compounds given below.

The following compounds are specific examples of the compound denoted by general formula (X). However, it is not limited thereto.

[Chem. 27]

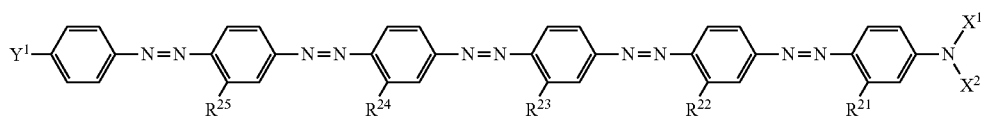

| No. | $X^1$ | $X^2$ | $R^{21}$ | $R^{22}$ | $R^{23}$ | $R^{24}$ | $R^{25}$ | $Y^1$ |
|---|---|---|---|---|---|---|---|---|
| A1-1 | —$C_2H_5$ | —$C_2H_5$ | —H | —$CH_3$ | —H | —H | —H | —$C_4H_9$ |
| A1-2 | —$C_2H_5$ | —$C_2H_5$ | —H | —$CH_3$ | —$CH_3$ | —$CH_3$ | —H | —$C_4H_9$ |
| A1-3 | —$CH_3$ | —$CH_3$ | —H | —$CH_3$ | —H | —H | —H | —$C_4H_9$ |

[Chem. 28]

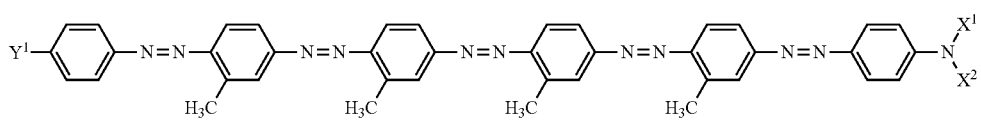

| No. | $X^1$ | $X^2$ | $Y^1$ |
|---|---|---|---|
| A1-4 | —$C_2H_5$ | —$C_2H_5$ | —O—C(=O)—C6H4—O(CH$_2$)$_4$OCOCH=CH$_2$ |
| A1-5 | —$C_2H_5$ | —$C_2H_5$ | —O—C(=O)—C6H4—O(CH$_2$)$_{11}$OCOCH=CH$_2$ |

[Chem. 29]

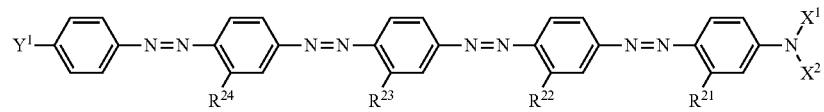

| No. | X¹ | X² | R²¹ | R²² | R²³ | R²⁴ | Y¹ |
|---|---|---|---|---|---|---|---|
| A1-9 | —$C_2H_5$ | —$C_2H_5$ | —H | —$CH_3$ | —H | —H | —$C_4H_9$ |
| A1-10 | —$C_2H_5$ | —$C_2H_5$ | —$CH_3$ | —$CH_3$ | —H | —H | —$C_4H_9$ |
| A1-11 | —$C_2H_5$ | —$C_2H_5$ | —H | —$CH_3$ | —$CH_3$ | —$CH_3$ | —$C_4H_9$ |
| A1-15 | —$C_2H_5$ | —$C_2H_5$ | —H | —$CH_3$ | —$CH_3$ | —$CH_3$ | —O—C(=O)—C₆H₄—O(CH₂)₄OCOCH=CH₂ |

[Chem. 30]

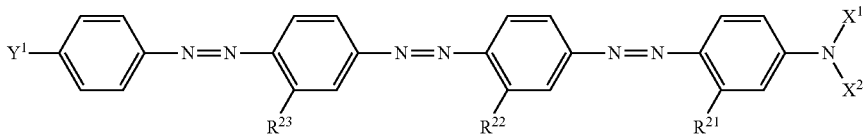

| No. | X¹ | X² | R²¹ | R²² | R²³ | Y¹ |
|---|---|---|---|---|---|---|
| A1-16 | —$C_2H_5$ | —$C_2H_5$ | —H | —$CH_3$ | —H | —$C_4H_9$ |
| A1-17 | —$C_2H_5$ | —$C_2H_5$ | —H | —$CH_3$ | —$CH_3$ | —$C_4H_9$ |
| A1-18 | —$C_2H_5$ | —$C_2H_5$ | —H | —$CH_3$ | —H | —O—C(=O)—C₆H₄—O(CH₂)₄OCOCH=CH₂ |
| A1-19 | —$C_2H_5$ | —$C_2H_5$ | —H | —$CH_3$ | —H | —O—C(=O)—C₆H₄—O(CH₂)₁₁OCOCH=CH₂ |
| A1-24 | —$C_2H_5$ | —$C_2H_5$ | —$OCH_3$ | —$CH_3$ | —H | —$C_4H_9$ |
| A1-25 | —$C_2H_5$ | —$C_2H_5$ | —H | —$CH_3$ | —$CH_3$ | —O—C(=O)—C₆H₄—O(CH₂)₄OCOCH=CH₂ |

[Chem. 31]

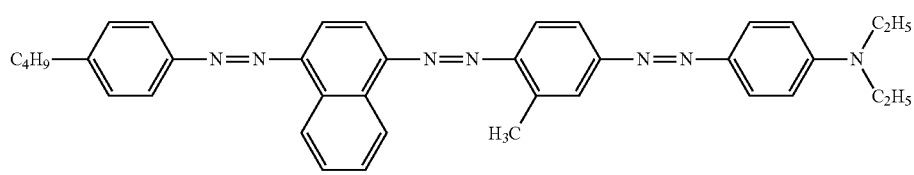

A1-27

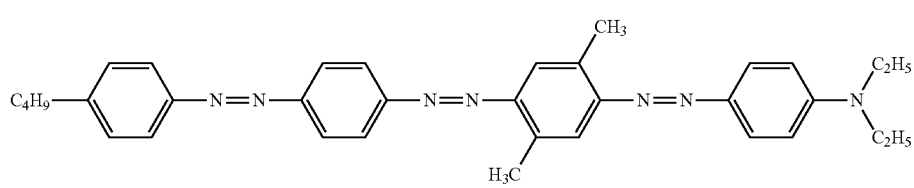

A1-28

-continued
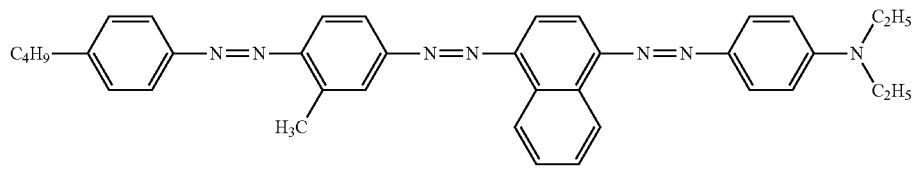
A1-29
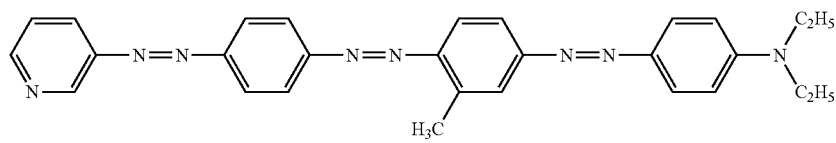
A1-30
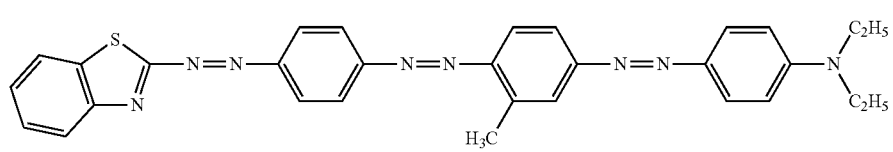
A1-31
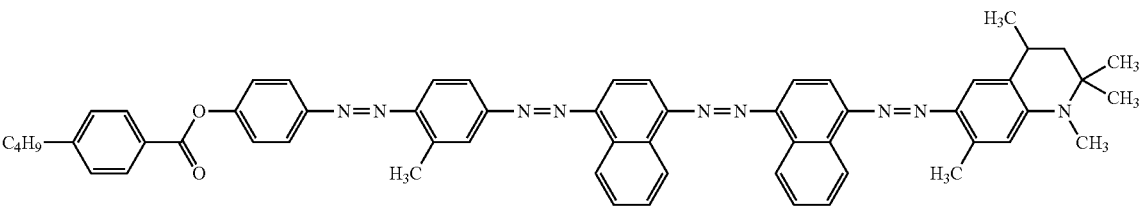
A1-32
[Chem. 32]
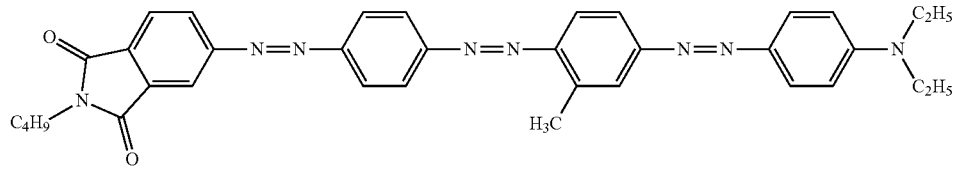
A1-33
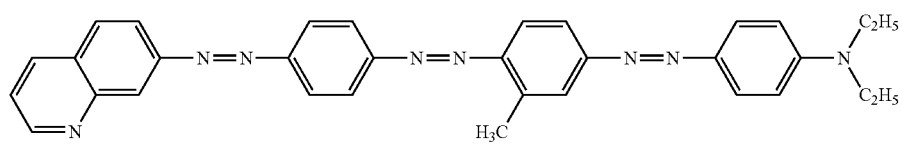
A1-34
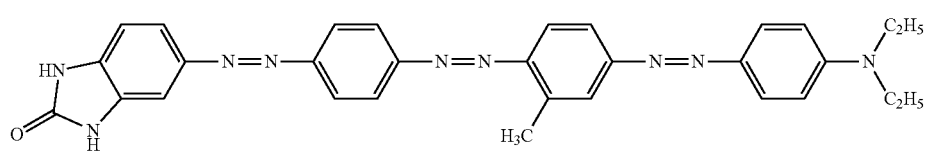
A1-35
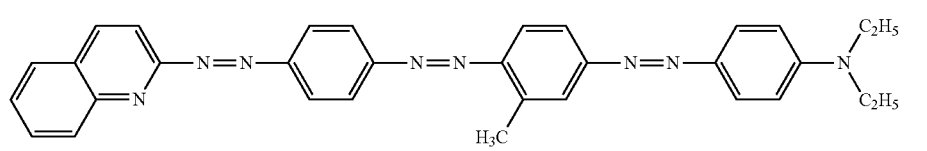
A1-36
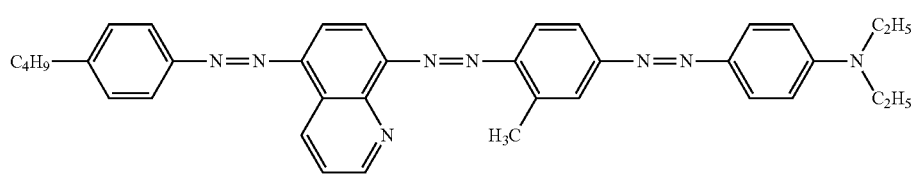
A1-37

-continued
[Chem. 33]
A1-38
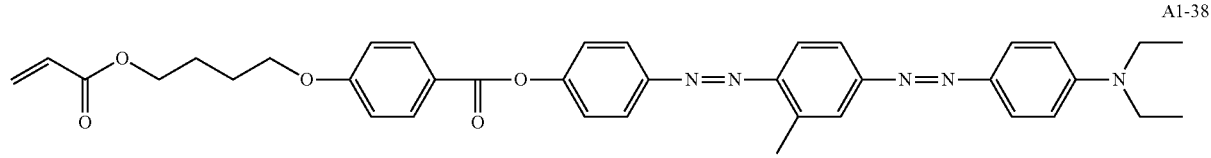
A1-40
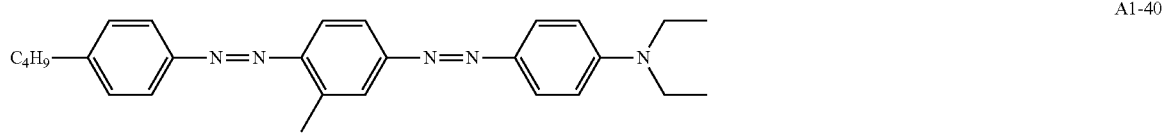
[Chem. 34]
A1-41
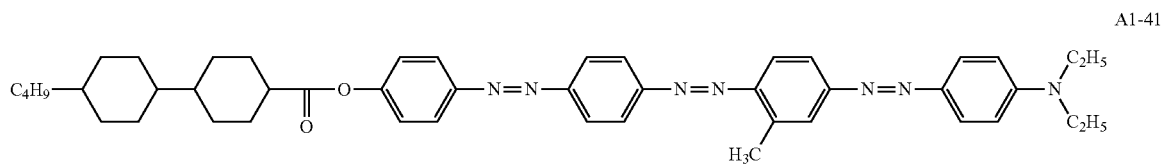
A1-42
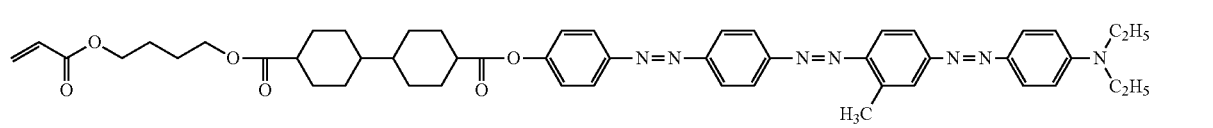
A1-45
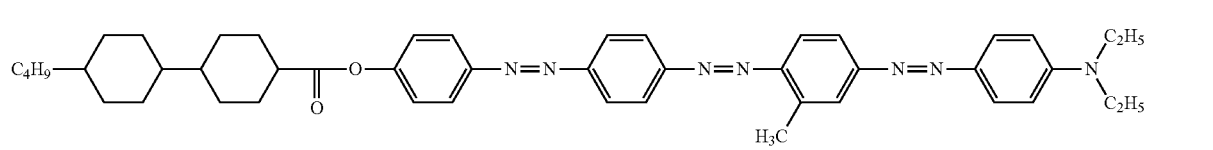
[Chem. 35]
A1-46
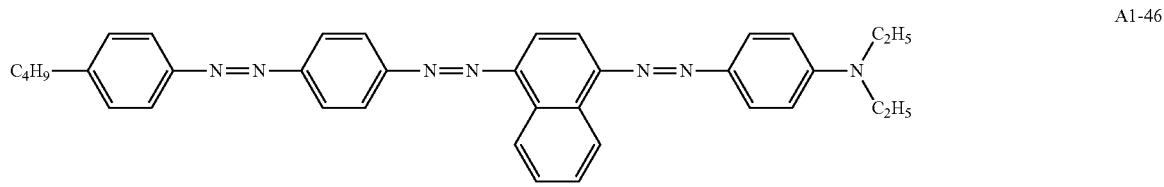
A1-47
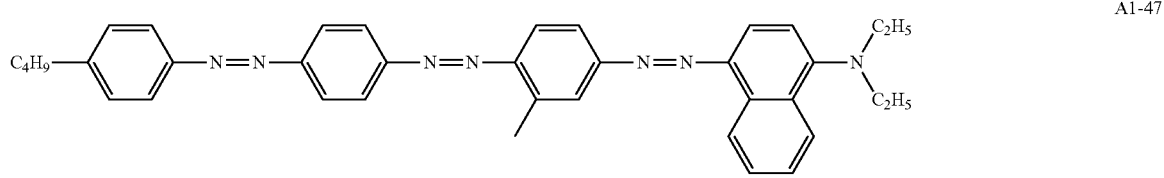
A1-48
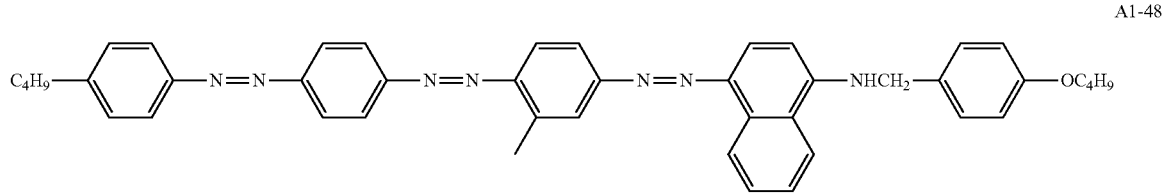
A1-50    A1-51
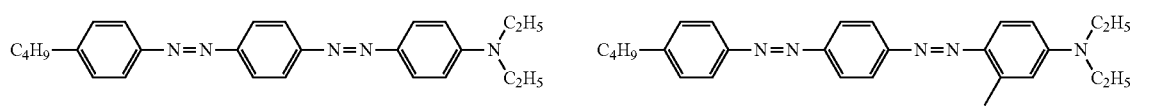

-continued
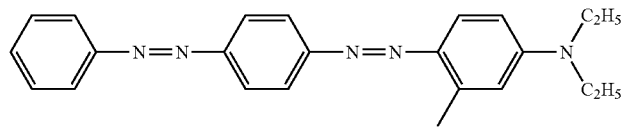
A1-52
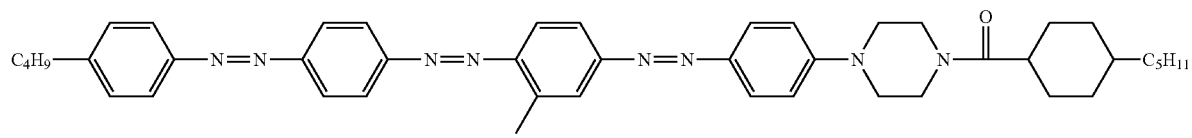
A1-53
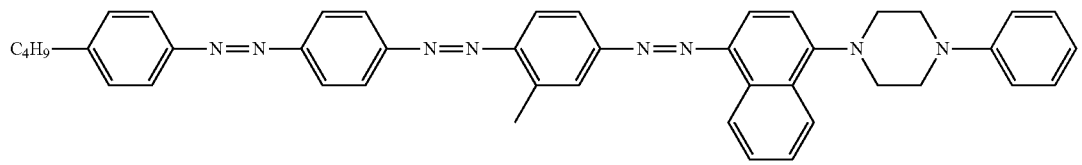
A1-54
[Chem. 36]
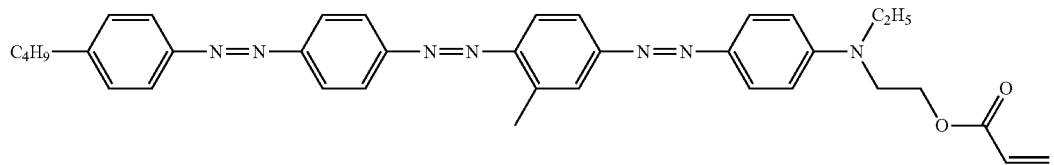
A1-55
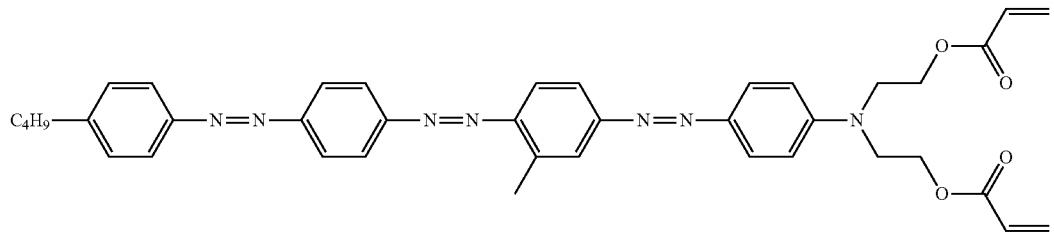
A1-56
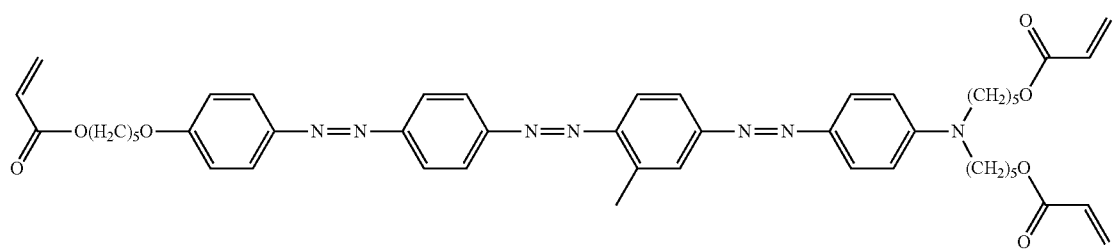
A1-57
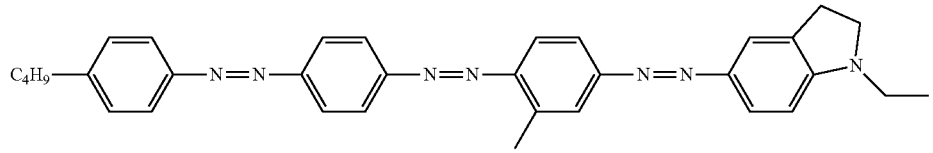
A1-58

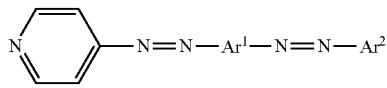
| Compound Example | Ar¹ | Ar² |
|---|---|---|
| B-1 | *-C₆H₄-* (1,4) | *-C₆H₄-N(Et)₂ |
| B-2 | *-C₆H₃(CH₃)-* (2-methyl-1,4) | *-C₆H₄-N(Et)₂ |
| B-3 | *-C₆H₃(CH₃)-* (2-methyl-1,4) | *-(5-indolinyl)-N-Et |
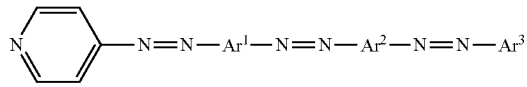
| Compound Example | Ar¹ | Ar² | Ar³ |
|---|---|---|---|
| B-4 | *-C₆H₄-* (1,4) | *-C₆H₃(CH₃)-* (2-methyl-1,4) | *-C₆H₄-N(Et)₂ |
| B-5 | *-C₆H₃(CH₃)-* (2-methyl-1,4) | *-C₆H₃(CH₃)-* (2-methyl-1,4) | *-C₆H₄-N(Et)₂ |
| B-6 | *-C₆H₄-* (1,4) | *-C₆H₃(CH₃)-* (2-methyl-1,4) | *-C₆H₄-N(nBu)₂ |
| B-7 | *-C₆H₄-* (1,4) | *-C₆H₃(CH₃)-* (2-methyl-1,4) | *-C₆H₄-N(Et)(CH₂CH₂OH) |
| B-8 | *-C₆H₄-* (1,4) | *-C₆H₃(CH₃)-* (2-methyl-1,4) | *-(5-indolinyl)-N-Et |

-continued

[Chem. 38]

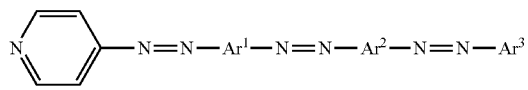

| Compound Example | Ar¹ | Ar² | Ar³ |
|---|---|---|---|
| B-9 | *–⟨phenyl-1,4⟩–* | *–⟨2-methylphenyl-1,4⟩–* | *–⟨5-indolinyl, N-(CH₂)₃CO₂H⟩ |

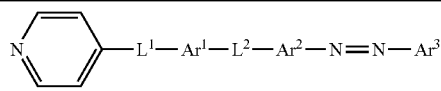

| Compound Example | L¹ | Ar¹ | L² | Ar² | Ar³ |
|---|---|---|---|---|---|
| B-10 | *–N=N–* | *–⟨2-methylphenyl-1,4⟩–* | *–O–C(=O)–* | *–⟨phenyl-1,4⟩–* | *–⟨4-(N-methyl-N-(2-methoxyethyl)amino)phenyl⟩ |
| B-11 | *–N=N–* | *–⟨2-methylphenyl-1,4⟩–* | *–N=CH–* | *–⟨phenyl-1,4⟩–* | *–⟨4-(N,N-diethylamino)phenyl⟩ |
| B-12 | *–CH=CH–* | *–⟨phenyl-1,4⟩–* | *–O–C(=O)–* | *–⟨2-methylphenyl-1,4⟩–* | *–⟨4-(N,N-diethylamino)phenyl⟩ |
| B-13 | 2-chloropyridin-4-yl–N=N–⟨phenyl-1,4⟩–N=N–⟨2-methylphenyl-1,4⟩–N=N–⟨4-(N,N-diethylamino)phenyl⟩ | | | | |
| B-14 | pyridin-4-yl–N=N–⟨phenyl-1,4⟩–N=N–⟨2-methylphenyl-1,4⟩–N=N–⟨2-methylphenyl-1,4⟩–N=N–⟨4-(N,N-diethylamino)phenyl⟩ | | | | |

[Chem. 39]

C-1

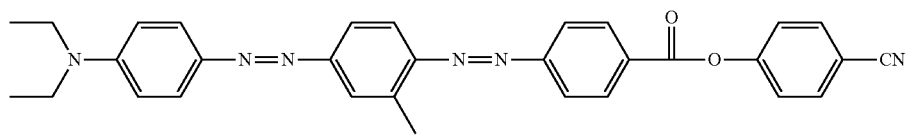

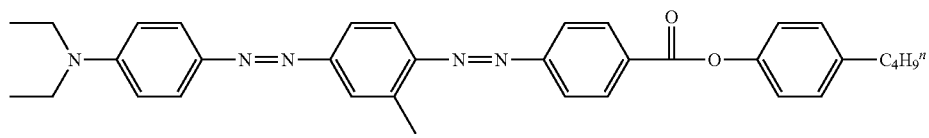 C-2
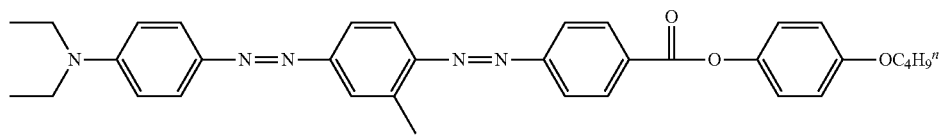 C-3
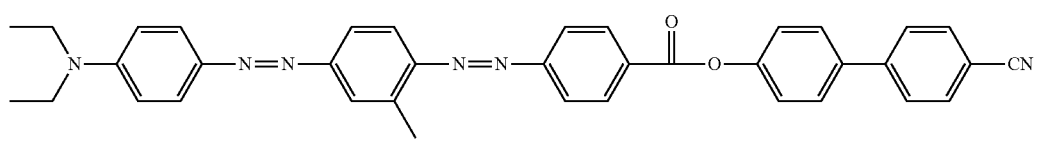 C-4
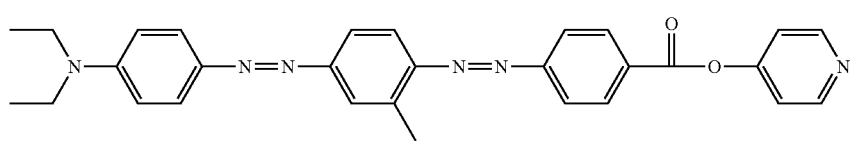 C-5
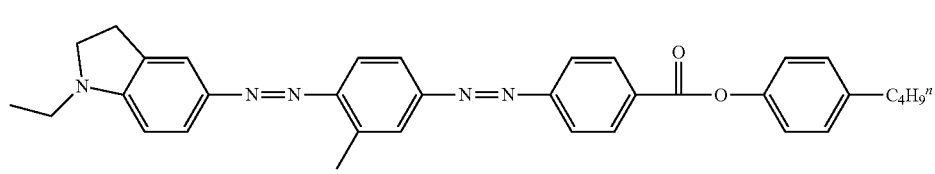 C-6
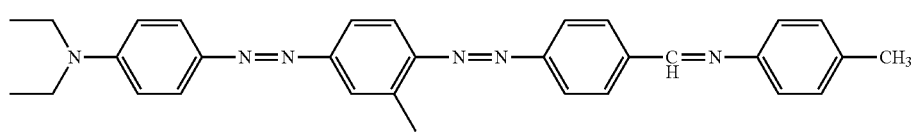 C-7
[Chem. 40]
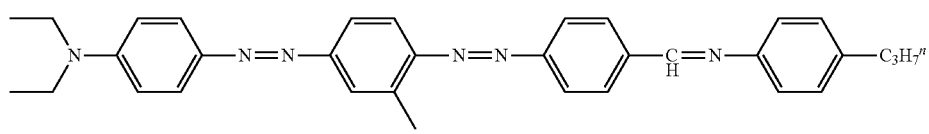 C-8
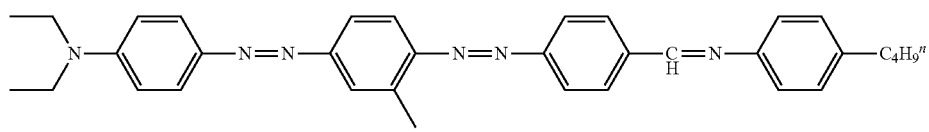 C-9
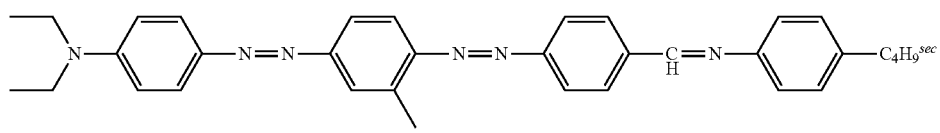 C-10
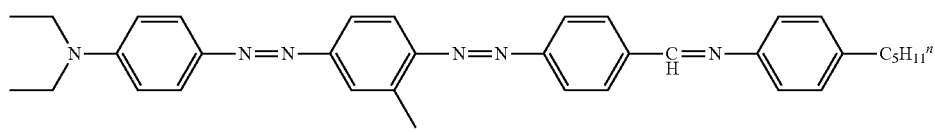 C-11
C-12

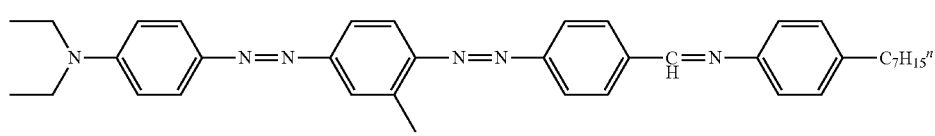 C-13
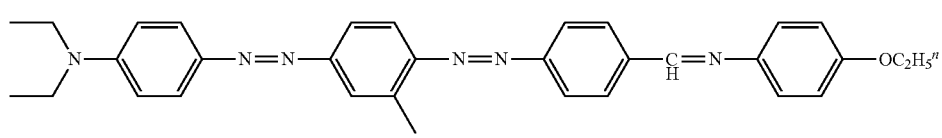 C-14
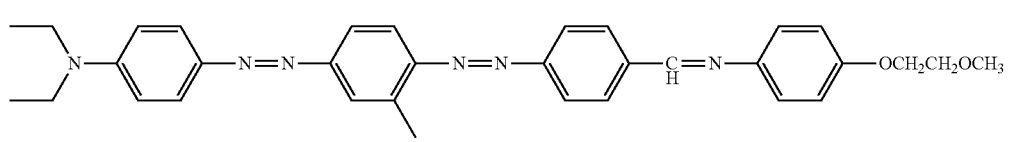 C-15
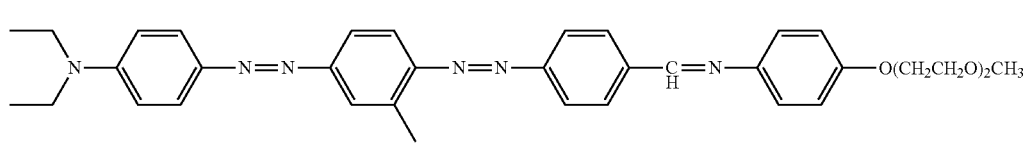 C-16
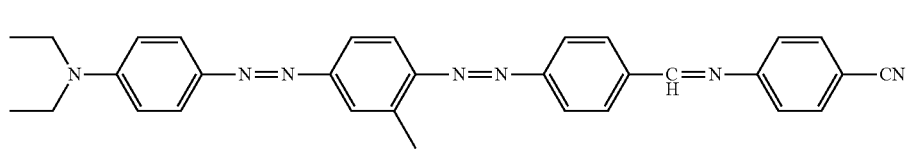 C-17
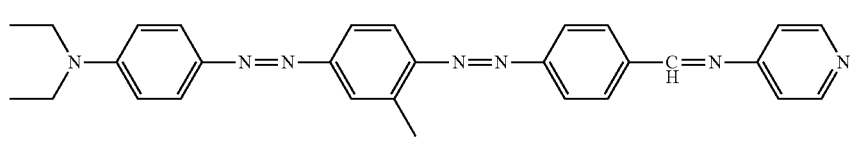 C-18
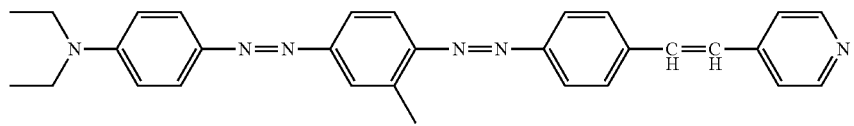 C-19
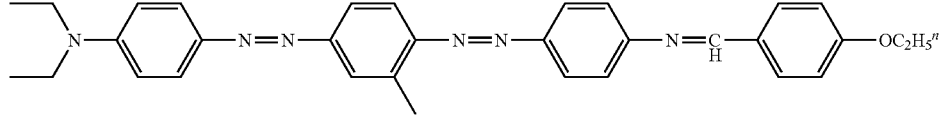 C-20
[Chem. 41]
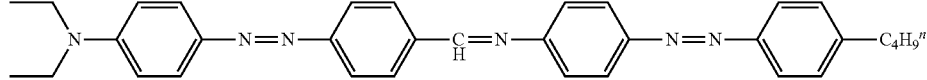 C-21
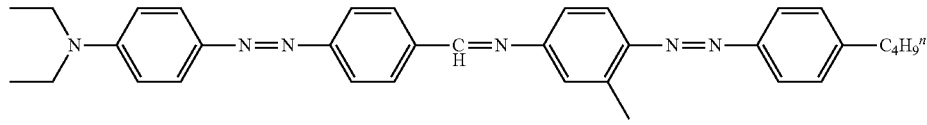 C-22
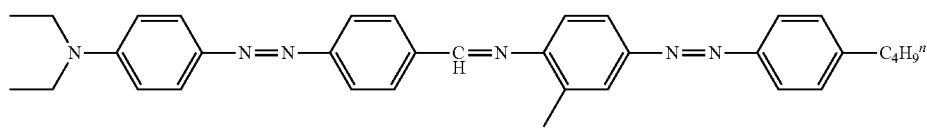 C-23
C-24

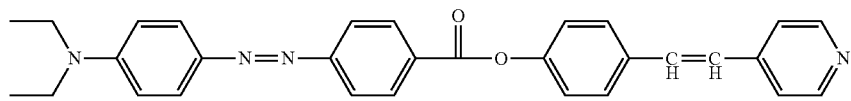
C-25
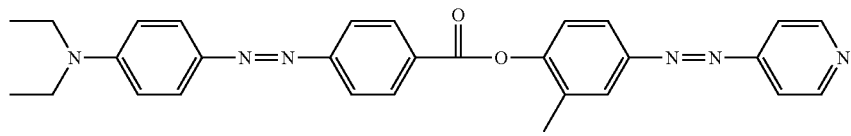
C-26
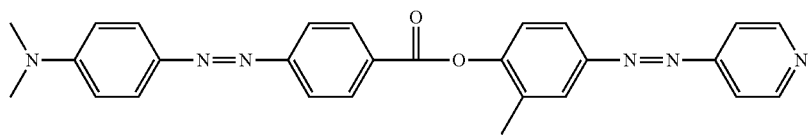
C-27
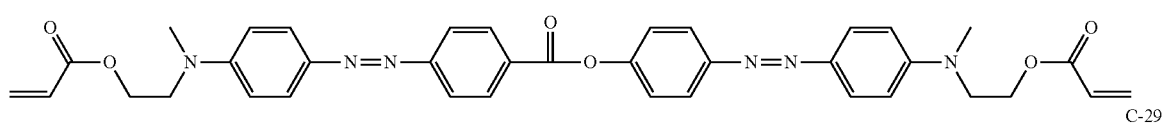
C-28
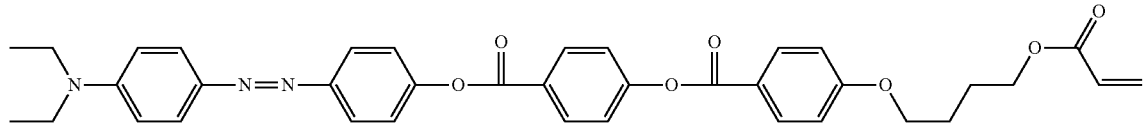
C-29
Specific examples of the compound denoted by general formula (XI) above are given below. However, it is not limited thereto.
[Chem. 42]
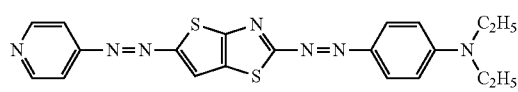
(A2-34)
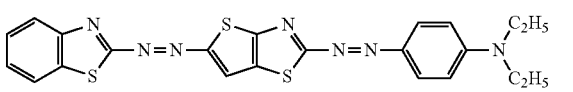
(A2-35)
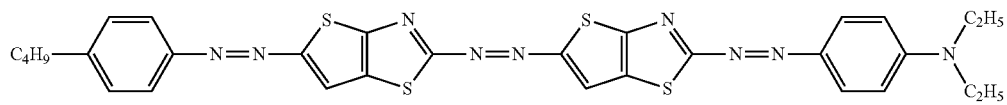
(A2-36)
[Chem. 43]
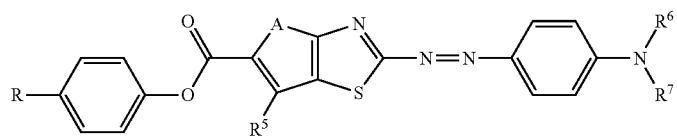
| No. | A | $R^5$ | $R^6$ | $R^7$ | R |
|---|---|---|---|---|---|
| A2-37 | S | —H | —$C_2H_5$ | —$C_2H_5$ | —$C_4H_9$ |
| A2-38 | S | —H | —$C_2H_5$ | —$C_2H_5$ | —$C_7H_{15}$ |
| A2-39 | S | —H | —$C_2H_5$ | —$C_2H_5$ | —CN |
| A2-40 | S | —H | —$C_2H_5$ | —$C_2H_5$ | —Br |
| A2-41 | S | —$CH_3$ | —$C_2H_5$ | —$C_2H_5$ | —$C_4H_9$ |
| A2-42 | S | —H | —$CH_3$ | —$CH_3$ | —$C_4H_9$ |
| A2-43 | O | —H | —$C_2H_5$ | —$C_2H_5$ | —$C_4H_9$ |

[Chem. 44]
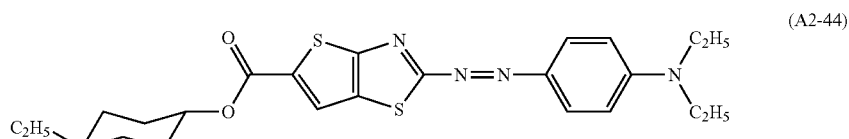
(A2-44)
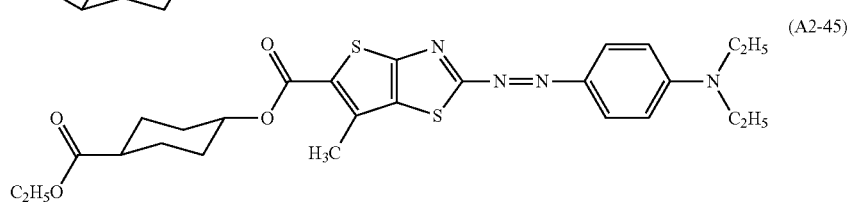
(A2-45)
[Chem. 45]
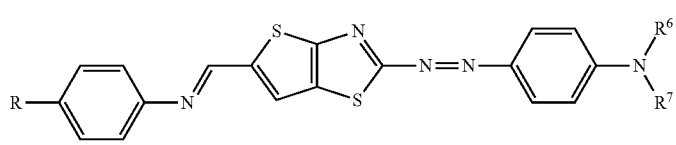
| No. | R⁶ | R⁷ | R |
|---|---|---|---|
| A2-46 | —$C_2H_5$ | —$C_2H_5$ | —$C_4H_9$ |
| A2-47 | —$C_2H_5$ | —$C_2H_5$ | —$OC_4H_9$ |
| A2-48 | —$C_2H_5$ | —$C_2H_5$ | —$CF_3$ |
| A2-49 | —$C_2H_5$ | —$C_2H_5$ | —F |
| A2-50 | —$CH_3$ | —$CH_3$ | —$C_4H_9$ |
[Chem. 46]
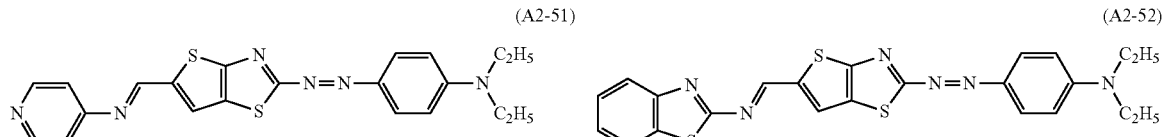
(A2-51) (A2-52)
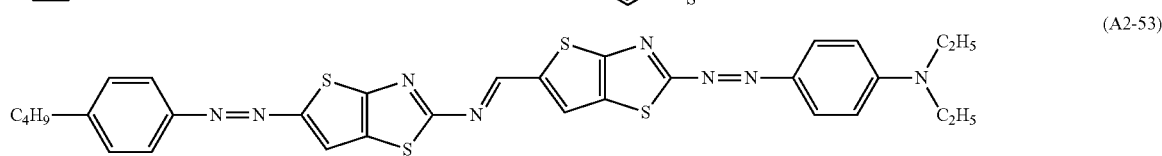
(A2-53)
Specific examples of the compound denoted by general formula (XII) above are given below. However, it is not limited thereto.
[Chem. 47]
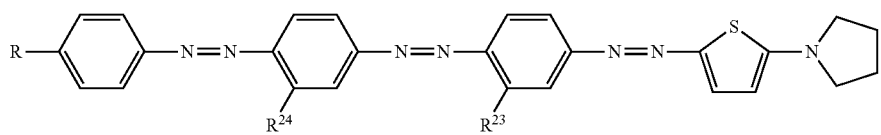
| No. | R²³ | R²⁴ | R |
|---|---|---|---|
| B3-1 | —H | —H | —$C_4H_9$ |
| B3-2 | —H | —$CH_3$ | —$C_4H_9$ |
| B3-3 | —$CH_3$ | —H | —$C_4H_9$ |

-continued
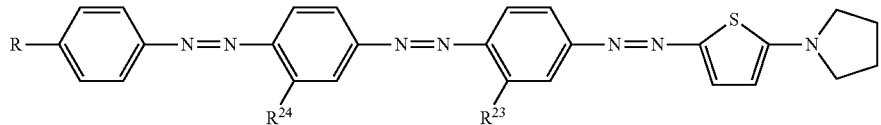
[Chem. 47]
| No. | $R^{23}$ | $R^{24}$ | R |
|---|---|---|---|
| B3-4 | —$CH_3$ | —$CH_3$ | —$C_4H_9$ |
| B3-5 | —$CH_3$ | —H | —$C_7H_{15}$ |
| B3-6 | —$CH_3$ | —H | —$OC_4H_9$ |
| B3-7 | —$CH_3$ | —H | —$CF_3$ |
| B3-8 | —$CH_3$ | —H | —OH |
| B3-9 | —$CH_3$ | —H | —CN |
| B3-10 | —$CH_3$ | —H | —$NO_2$ |
| B3-11 | —$CH_3$ | —H | —F |
| B3-12 | —$CH_3$ | —H | —Br |
| B3-13 | —$CH_3$ | —H | —I |
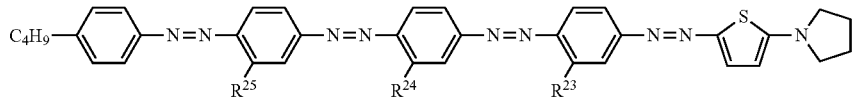
[Chem. 48]
| No. | $R^{32}$ | $R^{24}$ | $R^{25}$ |
|---|---|---|---|
| B3-14 | —H | —H | —H |
| B3-15 | —H | —H | —$CH_3$ |
| B3-16 | —H | —$CH_3$ | —H |
| B3-17 | —$CH_3$ | —H | —H |
| B3-18 | —$CH_3$ | —$CH_3$ | —H |
| B3-19 | —$CH_3$ | —$CH_3$ | —$CH_3$ |
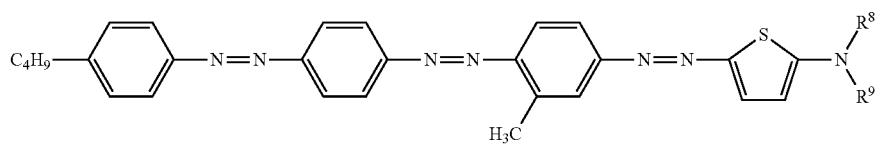
[Chem. 49]
| No. | $R^8$ | $R^9$ |
|---|---|---|
| B3-20 | —$CH_3$ | —$CH_2CH_2OH$ |
| B3-21 | —$CH_3$ | —$CH_2CH_2OCH_3$ |
| B3-22 | —$C_2H_5$ | —$CH_2CH_2OCH_3$ |
[Chem. 50]
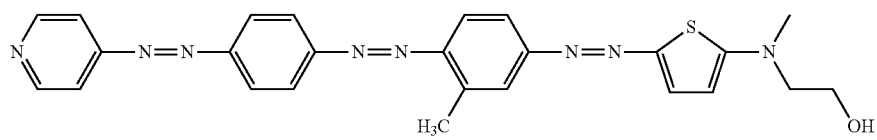
(B3-23)

-continued
(B3-24)
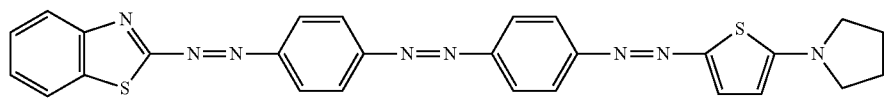
(B3-25)
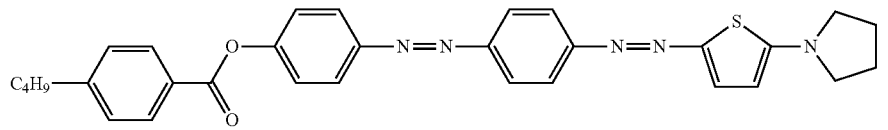
(B3-26)
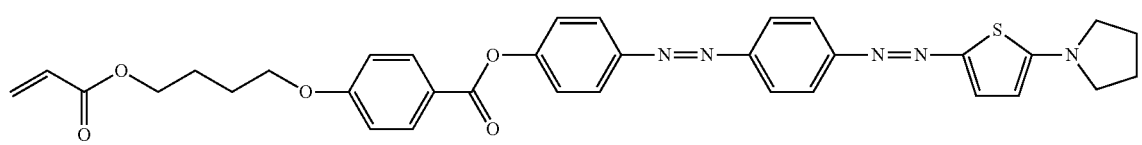
(B3-27)
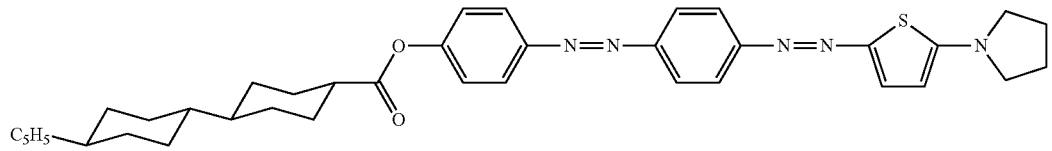
Specific examples of the compound denoted by general formula (XIII) above are given below. However, it is not limited thereto.
[Chem. 51]
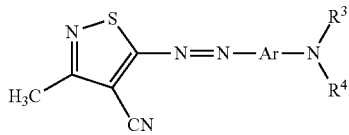
| No. | Ar | $R^3$ | $R^4$ |
|---|---|---|---|
| 1 | *—⟨phenyl⟩—* | —CH$_3$ | —CH$_2$Ph |
| 2 | ↑ | ↑ | —C$_{12}$H$_{25}$ |
| 3 | ↑ | ↑ | —(CH$_2$CH$_2$O)$_3$CH$_3$ |
| 4 | ↑ | ↑ | —CH$_2$CH$_2$OCH$_2$Ph |
| 5 | ↑ | —H | —CH$_2$Ph |
| 6 | ↑ | —C$_2$H$_5$ | ↑ |
| 7 | ↑ | | *—N(pyrrolidine) |
| 8 | ↑ | | *—N(morpholine) |
| 9 | *—⟨2-methylphenyl⟩—* | —CH$_3$ | —CH$_2$Ph |
| 10 | *—⟨2-chlorophenyl⟩—* | ↑ | ↑ |

-continued
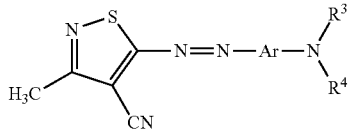
[Chem. 51]
| No. | Ar | R³ | R⁴ |
|---|---|---|---|
| 11 | ![](OCH3/AcHN phenyl) | ↑ | ↑ |
| 12 | naphthyl | ↑ | ↑ |
| 13 | indoline-N-R⁴ | | ↑ |
| 14 | pyridyl | —CH₃ | ↑ |
| 15 | thienyl | ↑ | —CH₂CH₂OCH₂Ph |
| 16 | ↑ | | *—N(pyrrolidine) |
| 17 | 3-CN-thienyl | | ↑ |
[Chem. 52]
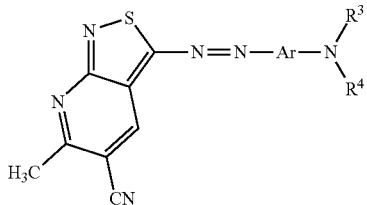
| No. | Ar | R³ | R⁴ |
|---|---|---|---|
| 18 | 1,4-phenylene | —CH₃ | —CH₂Ph |
-continued
[Chem. 52]
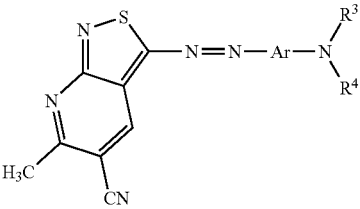
| No. | Ar | R³ | R⁴ |
|---|---|---|---|
| 19 | ↑ | | *—N(pyrrolidine) |

-continued

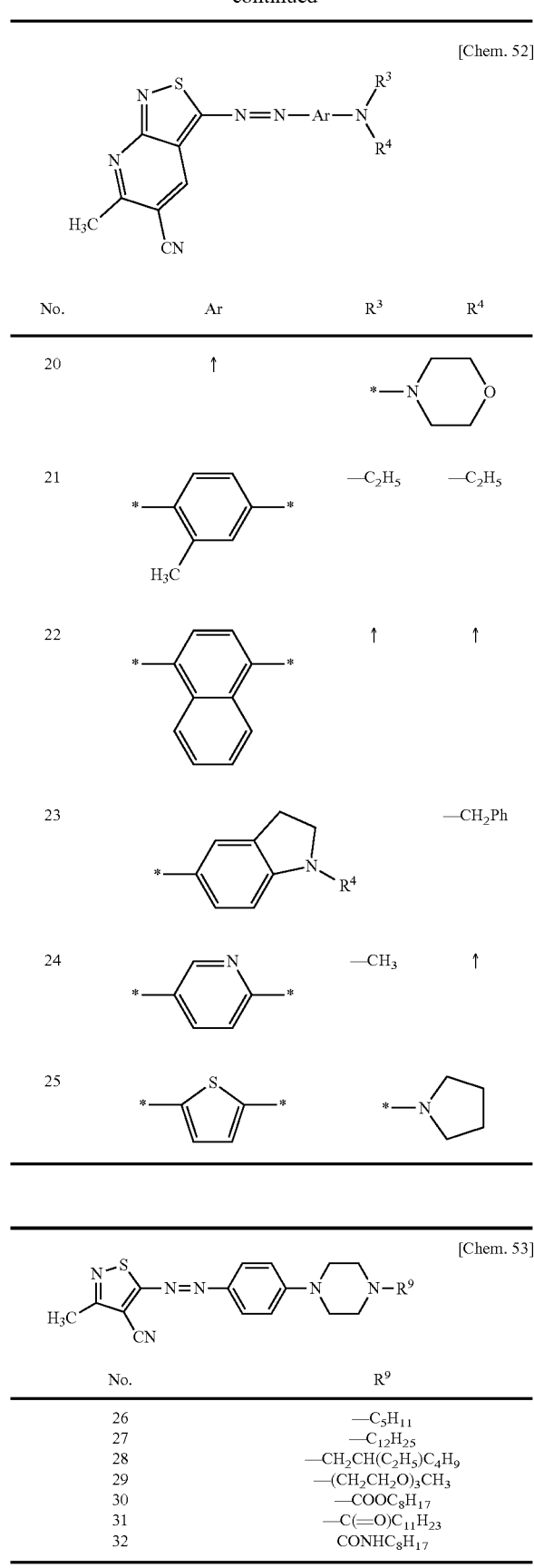

[Chem. 52]

| No. | Ar | R³ | R⁴ |
|---|---|---|---|
| 20 | ↑ | | *-N(morpholine)O |
| 21 | 2-methyl-1,4-phenylene | —C₂H₅ | —C₂H₅ |
| 22 | 1,4-naphthylene | ↑ | ↑ |
| 23 | indolin-5-yl (N-R⁴) | | —CH₂Ph |
| 24 | pyridine-2,5-diyl | —CH₃ | ↑ |
| 25 | thiophene-2,5-diyl | | *-N(pyrrolidine) |

[Chem. 53]

| No. | R⁹ |
|---|---|
| 26 | —C₅H₁₁ |
| 27 | —C₁₂H₂₅ |
| 28 | —CH₂CH(C₂H₅)C₄H₉ |
| 29 | —(CH₂CH₂O)₃CH₃ |
| 30 | —COOC₈H₁₇ |
| 31 | —C(=O)C₁₁H₂₃ |
| 32 | CONHC₈H₁₇ |

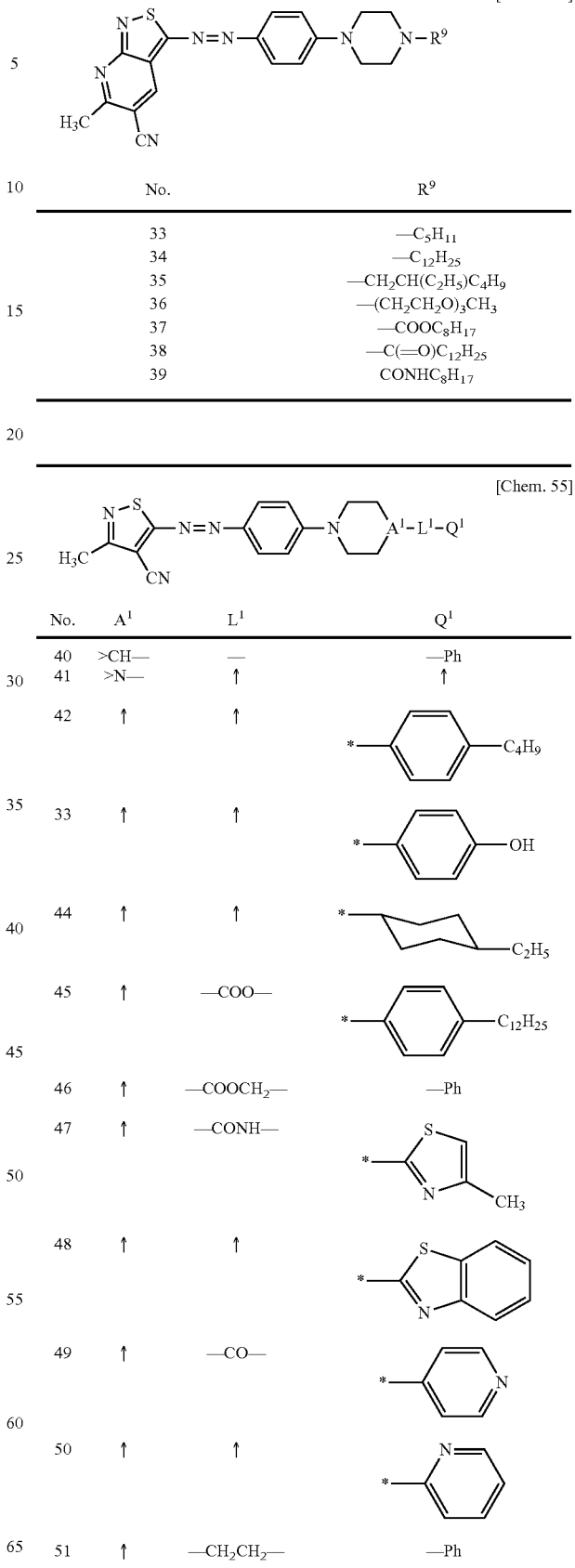

[Chem. 54]

| No. | R⁹ |
|---|---|
| 33 | —C₅H₁₁ |
| 34 | —C₁₂H₂₅ |
| 35 | —CH₂CH(C₂H₅)C₄H₉ |
| 36 | —(CH₂CH₂O)₃CH₃ |
| 37 | —COOC₈H₁₇ |
| 38 | —C(=O)C₁₂H₂₅ |
| 39 | CONHC₈H₁₇ |

[Chem. 55]

| No. | A¹ | L¹ | Q¹ |
|---|---|---|---|
| 40 | >CH— | — | —Ph |
| 41 | >N— | ↑ | ↑ |
| 42 | ↑ | ↑ | *-C₆H₄-C₄H₉ |
| 33 | ↑ | ↑ | *-C₆H₄-OH |
| 44 | ↑ | ↑ | *-cyclohexyl-C₂H₅ |
| 45 | ↑ | —COO— | *-C₆H₄-C₁₂H₂₅ |
| 46 | ↑ | —COOCH₂— | —Ph |
| 47 | ↑ | —CONH— | 4-methylthiazol-2-yl |
| 48 | ↑ | ↑ | benzothiazol-2-yl |
| 49 | ↑ | —CO— | 4-pyridyl |
| 50 | ↑ | ↑ | 2-pyridyl |
| 51 | ↑ | —CH₂CH₂— | —Ph |

[Chem. 55]
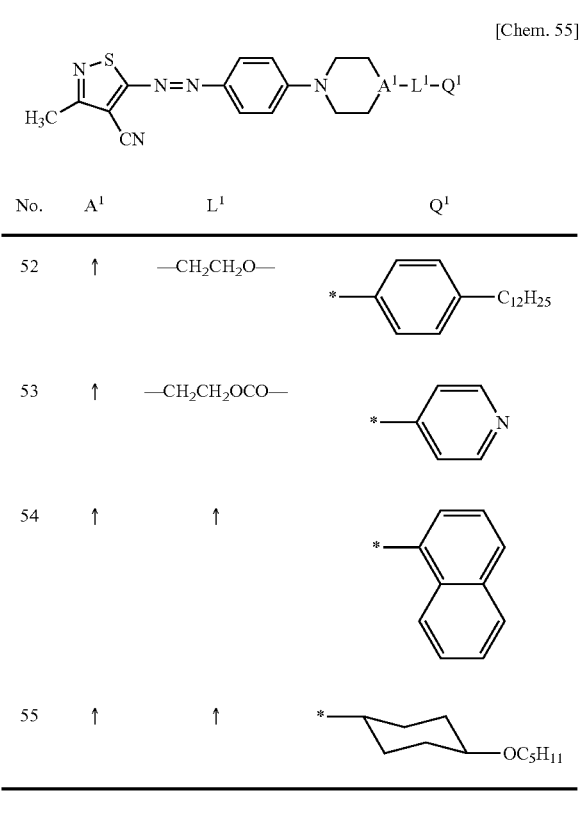
| No. | A¹ | L¹ | Q¹ |
|---|---|---|---|
| 52 | ↑ | —CH₂CH₂O— | *—C₆H₄—C₁₂H₂₅ |
| 53 | ↑ | —CH₂CH₂OCO— | *-4-pyridyl |
| 54 | ↑ | ↑ | *-1-naphthyl |
| 55 | ↑ | ↑ | *-cyclohexyl-OC₅H₁₁ |
[Chem. 56]
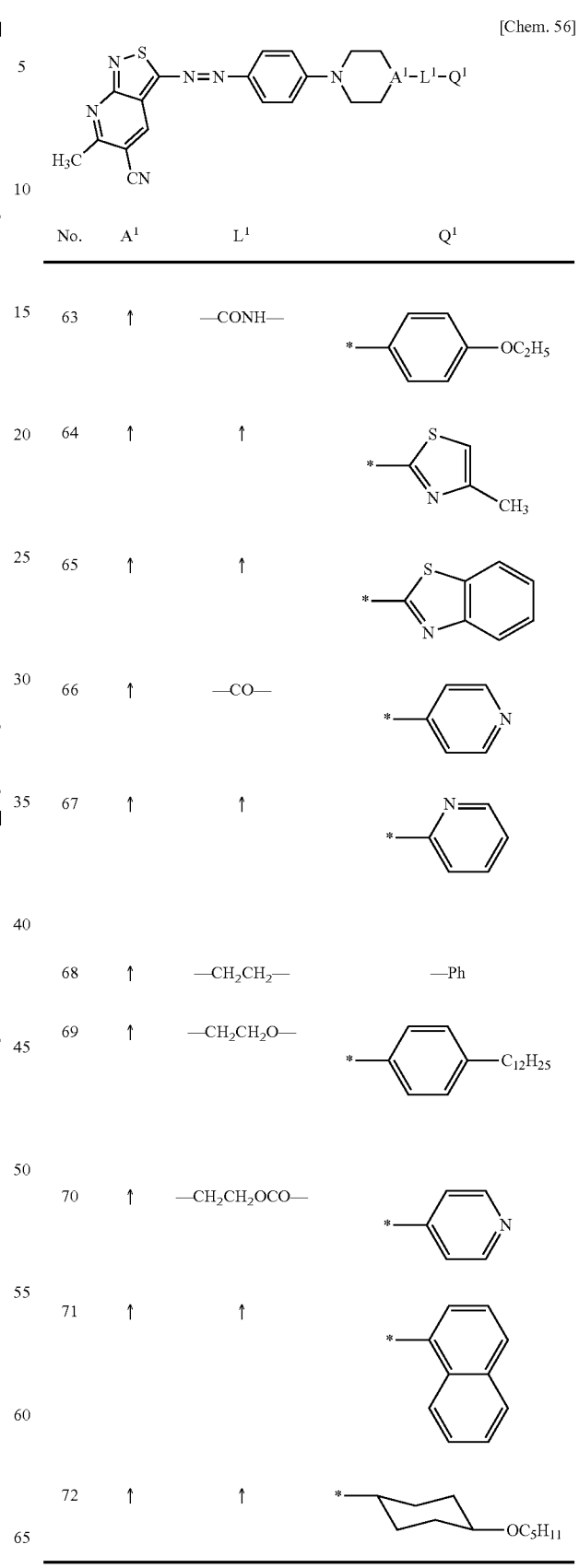
| No. | A¹ | L¹ | Q¹ |
|---|---|---|---|
| 56 | >CH— | — | —Ph |
| 57 | >N— | ↑ | ↑ |
| 58 | ↑ | ↑ | *—C₆H₄—C₄H₉ |
| 59 | ↑ | ↑ | *—C₆H₄—OH |
| 60 | ↑ | ↑ | *-cyclohexyl-C₂H₅ |
| 61 | ↑ | —COO— | *—C₆H₄—C₁₂H₂₅ |
| 62 | ↑ | —COOCH₂— | —Ph |
| 63 | ↑ | —CONH— | *—C₆H₄—OC₂H₅ |
| 64 | ↑ | ↑ | *-thiazol-2-yl-4-CH₃ |
| 65 | ↑ | ↑ | *-benzothiazol-2-yl |
| 66 | ↑ | —CO— | *-4-pyridyl |
| 67 | ↑ | ↑ | *-2-pyridyl |
| 68 | ↑ | —CH₂CH₂— | —Ph |
| 69 | ↑ | —CH₂CH₂O— | *—C₆H₄—C₁₂H₂₅ |
| 70 | ↑ | —CH₂CH₂OCO— | *-4-pyridyl |
| 71 | ↑ | ↑ | *-1-naphthyl |
| 72 | ↑ | ↑ | *-cyclohexyl-OC₅H₁₁ |

[Chem. 57]
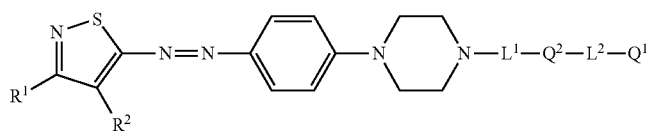
| No. | R¹ | R² | L¹ | Q² | L² | Q¹ |
|---|---|---|---|---|---|---|
| 73 | —CH₃ | —CN | — | *—⌬—* (1,4-phenylene) | — | —Ph |
| 74 | ↑ | ↑ | ↑ | ↑ | ↑ | *—C₆H₄—OC₄H₉ |
| 75 | ↑ | ↑ | ↑ | ↑ | —COO— | *—C₆H₄—CH₃ |
| 76 | ↑ | ↑ | ↑ | ↑ | ↑ | *—C₆H₄—C₁₂H₂₅ |
| 77 | ↑ | ↑ | ↑ | ↑ | ↑ | *—C₆H₄—OCH₃ |
| 78 | ↑ | ↑ | ↑ | ↑ | —COOCH₂— | —Ph |
| 79 | ↑ | ↑ | ↑ | ↑ | —CONH— | *—C₆H₄—OC₂H₅ |
| 80 | ↑ | ↑ | ↑ | ↑ | ↑ | *—C₆H₄—NO₂ |
| 81 | ↑ | ↑ | ↑ | ↑ | ↑ | *—C₆H₄—SO₃H |
| 82 | ↑ | ↑ | ↑ | ↑ | —OCO— | *—C₆H₄—C₄H₉ |
| 83 | ↑ | ↑ | ↑ | ↑ | ↑ | *—(4-pyridyl) |
| 84 | ↑ | ↑ | ↑ | ↑ | —NHCO— | *—C₆H₄—C₄H₉ |
| 85 | ↑ | ↑ | ↑ | *—(cyclohexane-1,4-diyl)—* | —OCO— | *—C₆H₄—C₄H₉ |

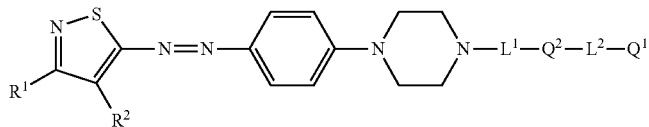
[Chem. 58]
| No. | R¹ | R² | L¹ | Q² | L² | Q¹ |
|---|---|---|---|---|---|---|
| 86 | ↑ | ↑ | —COO— | *-cyclohexyl-* | —OCO— | *-C₆H₄-CH₃ |
| 87 | ↑ | ↑ | ↑ | ↑ | —COO— | *-C₆H₄-C₁₂H₂₅ |
| 88 | ↑ | ↑ | —CO— | *-C₆H₄-* | — | —Ph |
| 89 | ↑ | ↑ | ↑ | *-piperazinyl-* | —COO— | *-C₆H₄-C₁₂H₂₅ |
| 90 | ↑ | ↑ | —CH₂CH₂— | *-C₆H₄-* | —OCO— | *-C₆H₄-C₄H₉ |
| 91 | ↑ | ↑ | ↑ | *-piperazinyl-* | — | —Ph |
| 92 | ↑ | ↑ | ↑ | ↑ | —COO— | *-C₆H₄-C₁₂H₂₅ |
| 93 | ↑ | ↑ | ↑ | ↑ | —CO— | *-C₆H₄-C₄H₉ |
| 94 | ↑ | ↑ | ↑ | *-piperidinyl-* | — | —Ph |
| 95 | ↑ | ↑ | —CH₂CH₂O— | *-cyclohexyl-* | —OCO— | *-C₆H₄-CH₃ |
| 96 | ↑ | ↑ | —CH₂CH₂OCO— | *-piperazinyl-* | —COO— | *-C₆H₄-C₁₂H₂₅ |
| 97 | ↑ | —H | ↑ | *-piperazinyl-* | — | —Ph |
| 98 | —H | ↑ | ↑ | ↑ | ↑ | ↑ |
| 99 | ↑ | —Cl | ↑ | ↑ | ↑ | ↑ |
| 100 | ↑ | —SO₃H | ↑ | ↑ | ↑ | ↑ |
| 101 | ↑ | —NO₂ | ↑ | ↑ | ↑ | ↑ |

[Chem. 59]
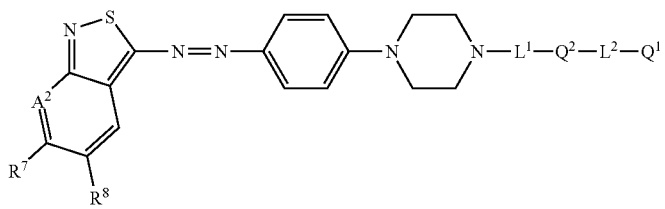
| No. | A² | R⁷ | R⁸ | L¹ | Q² | L² | Q¹ |
|---|---|---|---|---|---|---|---|
| 102 | —N= | —CH₃ | —CN | — | *—C₆H₄—* | — | —Ph |
| 103 | ↑ | ↑ | ↑ | ↑ | ↑ | ↑ | *—C₆H₄—OC₄H₉ |
| 104 | ↑ | ↑ | ↑ | ↑ | ↑ | —COO— | *—C₆H₄—CH₃ |
| 105 | ↑ | ↑ | ↑ | ↑ | ↑ | ↑ | *—C₆H₄—C₁₂H₂₅ |
| 106 | ↑ | ↑ | ↑ | ↑ | ↑ | ↑ | *—C₆H₄—OCH₃ |
| 107 | ↑ | ↑ | ↑ | ↑ | ↑ | —COOCH₂— | —Ph |
| 108 | ↑ | ↑ | ↑ | ↑ | ↑ | —CONH— | *—C₆H₄—OC₂H₅ |
| 109 | ↑ | ↑ | ↑ | ↑ | ↑ | ↑ | *—C₆H₄—NO₂ |
| 110 | ↑ | ↑ | ↑ | ↑ | ↑ | ↑ | *—C₆H₄—SO₃H |
| 111 | ↑ | ↑ | ↑ | ↑ | ↑ | —OCO— | *—C₆H₄—C₄H₉ |
| 112 | ↑ | ↑ | ↑ | ↑ | ↑ | ↑ | *—4-pyridyl |
| 113 | ↑ | ↑ | ↑ | ↑ | ↑ | —NHCO— | *—C₆H₄—C₄H₉ |
| 114 | ↑ | ↑ | ↑ | ↑ | *—C₆H₁₀—* | —OCO— | *—C₆H₄—C₄H₉ |
| 115 | ↑ | ↑ | ↑ | —COO— | *—C₆H₁₀—* | —OCO— | *—C₆H₄—CH₃ |

-continued
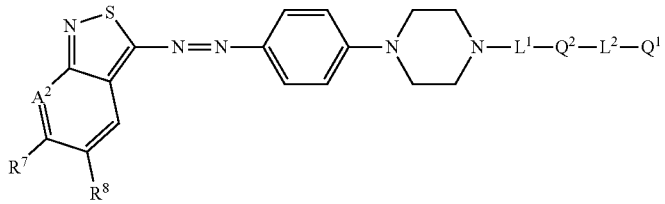
| No. | A² | R⁷ | R⁸ | L¹ | Q² | L² | Q¹ |
|---|---|---|---|---|---|---|---|
| 116 | ↑ | ↑ | ↑ | ↑ | ↑ | —COO— | *—⬡—C₁₂H₂₅ |
| 117 | ↑ | ↑ | ↑ | —CO— | *—⬡—* | — | —Ph |
| 118 | ↑ | ↑ | ↑ | ↑ | *—N⌒N—* | —COO— | *—⬡—C₁₂H₂₅ |
| 119 | ↑ | ↑ | ↑ | —CH₂CH₂— | *—⬡—* | —OCO— | *—⬡—C₄H₉ |
| 120 | ↑ | ↑ | ↑ | ↑ | *—N⌒N—* | — | —Ph |
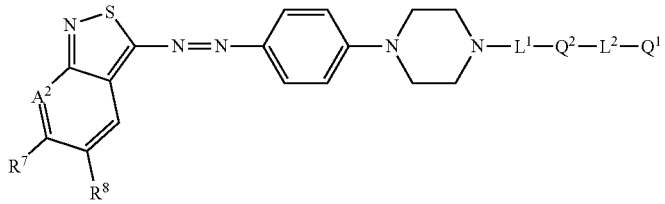
| No. | A² | R⁷ | R⁸ | L¹ | Q² | L² | Q¹ |
|---|---|---|---|---|---|---|---|
| 121 | ↑ | ↑ | ↑ | ↑ | ↑ | —COO— | *—⬡—C₁₂H₂₅ |
| 122 | ↑ | ↑ | ↑ | ↑ | ↑ | —CO— | *—⬡—C₄H₉ |
| 123 | ↑ | ↑ | ↑ | ↑ | *—N⌒—* | — | —Ph |
| 124 | ↑ | ↑ | ↑ | —CH₂CH₂O— | *—⬡—* (cyclohexyl) | —OCO— | *—⬡—CH₃ |

-continued

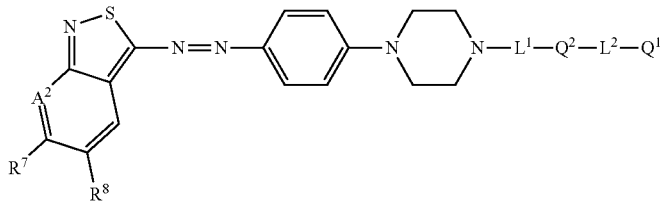

[Chem. 60]

| No. | A² | R⁷ | R⁸ | L¹ | Q² | L² | Q¹ |
|---|---|---|---|---|---|---|---|
| 125 | ↑ | ↑ | ↑ | —CH₂CH₂OCO— | *—N(piperazine)N—* | —COO— | *—C₆H₄—C₁₂H₂₅ |
| 126 | ↑ | ↑ | —H | —CH₂CH₂— | *—N(piperazine)N—* | — | —Ph |
| 127 | ↑ | —H | ↑ | ↑ | ↑ | ↑ | ↑ |
| 128 | ↑ | ↑ | —Cl | ↑ | ↑ | ↑ | ↑ |
| 129 | ↑ | ↑ | —SO₃H | ↑ | ↑ | ↑ | ↑ |
| 130 | ↑ | ↑ | —NO₂ | ↑ | ↑ | ↑ | ↑ |
| 131 | —CH= | —CH₃ | —CN | ↑ | ↑ | ↑ | ↑ |
| 132 | ↑ | ↑ | —H | ↑ | ↑ | ↑ | ↑ |
| 133 | ↑ | —H | ? | ↑ | ↑ | ↑ | ↑ |
| 134 | ↑ | ↑ | —Cl | ↑ | ↑ | ↑ | ↑ |
| 135 | ↑ | ↑ | —SO₃H | ↑ | ↑ | ↑ | ↑ |
| 136 | ↑ | ↑ | —NO₂ | ↑ | ↑ | ↑ | ↑ |

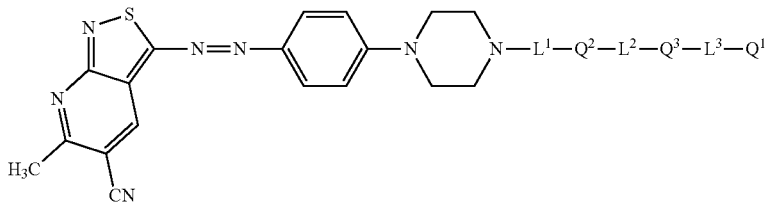

[Chem. 61]

| No. | L¹ | Q² | L² | Q³ | L³ | Q¹ |
|---|---|---|---|---|---|---|
| 137 | — | *—C₆H₄—* | — | *—C₆H₄—* | —COO— | *—C₆H₄—C₁₂H₂₅ |
| 138 | ↑ | ↑ | —COO— | *—C₆H₁₀—* (cyclohexyl) | —OCO— | *—naphthyl |
| 139 | ↑ | ↑ | —OCO— | *—C₆H₄—* | —CONH— | *—thiazolyl—CH₃ |
| 140 | —CH₂CH₂— | *—N(piperazine)N—* | —COO— | *—C₆H₁₀—* (cyclohexyl) | —OCO— | *—C₆H₄—CH₃ |

[Chem. 61]
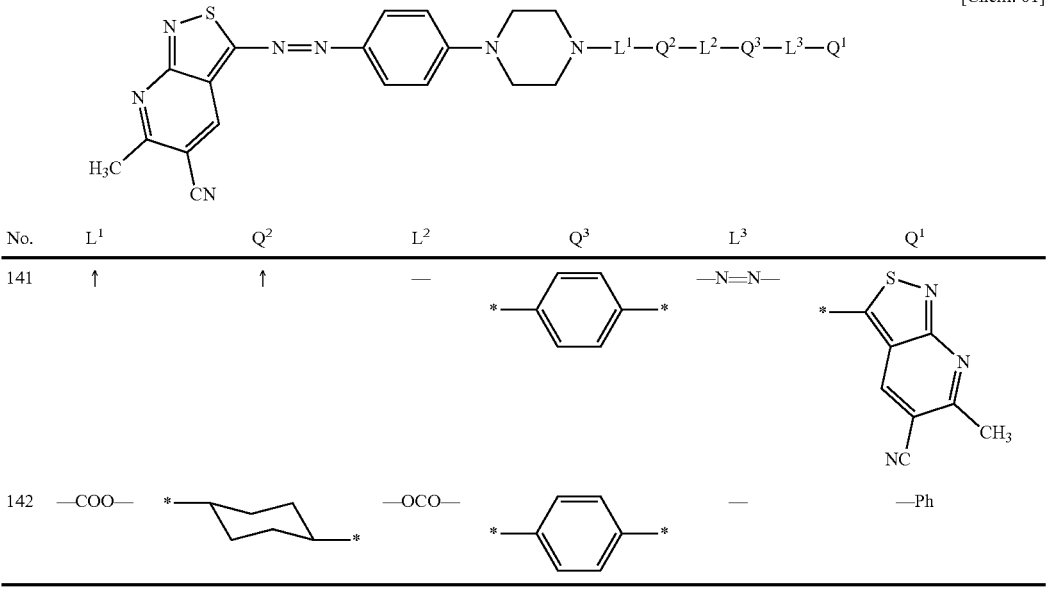
| No. | L¹ | Q² | L² | Q³ | L³ | Q¹ |
|---|---|---|---|---|---|---|
| 141 | ↑ | ↑ | — | *―⟨phenylene⟩―* | —N=N— | *―isothiazolopyridine(CN)(CH₃) |
| 142 | —COO— | *―⟨cyclohexylene⟩―* | —OCO— | *―⟨phenylene⟩―* | — | —Ph |
[Chem. 62]
(143)
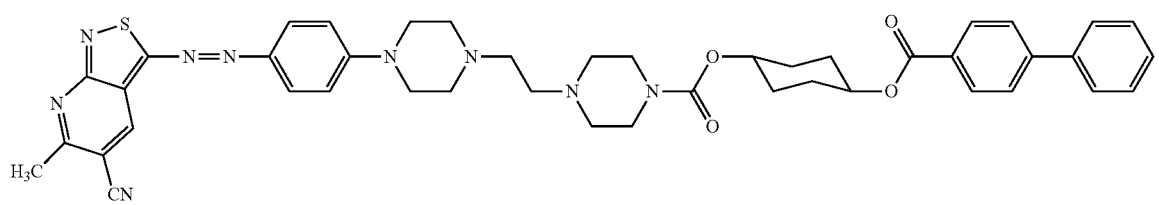
(144)
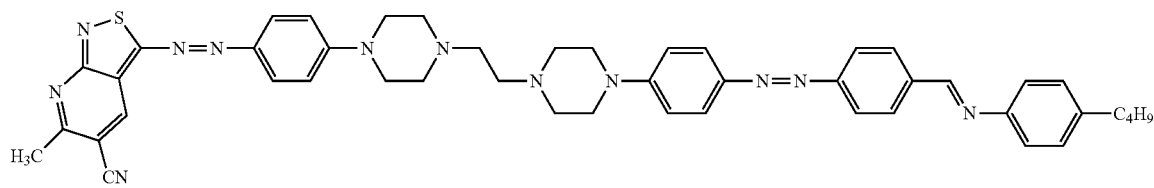
(145)
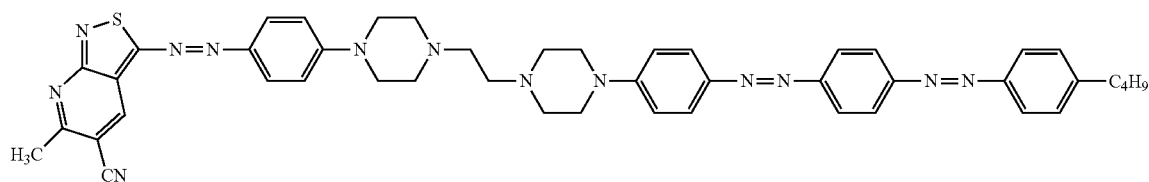
Specific examples of the compound denoted by general formula (XIV) above are given below. However, it is not limited thereto.

[Chem. 63]
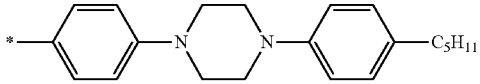
| No. | $R^a$ | $R^b$ | $R^c$ | $R^d$ |
|---|---|---|---|---|
| XIV-1 | H | H | CH₃ | CH₃ |
| XIV-2 | H | H | C₂H₅ | C₂H₅ |
| XIV-3 | H | H | CH₃ | C₂H₅ |
| XIV-4 | OH | H | CH₃ | CH₃ |
| XIV-5 | OH | H | C₂H₅ | C₂H₅ |
| XIV-6 | OH | H | CH₃ | C₂H₅ |
[Chem. 63]
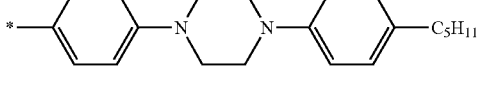
| No. | $R^a$ | $R^b$ | $R^c$ | $R^d$ |
|---|---|---|---|---|
| XIV-7 | OH | OH | CH₃ | CH₃ |
| XIV-8 | OH | OH | C₂H₅ | C₂H₅ |
| XIV-9 | OH | OH | CH₃ | C₂H₅ |
| XIV-10 | OH | CH3 | CH₃ | CH₃ |
[Chem. 64]
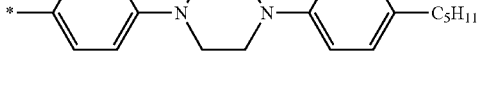
| No. | $R^a$ | $R^b$ | $R^c$ | $A^1$ |
|---|---|---|---|---|
| XIV-11 | H | H | CH₃ | 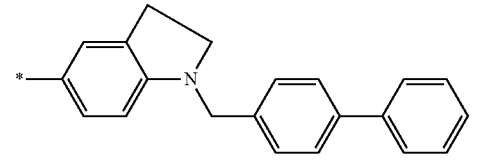 [SMILES: *c1ccc2c(c1)CCN2Cc1ccc(-c2ccccc2)cc1] |
| XIV-12 | H | H | C₂H₅ | 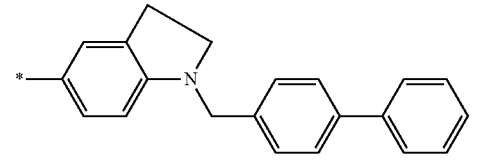 [SMILES: *c1ccc2c(c1)CCN2Cc1ccc(-c2ccccc2)cc1] |
| XIV-13 | OH | H | C₂H₅ | 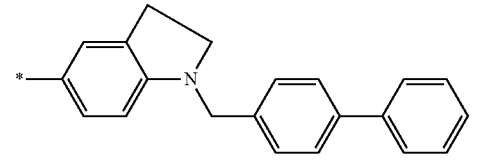 [SMILES: *c1ccc2c(c1)CCN2Cc1ccc(-c2ccccc2)cc1] |
| XIV-14 | OH | H | C₂H₅ | 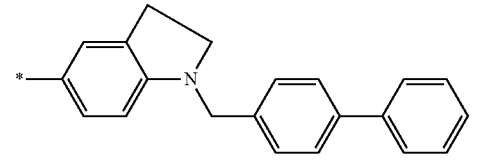 [SMILES: *c1ccc2c(c1)CCN2Cc1ccc(-c2ccccc2)cc1] |
| XIV-15 | OH | H | C₂H₅ | 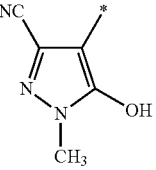 |
| XIV-16 | OH | H | C₂H₅ | 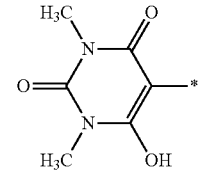 [SMILES: *c1c(O)n(C)c(=O)n(C)c1=O] |

-continued
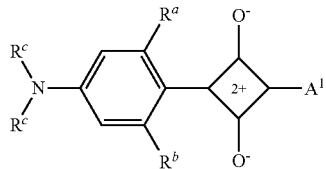
[Chem. 64]
| No. | $R^a$ | $R^b$ | $R^c$ | $A^1$ |
|---|---|---|---|---|
| XIV-17 | OH | H | $C_2H_5$ | (2-methyl-4-methyl-6-hydroxy-7-methyl-pyrazolo[3,4-b]pyridin-3(2H)-one) |
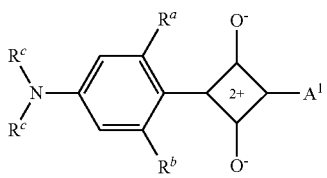
[Chem. 65]
| No. | $R^a$ | $R^b$ | $R^c$ | $A^1$ |
|---|---|---|---|---|
| XIV-18 | OH | H | $C_2H_5$ | (3-cyano-4-methyl-6-hydroxy-1-methyl-pyridin-2(1H)-one) |
| XIV-19 | OH | H | $C_2H_5$ | (1,2-dimethyl-5-hydroxy-pyrazol-3(2H)-one) |
| XIV-20 | OH | H | $C_2H_5$ | (3-cyano-5-hydroxy-isoxazole) |
| XIV-21 | OH | H | $C_2H_5$ | (3-hydroxy-benzo[b]thiophene-1,1-dioxide) |

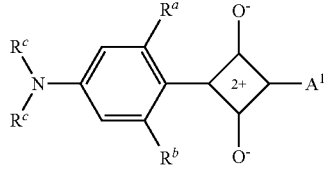

| No. | $R^a$ | $R^b$ | $R^c$ | $A^1$ |
|---|---|---|---|---|
| XIV-22 | OH | H | $C_2H_5$ | |
| XIV-23 | OH | H | $C_2H_5$ | |
| XIV-24 | OH | H | $C_2H_5$ | |
| XIV-25 | H | H | $C_2H_5$ | |
| XIV-26 | H | H | $C_2H_5$ | |

In the liquid-crystal composition set forth above, the proportion accounted for by the compound denoted by general formula (I) in the total solid component excluding solvent is desirably 10% by mass or more, preferably 20% by mass or more. The concentration of the total solid component of the composition is desirably 0.1 to 10% by mass, preferably 0.5 to 5% by mass.

Non-Liquid-Crystal Polyfunctional Monomer Comprising a Radical Polymerizable Group The composition of the present invention desirably comprises a non-liquid-crystal polyfunctional monomer comprising a radical polymerizable group.

In the present invention, the term "non-liquid-crystal polyfunctional monomer comprising a radical polymerizable group" means a polyfunctional monomer, with an actively growing species that undergoes radical polymerization, that is a non-liquid-crystal monomer. The polyfunctional monomer desirably comprises two or more double bonds within the molecule. They are preferably ethylenic (fatty acid) unsaturated double bonds. Specific examples are polyfunctional monomers having functional groups such as alkenes, dienes, acrylates, methacrylates, and unsaturated polyvalent carboxylic acid diesters; amides of α and β-unsaturated carboxylic acids; unsaturated nitriles; methylenes and their derivatives; and vinyl esters and vinyl ethers. The number of double bonds within the molecule is desirably 2 to 20, preferably 2 to 15, and more preferably, 2 to 6. The polyfunctional monomer is desirably the ester of an unsaturated fatty acid and a polyol having two or more hydroxyls in the molecule. Examples of unsaturated fatty acids are acrylic acid, methacrylic acid, maleic acid, and itaconic acid. Acrylic acid and methacrylic acid are desirable. Polyols having four or more hydroxyls within the molecule are desirably either tetrahydric or greater alcohols or oligomers of trihydric or greater alcohols. The oligomer has a molecular structure in which a polyhydric alcohol is linked by an ether bond, ester bond, or urethane bond. An oligomer having a molecular structure in which a polyvalent alcohol is linked by an ether bond is desirable.

The polyfunctional monomer is preferably soluble in organic solvents.

Examples of such monomers are compounds with boiling points at ordinary pressure of 100° C. or higher.

Among polyfunctional monomers, examples of bifunctional (meth)acrylates are ethylene glycol di(meth)acrylate, 1,6-hexanediol di(meth)acrylate, 1,9-nonanediol di(meth)acrylate, polypropylene glycol di(meth)acrylate, tetraethylene glycol di(meth)acrylate, and bisphenoxyethanol fluorene diacrylate. Examples of commercially available products are Aronix M-210, Aronix M-240, and Aronix M-6200 (made by Toagosei Co., Ltd.); Kayarad HDDA, Kayarad HX-220, and Kayarad R-604 (made by Nippon Kayaku Co., Ltd.); and Viscoat 260, Viscoat 312, and Viscoat 335HP (made by Osaka Organic Chemical Industry, Ltd.)

Examples of trifunctional or higher (meth)acrylates are trimethylolpropane tri(meth)acrylate, pentaerythritol tri(meth)acrylate, tri((meth)acryloyloxyethyl)-phosphate, pentaerythritol tetra(meth)acrylate, dipentaerythritol penta(meth)-acrylate, and dipentaerythritol hexa(meth)acrylate. Examples of commercially available products are Aronix M-309, Aronix M-400, Aronix M-405, Aronix M-450, Aronix M-7100, Aronix M-8030, and Aronix M-8060 (all names of products made by Toagosei Co., Ltd.); Kayarad TMPTA, Kayarad DPHA, Kayarad DPCA-20, Kayarad DPCA-30, Kayarad DPCA-60, and Kayarad DPCA-120 (all names of products made by Nippon Kayaku Co., Ltd.); and Viscoat 295, Viscoat 300, Viscoat 360, Viscoat GPT, Viscoat 3PA, and Viscoat 400 (all names of products made by Osaka Organic Chemical Industry, Ltd.).

Further examples of monomers and oligomers are bifunctional or trifunctional and higher (meth)acrylates such as polyethylene glycol di(meth)acrylate, polypropylene glycol di(meth)acrylate, trimethylol ethane triacrylate, trimethylol propane diacrylate, neopentyl glycol di(meth)acrylate, dipentaerythritol penta(meth)acrylate, hexanediol (meth)acrylate, trimethylol propane tri(acryloyloxypropyl)ether, tri(acryloyloxyethyl)isocyanurate, tri(acryloyloxyethyl)cyanurate, glycerine tri(meth)acrylate, tri((meth)acryloyloxyethyl)phosphate, dipentaerythritol penta(meth)acrylate, dipentaerythritol hexa(meth)acrylate; polyfunctional acrylates and polyfunctional methacrylates obtained by (meth)acrylation after adding ethylene oxide or propylene oxide to a polyfunctional alcohol such as trimethylol propane or glycerine; poly(meth)acrylates of polyether polyols; poly(meth)acrylates of polyester polyols; and poly(meth)acrylates of polyurethane polyols.

Monomers comprised of esters of acrylic acid and polyols are commercially available from Mitsubishi Rayon (Ltd.) (product name: Diabeam UK-4154) and Nippon Kayaku Co., Ltd. (product names: Kayarad DPHA, SR355).

These bifunctional or trifunctional and higher (meth)acrylates may be employed singly or in combination. They can also be combined for use with monofunctional (meth)acrylates.

Examples of monofunctional (meth)acrylates are 2-hydroxyethyl (meth)acrylate, carbitol (meth)acrylate, isoboronyl (meth)acrylate, 3-methoxybutyl (meth)acrylate, 2-(meth)acryloyloxyethyl-2-hydroxypropyl phthalate, polyethylene glycol mono(meth)acrylate, polypropylene glycol mono(meth)acrylate, phenoxyethyl (meth)acrylate, and ethylene glycol (meth)acrylate. Examples of commercially available products are Aronix M-101, Aronix M-111, and Aronix M-114 (made by Toagosei Co., Ltd.); Kayarad TC-110S and Kayarad TC-120S (made by Nippon Kayaku Co., Ltd.); and Viscoat 158 and Viscoat 2311 (made by Osaka Organic Chemical Industry, Ltd.).

As set forth further below, when fabricating a polarizer, it is desirable to fix the orientation state of the molecules of the liquid-crystal compound. This fixation is achieved using polymerization to fix the orientation of the dye. Polymerization reactions include thermal polymerization reactions employing thermal polymerization initiators and photopolymerization reactions employing photopolymerization initiators.

In the composition, the total content of the compound of formula (I) and the non-liquid-crystal polymerizable multifunctional monomer in the total solid component excluding solvent is desirably 50% by mass or greater, preferably 70% by mass or greater.

The Polymerization Initiator:

To cause the composition containing the radical polymerizable polyfunctional monomer to undergo a curing reaction, a polymerization initiator is desirably incorporated.

A known polymerization initiator may be suitably employed based on photopolymerization and thermal polymerization. Examples of photopolymerization initiators are α-carbonyl compounds (described in the Specifications of U.S. Pat. Nos. 2,367,661 and 2,367,670), acyloin compounds (described in the Specification of U.S. Pat. No. 2,448,828), α-hydrocarbon substituted aromatic acyloin compounds (described in the Specification of U.S. Pat. No. 2,722,512), polynuclear quinone compounds (described in the Specifications of U.S. Pat. Nos. 3,046,127 and 2,951,758), combinations of triarylimidazole dimers and p-aminophenylketones (described in the Specification of U.S. Pat. No. 3,549,367), acrylidine and phenazine compounds (described in the Specifications of Japanese Unexamined Patent Publication (KOKAI) Showa No. 60-105667 and U.S. Pat. No. 4,239,850), and oxadiazole compounds (described in the Specification of U.S. Pat. No. 4,212,970).

The quantity of photopolymerization initiator employed is desirably 0.01 to 20% by mass, preferably 1 to 10% by mass, of the total solid component excluding solvent.

The description given in paragraphs [0050] and [0051] of Japanese Unexamined Patent Publication (KOKAI) No. 2001-91741 of the quantity of photopolymerization initiator employed and the level of light irradiation energy for polymerization can be applied in the present invention.

Other Additives:

Organic solvents and optional additives can be formulated into and employed in combination in addition to the compound of formula (I) and the non-liquid-crystal polyfunctional monomer, polymerization initiator, and non-liquid-crystal binder polymer that are added as desired in the composition employed in the present invention. Examples of additives are agents preventing unevenness due to air currents, anti-cratering agents, additives for controlling the tilt angle of the alignment film (the tilt angle of the liquid-crystal dye at the interface between the light absorption anisotropic film and the alignment film), additives for controlling the tilt angle at the air interface (the tilt angle of the dye at the interface between the light absorption anisotropic film and the air), sugars, and drugs with the functions of antifungal agents, antibacterial agents, disinfectants, and the like. The various additives will be described below.

Surfactants (Agents Preventing Unevenness Due to Air Currents):

The composition of the present invention can contain surfactants. Surfactants are added with the goal of preventing unevenness due to air currents and the like during coating in the course of preparing the composition as a coating liquid and applying it. Generally, fluorine-based polymers can be suitably employed as surfactants. The fluorine-based polymer that is employed is not specifically limited other than that it not change the tilt angle of the dye or markedly impede orientation. Examples of fluorine-based polymers that can be employed as surfactants are described in Japanese Unexamined Patent Publication (KOKAI) No. 2004-198511, Patent Publication 4190275, Japanese Unexamined Patent Publication (KOKAI) No. 2004-333852, Japanese Unexamined Patent Publication (KOKAI) No. 2005-206638, and Patent Application Publication (TOKUGAN) No. 2008-193565. The combined use of a dye and a fluorine-based polymer permits the displaying of a high-quality image without unevenness. It also enhances coating properties such as cratering. From the perspective of not impeding orientation of the molecules of the liquid-crystal compound, the quantity of surfactant that is added to prevent unevenness due to air currents is generally desirably about 0.1 to 10% by mass, preferably about 0.5 to 10% by mass, and more preferably, about 0.5 to 5% by mass relative to the liquid-crystal compound.

Repelling Inhibitor:

Polymer compounds can be added to the composition of the present invention as materials that prevent repelling during coating. Polymer compounds that are employed to this end are not specifically limited other than that they be compatible with the liquid-crystal compound, not change the tilt angle of the dye, and not markedly impede orientation. Examples of polymers that can be employed as repelling inhibitors are described in Japanese Unexamined Patent Publication (KOKAI) Heisei No. 8-95030. Specific examples of preferred polymers are cellulose esters. Examples of cellulose esters are: cellulose acetate, cellulose acetate propionate, hydroxypropyl cellulose, and cellulose acetate butyrate.

The quantity of the polymer that is added to prevent repelling generally desirably falls within a range of 0.1 to 10% by mass, preferably falls within a range of 0.1 to 8% by mass, and more preferably, falls within a range of 0.1 to 5% by mass, relative to the dichroic dye so as not to impede orientation of the liquid-crystal compound.

Tilt Angle-Controlling Agents of the Alignment Film

Additives that control the tilt angle of the molecules of the liquid-crystal compound on the alignment film side can be added to the composition. Examples of additives having such an effect are compounds comprising both polar groups and nonpolar groups within the molecule. Examples of desirable compounds comprising both polar groups and nonpolar groups within the molecule are $P^0$—OH, $P^0$—COOH, $P^0$—COOH, $P^0$—O—$P^0$, $P^0$—NH$_2$, $P^0$—NH—$P^0$, $P^0$—SH, $P^0$—S—$P^0$, $P^0$—CO—$P^0$, $P^0$—COO—$P^0$, $P^0$—CONH—$P^0$, $P^0$—CONHCO—$P^0$, $P^0$—SO$_3$H, $P^0$—SO$_3$—$P^0$, $P^0$—SO$_2$NH—$P^0$, $P^0$—SO$_2$NHSO$_2$—$P^0$, $P^0$—C=N—$P^0$, HO—P(—O$P^0$)$_2$, (HO—)$_2$PO—O$P^0$, P(—O$P^0$)$_3$, HO—PO(—O$P^0$)$_2$, (HO—)$_2$PO—O$P^0$, PO(—O$P^0$)$_3$, $P^0$—NO$_2$, $P^0$—CN, and organic salts thereof. In addition to organic salts of the above compounds (such as their ammonium salts, carboxylates, and sulfonates), pyridinium salts and the like thereof are also desirably employed. Among compounds having both polar groups and nonpolar groups within the molecule, $P^0$—OH, $P^0$—COOH, $P^0$—O—$P^0$, $P^0$—NH$_2$, $P^0$—SO$_3$H, HO—PO(—O$P^0$)$_2$, (HO—)$_2$PO—O$P^0$, PO(—O$P^0$)$_3$, and organic salts thereof are desirable. Herein, $P^0$ denotes a nonpolar group. When there are multiple instances of $P^0$, they may be identical or different.

Examples of $P^0$ are alkyl groups (desirably linear, branched, or cyclic substituted or unsubstituted alkyl groups having 1 to 30 carbon atoms), alkenyl groups (desirably linear, branched, or cyclic substituted or unsubstituted alkenyl groups having 1 to 30 carbon atoms), alkynyl groups (desirably linear, branched, or cyclic substituted or unsubstituted alkynyl groups having 1 to 30 carbon atoms), aryl groups (desirably substituted or unsubstituted aryl groups having 6 to 30 carbon atoms), and silyl groups (desirably substituted or unsubstituted silyl groups having 3 to 30 carbon atoms). These nonpolar groups may further comprise substituents. Examples of desirable substituents are halogen atoms, alkyl groups (including cycloalkyl groups and bicycloalkyl groups), alkenyl groups (including cycloalkenyl groups and bicycloalkenyl groups), alkynyl groups, aryl groups, heterocyclic groups, cyano groups, hydroxyl group, nitro groups, carboxyl groups, alkoxy groups, aryloxy groups, silyloxy groups, heterocyclic oxy groups, acyloxy groups, carbamoyloxy groups, alkoxycarbonyloxy groups, aryloxycarbonyloxy groups, amino groups (including anilino groups), acylamino groups, aminocarbonylamino groups, alkoxycarbonylamino groups, aryloxycarbonylamino groups, sulfamoylamino groups, alkylsulfonylamino groups, arylsulfonylamino groups, mercapto groups, alkylthio groups, arylthio groups, heterocyclic thio groups, sulfamoyl groups, sulfo groups, alkylsulfinyl groups, arylsufinyl groups, alkoxycarbonyl groups, carbamoyl groups, arylazo groups, heterocyclic azo groups, imido groups, sulfino groups, phosphinyl groups, phosphinyloxy groups, phosphinylamino groups, and silyl groups.

The quantity of the tilt angle-controlling agent of the alignment film is generally desirably about 0.0001% by mass to 30% by mass, preferably about 0.001% by mass to 20% by mass, and more preferably, about 0.005% by mass to 10 weight percent, relative to the weight of the liquid-crystal compound.

The alignment film tilt angle-controlling agent described in Japanese Unexamined Patent Publication (KOKAI) No. 2006-58801 can be employed in the present invention.

The Agent Controlling the Tilt Angle at the Air Interface (Horizontal Orientation Agent):

The composition of the present invention desirably comprises a horizontal orientation agent as an agent controlling the tilt angle at the air interface. The horizontal orientation agent employed in the present invention is desirably:
(1) the fluoroaliphatic group-containing compound denoted by general formula (III) below; or
(2) a fluoroaliphatic group-containing copolymer comprising at least one polymerization unit selected from the group consisting of polymerization units of the fluoroaliphatic group-containing monomer denoted by general formula (IV) or (V) and polymerization units of the amide-group containing monomer denoted by general formula (VI).

These will be individually described below. First (1), the fluoroaliphatic group-containing compound denoted by general formula (III) will be described.

[Chem. 67]

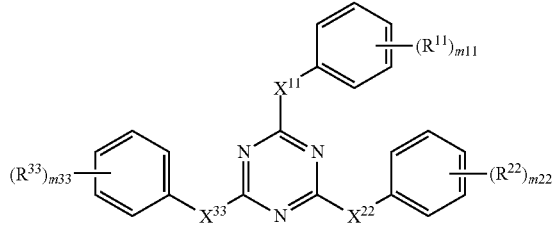

General formula (III)

In the formula, each of $R^{11}$, $R^{22}$, and $R^{33}$ independently denotes an alkoxy group having a terminal $CF_3$ group or $CF_2H$ group. Each of $X^{11}$, $X^{22}$, and $X^{33}$ independently denotes —NH—, —O—, or —S—. Each of m11, m22, and m33 independently denotes an integer of from 1 to 3.

The substituent denoted by each of $R^{11}$, $R^{22}$, and $R^{33}$ is an alkoxy group having a terminal $CF_3$ group or $CF_2H$ group. It can be linear or have a branched chain, desirably has 4 to 20 carbon atoms, preferably has 4 to 16 carbon atoms, and more preferably has 6 to 16 carbon atoms. The alkoxy group having a terminal $CF_3$ group or $CF_2H$ group is an alkoxy group in which some portion or all of the hydrogen atoms in the alkoxy group have been replaced with fluorine atoms. It is desirable for 50% or more, preferable for 60% or more, and even more preferable for 70% or more of the hydrogen atoms in the alkoxy group to have been replaced with fluorine atoms. Examples of alkoxy groups having terminal $CF_3$ group or $CF_2H$ groups denoted by $R^{11}$, $R^{22}$, and $R^{33}$ are given below.

R1: $n\text{-}C_8F_{17}\text{—}O\text{—}$
R2: $n\text{-}C_6F_{13}\text{—}O\text{—}$
R3: $n\text{-}C_4F_9\text{—}O\text{—}$
R4: $n\text{-}C_8F_{17}\text{—}(CH_2)_2\text{—}O\text{—}(CH_2)_2\text{—}O\text{—}$
R5: $n\text{-}C_6F_{13}\text{—}(CH_2)_2\text{—}O\text{—}(CH_2)_2\text{—}O\text{—}$
R6: $n\text{-}C_4F_9\text{—}(CH_2)_2\text{—}O\text{—}(CH_2)_2\text{—}O\text{—}$
R7: $n\text{-}C_8F_{17}\text{—}(CH_2)_3\text{—}O\text{—}$
R8: $n\text{-}C_6F_{13}\text{—}(CH_2)_3\text{—}O\text{—}$
R9: $n\text{-}C_4F_9\text{—}(CH_2)_3\text{—}O\text{—}$
R10: $H\text{—}(CF_2)_8\text{—}O\text{—}$
R11: $H\text{—}(CF_2)_6\text{—}O\text{—}$
R12: $H\text{—}(CF_2)_4\text{—}O\text{—}$
R13: $H\text{—}(CF_2)_8\text{—}(CH_2)\text{—}O\text{—}$
R14: $H\text{—}(CF_2)_6\text{—}(CH_2)\text{—}O\text{—}$
R15: $H\text{—}(CF_2)_4\text{—}(CH_2)\text{—}O\text{—}$
R16: $H\text{—}(CF_2)_8\text{—}(CH_2)\text{—}O\text{—}(CH_2)_2\text{—}O\text{—}$
R17: $H\text{—}(CF_2)_6\text{—}(CH_2)\text{—}O\text{—}(CH_2)_2\text{—}O\text{—}$
R18: $H\text{—}(CF_2)_4\text{—}(CH_2)\text{—}O\text{—}(CH_2)_2\text{—}O\text{—}$ In general formula (III) each of $X^{11}$, $X^{22}$, and $X^{33}$ desirably denotes —NH— or —O— and optimally denotes —NH—. Each of $m^{11}$, $m^{22}$, and $m^{33}$ is desirably 2.

Specific examples of the compound denoted by general formula (III) are given below. However, it is not limited thereto.

Next, (2) the fluoroaliphatic group-containing copolymer comprising at least one polymerization unit selected from the group consisting of polymerization units of the fluoroaliphatic group-containing monomer denoted by general formula (IV) or (V) and polymerization units of the amide-group containing monomer denoted by general formula (VI) will be described.

[Chem. 69]

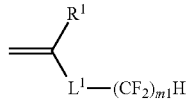

General formula (IV)

In the formula, $R^1$ denotes a hydrogen atom, halogen atom, or methyl group; $L^1$ denotes a divalent linking group; and m1 denotes an integer of from 1 to 18.

[Chem. 70]

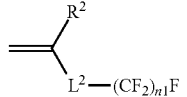

General formula (V)

In the formula, $R^2$ denotes a hydrogen atom, halogen atom, or methyl group; $L^1$ denotes a divalent linking group; and m1 denotes an integer of from 1 to 18.

[Chem. 68]

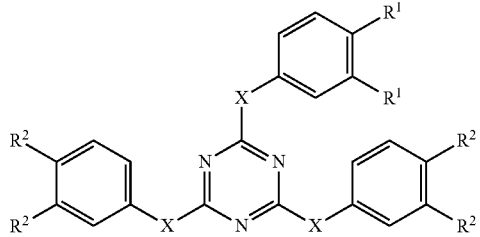

| compound No. | $R^1$ | $R^2$ | X |
|---|---|---|---|
| I-1 | $O(CH_2)_3(CF_2)_4F$ | $O(CH_2)_3(CF_2)_4F$ | NH |
| I-2 | $O(CH_2)_3(CF_2)_6F$ | $O(CH_2)_3(CF_2)_6F$ | NH |
| I-3 | $O(CH_2)_3(CF_2)_8F$ | $O(CH_2)_3(CF_2)_8F$ | NH |
| I-4 | $OCH_2(CF_2)_6H$ | $OCH_2(CF_2)_6H$ | NH |
| I-5 | $OCH_2(CF_2)_8H$ | $OCH_2(CF_2)_8H$ | NH |
| I-6 | $O(CH_2)_2O(CH_2)_2(CF_2)_6F$ | $O(CH_2)_2O(CH_2)_2(CF_2)_6F$ | NH |
| I-7 | $O(CH_2)_2O(CH_2)_2(CF_2)_4F$ | $O(CH_2)_2O(CH_2)_2(CF_2)_4F$ | NH |
| I-8 | $O(CH_2)_3S(CH_2)_2(CF_2)_6F$ | $O(CH_2)_3S(CH_2)_2(CF_2)_6F$ | NH |
| I-9 | $O(CH_2)_3S(CH_2)_2(CF_2)_4F$ | $O(CH_2)_3S(CH_2)_2(CF_2)_4F$ | NH |
| I-10 | $O(CH_2)_6S(CH_2)_2(CF_2)_6F$ | $O(CH_2)_6S(CH_2)_2(CF_2)_6F$ | NH |
| I-11 | $O(CH_2)_6S(CH_2)_2(CF_2)_4F$ | $O(CH_2)_6S(CH_2)_2(CF_2)_4F$ | NH |
| I-12 | $O(CH_2)_2O(CH_2)(CF_2)_6H$ | $O(CH_2)_2O(CH_2)(CF_2)_6H$ | NH |
| I-13 | $O(CH_2)_3(CF_2)_6F$ | $O(CH_2)_3(CF_2)_6F$ | O |
| I-14 | $OCH_2(CF_2)_6H$ | $OCH_2(CF_2)_6H$ | O |
| I-15 | $O(CH_2)_2O(CH_2)_2(CF_2)_6F$ | $O(CH_2)_2O(CH_2)_2(CF_2)_6F$ | O |
| I-16 | $O(CH_2)_3S(CH_2)_2(CF_2)_6F$ | $O(CH_2)_3S(CH_2)_2(CF_2)_6F$ | O |
| I-17 | $O(CH_2)_2O(CH_2)(CF_2)_6H$ | $O(CH_2)_2O(CH_2)(CF_2)_6H$ | O |
| I-18 | $O(CH_2)_3(CF_2)_6F$ | $O(CH_2)_3(CF_2)_6F$ | S |
| I-19 | $OCH_2(CF_2)_6H$ | $OCH_2(CF_2)_6H$ | S |
| I-20 | $O(CH_2)_2O(CH_2)_2(CF_2)_6F$ | $O(CH_2)_2O(CH_2)_2(CF_2)_6F$ | S |
| I-21 | $O(CH_2)_3S(CH_2)_2(CF_2)_6F$ | $O(CH_2)_3S(CH_2)_2(CF_2)_6F$ | S |
| I-22 | $O(CH_2)_2O(CH_2)(CF_2)_6H$ | $O(CH_2)_2O(CH_2)(CF_2)_6H$ | S |

[Chem. 71]

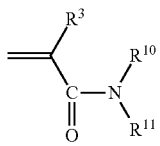

General formula (VI)

In the formula, $R^3$ denotes a halogen atom or methyl group. Each of $R^{10}$ and $R^{11}$ independently denotes a hydrogen atom, alkyl group with 1 to 18 carbon atoms, aromatic group with 6 to 20 carbon atoms, or heterocyclic group with 1 to 20 carbon atoms. $R^{10}$ and $R^{11}$ can also be bonded together to form a hetero ring.

In general formula (IV), $R^1$ denotes a hydrogen atom, halogen atom, or methyl group. A hydrogen atom or methyl group is preferred. $L^1$ denotes a divalent linking group. M1 denotes an integer of from 1 to 18, desirably 2 to 12, preferably 4 to 8, and more preferably, 4 to 6.

In general formula (V), $R^2$ denotes a hydrogen atom, halogen atom, or methyl group. A hydrogen atom or methyl group is preferred. $L^2$ denotes a divalent linking group. n1 denotes an integer of from 1 to 18, preferably 2 to 12, more preferably 4 to 8, and optimally, 4 to 6.

There is no limitation beyond each of $L^1$ and $L^2$ independently denoting a divalent substituent. However, they preferably have the structure denoted by general formula (VII) below. Here, (a) denotes the bonding position on the double bond side and (b) denotes the bonding position on the fluoroaliphatic group side.

$$(a)\text{-}X^{10}\text{—}R^{20}\text{-}(b) \qquad \text{General formula (VII)}$$

In general formula (VII), $X^{16}$ denotes a single bond or a divalent linking group represented by *—COO**, *—COS—**, *—COO—**, *—CON($R^{21}$)—**, or *—O—**. Here, * denotes the bonding position on the double bond side and ** denotes the position of the bond to $R^{20}$.

$R^{20}$ denotes an optionally substituted polymethylene group (such as a methylene group, ethylene group, or trimethylene group), optionally substituted phenylene group (such as an o-phenylene group, m-phenylene group, or p-phenylene group), or a group that can be formed by some combination thereof. Of these, a polymethylene group is preferred. Among polymethylene groups, a methylene group, ethylene group, trimethylene group, or tetramethylene group is desirable, and a methylene group or ethylene group is preferred.

$R^{21}$ denotes a hydrogen atom, an optionally substituted alkyl group with 1 to 8 carbon atoms, or an optionally substituted aryl group with 6 to 20 carbon atoms. A hydrogen atom or an alkyl group with 1 to 6 carbon atoms is preferred, and a hydrogen atom or an alkyl group with 1 to 4 carbon atoms is of greater preference.

The fluoroaliphatic group-containing monomer denoted by general formula (IV) is preferably the monomer denoted by general formula (VIII) below.

[Chem. 72]

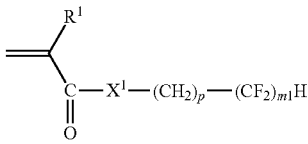

General formula (VIII)

In general formula (VIII), $X^1$ denotes a divalent group represented by —O—, —S—, or —N($R^{222}$)— and p denotes an integer of from 1 to 8. $X^1$ preferably denotes —O— or —N($R^{222}$)—, and optimally denotes —O—. p preferably denotes 1 to 6, and more preferably denotes 1 to 3. $R^1$ and m1 have the same definitions and desirable ranges as set forth for general formula (IV) above. $R^{222}$ denotes a hydrogen atom, an optionally substituted alkyl group with 1 to 8 carbon atoms, or an optionally substituted aryl group with 6 to 20 carbon atoms.

Among fluoroaliphatic group-containing monomers denoted by general formula (V), those denoted by general formula (IX) below are desirable.

[Chem. 73]

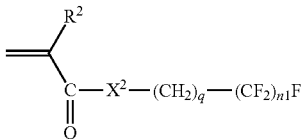

General formula (IX)

In general formula (IX), $X^2$ denotes a divalent group represented by —O—, —S—, or —N($R^{222}$)— and p denotes an integer of from 1 to 8. $X^2$ preferably denotes —O— or —N($R^{222}$)—, and optimally denotes —O—, p preferably denotes 1 to 6, and more preferably denotes 1 to 3. $R^2$ and n1 have the same definitions and desirable ranges as set forth for general formula (V) above. $R^{222}$ is defined as set forth in general formula (VIII).

The polymerization unit of the amide group-containing monomer denoted by general formula (VI) will be described next.

In general formula (VI), $R^3$ denotes a hydrogen atom, halogen atom, or methyl group, preferably a hydrogen atom or a methyl group. Each of $R^{10}$ and $R^{11}$ independently denotes a hydrogen atom, alkyl group with 1 to 18 carbon atoms, aromatic group with 6 to 20 carbon atoms, or heterocyclic group with 1 to 20 carbon atoms. These substituents may further comprise substituents. Further, an alkyl group with 1 to 12 carbon atoms or an aromatic group with 6 to 15 carbon atoms is preferred, and an alkyl group with 1 to 6 carbon atoms or an aromatic group with 6 to 12 carbon atoms is of greater preference. $R^{10}$ and $R^{11}$ may be linked together to form a hetero ring; examples of such a hetero ring are a pyrrolidine ring, piperidine ring, and morpholine ring.

The above fluoroaliphatic group-containing copolymer employed as a horizontal orientation agent contains polymerization units both in the form of a fluoroaliphatic group-containing monomer and an amide group-containing monomer. Two or more types of each of these monomers may be contained as polymerization units. One or more additional copolymerizable types of monomers can be contained as polymerization units in the copolymer. The other types of monomers capable of copolymerization in this fashion that are described in Polymer Handbook 2nd ed., J. Brandrup, Wiley Interscience (1975), Chapter 2, pages 1 to 483 can be employed. An example is a compound having an addition polymerizable unsaturated bond that is selected from among acrylic acid esters, methacrylic acid esters, methacrylamides, allyl compounds, vinyl ethers, vinyl esters, and the like.

The weight average molecular weight of the fluoroaliphatic group-containing copolymer that is employed as a horizontal orientation agent is desirably 2,000 to 100,000, preferably 3,000 to 80,000, and more preferably, 4,000 to 60,000. Here, the weight average molecular weight and molecular weight are those determined by GPC analysis employing TSKgel GMHxL, TSKgel G4000HxL, and TSKgel G2000 HxL (all names of products made by Toso (Ltd.)) columns and by differential refractometry with THF as solvent, and are denoted based on polystyrene conversion.

Examples of the specific structure of fluoroaliphatic group-containing copolymer that can be employed in the present invention as the horizontal orientation agent will be given below. However, it is not limited to the specific examples given below. Numbers in the formulas denote the weight ratios of the various monomer components. Mw denotes weight average molecular weight.

[Chem. 74]

$$-(CH_2-\underset{\underset{O}{\overset{\overset{R^1}{|}}{C}}-O-CH_2-(CF_2)_{m1}H}{C})_x-(CH_2-\underset{\underset{O}{\overset{\overset{R^3}{|}}{C}}-N-R^{11}}{C})_{100-x}-$$

|      | $m^1$ | $R^1$  | $R^3$  | $R^{11}$       | $R^{10}$       | x  | Mw               |
|------|-------|--------|--------|----------------|----------------|----|------------------|
| P-1  | 4     | $CH_3$ | H      | $CH_3$         | $CH_3$         | 60 | $1.9 \times 10^4$ |
| P-2  | 4     | H      | H      | $CH_3$         | $CH_3$         | 80 | $1.4 \times 10^4$ |
| P-3  | 6     | H      | H      | $CH_3$         | $CH_3$         | 70 | $2.8 \times 10^4$ |
| P-4  | 6     | H      | H      | $CH_3$         | $CH_3$         | 80 | $1.6 \times 10^4$ |
| P-5  | 6     | H      | H      | $CH_3$         | $CH_3$         | 90 | $1.8 \times 10^4$ |
| P-6  | 8     | H      | H      | $CH_3$         | $CH_3$         | 75 | $8.2 \times 10^3$ |
| P-7  | 8     | H      | H      | $CH_3$         | $CH_3$         | 95 | $4.6 \times 10^4$ |
| P-8  | 6     | H      | H      | $C_2H_5$       | $C_2H_5$       | 85 | $1.5 \times 10^4$ |
| P-9  | 6     | $CH_3$ | $CH_3$ | $C_4H_9$ (n)   | $C_4H_9$ (n)   | 80 | $1.9 \times 10^4$ |
| P-10 | 6     | H      | H      | $CH_2CH_2OCH_3$| $CH_2CH_2OCH_3$| 90 | $1.2 \times 10^4$ |

[Chem. 75]

$$-(CH_2-\underset{\underset{O}{\overset{\overset{R^1}{|}}{C}}-O-CH_2CH_2-(CF_2)_{n1}F}{C})_x-(CH_2-\underset{\underset{O}{\overset{\overset{R^3}{|}}{C}}-N-R^{11}}{C})_{100-x}-$$

|      | $n^1$ | $R^2$  | $R^3$  | $R^{11}$        | $R^{10}$        | x  | Mw               |
|------|-------|--------|--------|-----------------|-----------------|----|------------------|
| P-11 | 4     | $CH_3$ | H      | $CH_3$          | $CH_3$          | 55 | $8.8 \times 10^3$ |
| P-12 | 4     | H      | H      | $CH_3$          | $CH_3$          | 40 | $1.3 \times 10^4$ |
| P-13 | 6     | H      | H      | $CH_3$          | $CH_3$          | 40 | $1.7 \times 10^4$ |
| P-14 | 6     | H      | H      | $CH_3$          | $CH_3$          | 35 | $2.1 \times 10^4$ |
| P-15 | 6     | H      | H      | $CH_3$          | $CH_3$          | 45 | $9.0 \times 10^3$ |
| P-16 | 8     | H      | H      | $CH_3$          | $CH_3$          | 30 | $1.5 \times 10^4$ |
| P-17 | 6     | H      | H      | $C_2H_5$        | $C_2H_5$        | 40 | $1.5 \times 10^4$ |
| P-18 | 6     | $CH_3$ | $CH_3$ | $C_4H_9$ (n)    | $C_4H_9$ (n)    | 40 | $1.9 \times 10^4$ |
| P-19 | 6     | H      | H      | $CH_2CH_2OCH_3$ | $CH_2CH_2OCH_3$ | 40 | $1.2 \times 10^4$ |
| P-20 | 6     | H      | H      | $CH_2CH_2OH$    | $CH_2CH_2OH$    | 40 | $1.1 \times 10^4$ |

[Chem. 76]

$$-(CH_2-\underset{\underset{O}{\overset{\overset{R^{41}}{|}}{C}}-O-(CH_2)_a-(CF_2)_b-Y}{C})_x-(CH_2-\underset{\underset{O}{\overset{\overset{R^3}{|}}{C}}-N\bigcirc R^{11}}{C})_{100-x}-$$

|      | a | b | Y | $R^{41}$ | $R^3$  | $R^{11}$         | x  | Mw               |
|------|---|---|---|----------|--------|------------------|----|------------------|
| P-21 | 1 | 4 | H | H        | $CH_3$ | $(CH_2)_4$       | 80 | $1.5 \times 10^4$ |
| P-22 | 1 | 6 | H | H        | H      | $(CH_2)_3$       | 85 | $1.3 \times 10^4$ |
| P-23 | 1 | 6 | H | H        | H      | $(CH_2)_2O(CH_2)_2$ | 80 | $1.8 \times 10^4$ |

-continued

[Chem. 76]

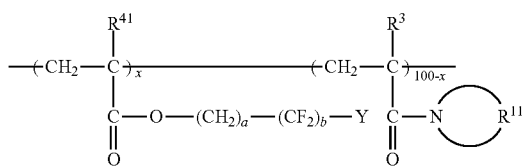

| | a | b | Y | $R^{41}$ | $R^3$ | $R^{11}$ | x | Mw |
|---|---|---|---|---|---|---|---|---|
| P-24 | 2 | 4 | F | H | $CH_3$ | $(CH_2)_4$ | 45 | $1.2 \times 10^4$ |
| P-25 | 2 | 6 | F | H | H | $(CH_2)_5$ | 35 | $1.5 \times 10^4$ |
| P-26 | 2 | 6 | F | H | H | $(CH_2)_2O(CH_2)_2$ | 40 | $2.3 \times 10^4$ |
| P-27 | 3 | 6 | F | H | H | $(CH_3)_6$ | 40 | $1.7 \times 10^4$ |
| P-28 | 6 | 6 | F | $CH_3$ | $CH_3$ | $(CH_2)_2O(CH_2)_2$ | 40 | $1.9 \times 10^4$ |

[Chem. 77]

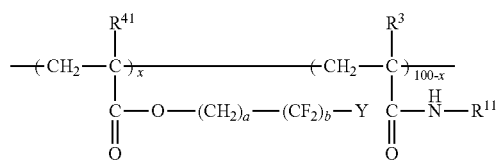

| | a | b | Y | $R^{41}$ | $R^3$ | $R^{11}$ | x | Mw |
|---|---|---|---|---|---|---|---|---|
| P-29 | 1 | 4 | H | H | $CH_3$ | $C_6H_{13}$ (n) | 90 | $2.0 \times 10^4$ |
| P-30 | 1 | 6 | H | H | H | $CH(CH_3)_2$ | 85 | $1.3 \times 10^4$ |
| P-31 | 1 | 6 | H | H | H | CH2CH2Ph | 80 | $1.8 \times 10^4$ |
| P-32 | 2 | 4 | F | H | $CH_3$ | $C_4H_9$ (n) | 45 | $2.7 \times 10^4$ |
| P-33 | 2 | 6 | F | H | H | $CH(CH_3)_2$ | 40 | $1.8 \times 10^4$ |
| P-34 | 2 | 6 | F | H | H | $C(CH_3)_2CH_2COCH_3$ | 35 | $1.8 \times 10^4$ |
| P-35 | 3 | 6 | F | H | H | $CH_2OC_4H_9$ (n) | 40 | $1.7 \times 10^4$ |
| P-36 | 6 | 6 | F | $CH_3$ | $CH_3$ | $C_4H_9$ (t) | 45 | $1.9 \times 10^4$ |

[Chem. 78]

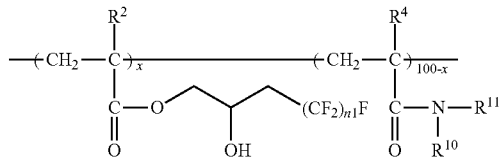

| | $n^1$ | $R^2$ | $R^3$ | $R^{11}$ | $R^{10}$ | x | Mw |
|---|---|---|---|---|---|---|---|
| P-37 | 4 | H | H | $CH_3$ | $CH_3$ | 45 | $1.1 \times 10^4$ |
| P-38 | 4 | H | H | H | $CH(CH_3)_2$ | 40 | $1.3 \times 10^4$ |
| P-39 | 6 | H | H | $CH_3$ | $CH_3$ | 40 | $1.8 \times 10^4$ |
| P-40 | 6 | $CH_3$ | H | $CH_3$ | $CH_3$ | 35 | $2.7 \times 10^4$ |
| P-41 | 6 | H | H | H | $CH(CH_3)_2$ | 40 | $1.4 \times 10^4$ |
| P-42 | 6 | H | H | H | $C(CH_3)_2CH_2COCH_3$ | 40 | $1.9 \times 10^4$ |
| P-43 | 6 | H | H | $(CH_2)_2O(CH_2)_2$ | | 40 | $1.7 \times 10^4$ |
| P-44 | 6 | $CH_3$ | $CH_3$ | $(CH_2)_5$ | | 45 | $1.8 \times 10^4$ |

Note:
P-43 and P-44 are examples in which $R^{10}$ and $R^{11}$ are bonded to form rings.

[Chem. 79]

$$-(CH_2-C(R^2))_x-(CH_2-C(R^3))_{100-x}-$$
with substituents: $C(=O)-O-CH_2CH_2-(CF_2)_cCF(CF_3)_2$ and $C(=O)-N(R^{10})-R^{11}$

| | c | $R^2$ | $R^3$ | $R^{11}$ | $R^{10}$ | x | Mw |
|---|---|---|---|---|---|---|---|
| P-45 | 4 | H | H | $CH_3$ | $CH_3$ | 45 | $3.3 \times 10^4$ |
| P-46 | 4 | H | H | H | $CH(CH_3)_2$ | 40 | $1.5 \times 10^4$ |
| P-47 | 6 | H | H | $CH_3$ | $CH_3$ | 40 | $1.6 \times 10^4$ |
| P-48 | 6 | $CH_3$ | H | H | $CH(CH_3)_2$ | 40 | $2.4 \times 10^4$ |
| P-49 | 6 | H | H | \multicolumn{2}{c}{$(CH_2)_2O(CH_2)_2$} | 40 | $1.7 \times 10^4$ |

Note:
P-49 is an example in which $R^{10}$ and $R^{11}$ are bonded to form a ring.

[Chem. 80]

| | Structure | Mw |
|---|---|---|
| P-50 | $-(CH_2-CH)_{66}-(CH_2-CH)_{15}-(CH_2-CH)_{30}-$ with $C(=O)-O-CH_2(CF_2)_6H$, $C(=O)-O-CH_2CH_2(CF_2)_3F$, $C(=O)-N(CH_3)-CH_3$ | $1.7 \times 10^4$ |
| P-51 | $-(CH_2-CH)_{40}-(CH_2-CH)_{30}-(CH_2-C(CH_3))_{30}-$ with $C(=O)-O-CH_2CH_2(CF_2)_6F$, $C(=O)-N(CH_3)-CH_3$, $C(=O)-O-CH_3$ | $2.0 \times 10^3$ |
| P-52 | $-(CH_2-C(CH_3))_{40}-(CH_2-CH)_{50}-(CH_2-C(CH_3))_{10}-$ with $C(=O)-O-CH_2CH_2(CF_2)_5F$, $C(=O)-N(CH_3)-CH_3$, $C(=O)-O-CH_3$ | $2.5 \times 10^4$ |

In addition, the horizontal orientation agents described in Japanese Unexamined Patent Publication (KOKAI) Nos. 2005-99248, 2005-134884, 2006-126768, and 2006-267183 can also be selected.

One or more of the above horizontal orientation agents can be employed in the present invention. The quantity of the horizontal orientation agent that is added to the composition is desirably 1 to 10% by mass, preferably 0.5 to 10% by mass, and more preferably, 0.5 to 5% by mass, relative to the quantity of liquid-crystal compound added.

Sugars:

Sugars can be added to the composition of the present invention. The addition of sugars enhances the degree of aggregation of the dye aggregate and, as a result, increases the molecular orientation of the dye.

Examples of sugars that can be employed are monosaccharides, disaccharides, polysaccharides, and sugar derivatives such as sugar alcohols. Of these sugars, normally sugars with 2 or more, desirably 3 or more, but not more than 18, and preferably not more than 12 hydroxyl groups can be employed to enhance the effect of the present invention from the perspective of molecular aggregation. An excessive number of hydroxyl groups is undesirable in that it causes the interaction to be excessively strong, resulting in precipitation and loss of orientation in the dye film. An excessively low number is undesirable in that there is insufficient interaction with the dye, precluding improved orientation.

The molecular weight of the sugar employed is desirably 1,000 or less, preferably 700 or less. A sugar of excessively high molecular weight is undesirable in that it causes phase separation with the dye, presenting the risk of loss of orientation in the dye film.

The number of carbon atoms of the sugar employed is normally 36 or less, desirably 24 or less. A sugar with an excessively high number of carbon atoms results in a sugar of excessively high molecular weight which undergoes phase separation with the azo dye and presents a risk of loss of orientation in the dye film.

The sugar employed in the present invention is desirably a monosaccharide, oligosaccharide, or monosaccharide alcohol to satisfy the above optimal hydroxyl number and molecular weight ranges.

Examples of monosaccharides are trehalose, kojibiose, nigerose, maltose, maltotriose, isomaltotriose, maltotetraose, isomaltose, sophorose, laminaribiose, cellobiose, gentiobiose, lactose, sucrose, melibiose, rutinose, primeverose, turanose, panose, isopanose, cellotriose, manninotriose, solatriose, melezitose, planteose, gentianose, umbelliferose, raffinose, and stachyose.

Examples of sugar alcohols are threitol, xylitol, ribitol, arabitol, sorbitol, mannitol, and other compounds obtained by reducing the above monosaccharides and oligosaccharides.

Examples of preferred sugars are xylose, mannose, maltose, maltotriose, and arabitol.

Various optical isomers of these sugars and sugar alcohols exist. Each of these may be employed singly, or both can be incorporated, in the composition of the present invention. Sugars can be employed singly or two or more can be combined for use in the composition of the present invention.

The content of sugar by weight relative to the liquid-crystal compound in the composition of the present invention desirably falls within a range of 0.1 or more and 1 or less, preferably 0.2 or more, more preferably 0.3 or more, still more preferably 0.7 or less, and yet still more preferably, 0.6 or less. When the sugar content falls within this range, it is possible to increase the degree of aggregation with the dye aggregate without lowering the degree of orientation of the aggregate.

Antifungal, Antibacterial, and Disinfectant Agents:

A drug having at least one of the functions of antifungal, antibacterial, and disinfectant agents can be added to the composition employed in the present invention. The addition of these additives enhances the storage stability of the composition.

In the present description, "a drug having at least one of the functions of antifungal, antibacterial, and disinfectant agents" means a drug having at least one of the functions of an antifungal capacity to suppress the generation, growth, or proliferation of a fungus, a disinfectant capacity to kill microorganisms, and an antibacterial capacity to suppress the generation, growth, or proliferation of microorganisms. Known antifungal, disinfectant, and antibacterial agents can be employed. However, they desirably do not compromise the optical characteristics of a polarizer formed from the composition. Examples of drugs having at least one of the functions of antifungal, antibacterial, and disinfectant agents that can be used in the present invention are conventional phenols such as 2,4,4'-trichloro-2'-hydroxydiphenyl, iodine and iodine compounds such as iodine dioxide, and quaternary ammonium salts such as benzalkonium chloride.

Further examples are Proxel BDN, Proxel BD20, Proxel GXL, Proxel LV, Proxel XL, Proxel XL2, and Proxel Ultra10 (all names of products made by Avecia), which contain 1,2-benzisothiazoline-3-one as an active ingredient; Proxel IB (the name of a product made by Avecia), which contains polyhexamethylene biguanide hydrochloride as an active ingredient; and Densil P (the name of a product made by Avecia), which contains dithio-2,2'-bis(benzmethylamide) as an active ingredient.

The following compounds are preferred because they exhibit antibacterial effects in extremely small quantities.

| No. | Compound |
| --- | --- |
| 1. | 2-Chloromethyl-5-chloro-3-isothiazolone |
| 2. | 2-Cyanomethyl-5-chloro-3-isothiazolone |
| 3. | 2-Hydroxymethyl-5-chloro-3-isothiazolone |
| 4. | 2-(3-Methylcyclohexyl)-3-isothiazolone |
| 5. | 2-(4-Chlorophenyl)-4,5-dichloro-3-isothiazolone |
| 6. | 2-(4-Ethylphenyl)-3-isothiazolone |
| 7. | 2-(4-Nitrophenyl)-5-chloro-3-isothiazolone |
| 8. | 2-Chloromethyl-3-isothiazolone |
| 9. | 2-Methoxymethyl-4-methyl-5-chloro-3-isothiazolone |
| 10. | 2-Morpholinomethyl-5-chloro-3-isothiazolone |

These compounds can be synthesized by referring to Japanese Unexamined Patent Publication (KOKAI) Heisei No. 2-278, for example. Commercially available products such as that sold under the name of Tribactran (made by Hoechst) can also be employed.

The drugs having at least one of the functions of antifungal, antibacterial, and disinfectant agents that can be employed in the present invention can be employed singly or in combinations of two or more.

The content of the drugs having at least one of the functions of antifungal, antibacterial, and disinfectant agents in the composition is not specifically limited. Normally, it is 0.01% by mass or more, desirably 0.001% by mass or more. Additionally, it is normally 0.5% by mass or less, desirably 0.3% by mass or less. When the content of the drugs having at least one of the functions of antifungal, antibacterial, and disinfectant agents is kept to within this range, an adequate antifungal, antibacterial, or disinfectant effect can be achieved without drug precipitation, phase separation during film formation, or the like.

Electron-Deficient Discoidal Compounds and Electron-Rich Compounds:

Since the polarizer obtained by the method of the present invention has a high degree of polarization, the composition desirably contains electron-deficient discoidal compounds which lack electrons and electron-rich compounds which have an abundance of electrons. Examples of electron-deficient discoidal compounds and electron-rich compounds that are suitable for use are described in Japanese Unexamined Patent Publication (KOKAI) No. 2006-323377.

The proportion of electron-deficient discoidal compounds in the composition normally falls within a range of 0.1 weight part or more, desirably 0.2 weight part or more, normally 50 weight parts or less, and desirably 40 weight parts or less, per 100 weight parts of the composition as a whole. When the proportion of these compounds is kept within this range, an addition effect is achieved without excessively increasing the viscosity of the solution of the composition.

Further, the proportion of electron-rich compounds in the composition normally falls within a range of 50 weight parts or less, desirably 40 weight parts or less, per 100 weight parts of the composition as a whole. When the proportion of these compounds is kept within this range, an addition effect is achieved without excessively increasing the viscosity of the solution of the composition.

Non-Liquid-Crystal Polymer (Binder Polymer):

The composition can contain a non-liquid-crystal polymer. The non-liquid-crystal polymer can be a polymer that is formed by coating the composition containing a monomer on a substrate or alignment film and then polymerizing the monomer.

Examples of binder polymers that can be added to the composition are polyacrylonitrile, polyacrylic acid ester, polyacrylamide, and other acrylic resins; polystyrene resins; polyvinyl acetal resins such as polyvinylacetoacetal and polyvinyl butyral; ethyl cellulose, hydroxyethyl cellulose, ethylhydroxy cellulose, hydroxypropyl cellulose, ethylhydroxyethyl cellulose, methyl cellulose, cellulose acetate, cellulose acetate butyrate, cellulose acetate propionate, cellulose nitrate, and other modified cellulose resins; nitrocellulose, ethylhydroxyethyl cellulose, ethyl cellulose, and other cellulose resins; polyurethane resin; polyamide resin; polyester resin; polycarbonate resin; phenoxy resin; phenol resin; epoxy resin; and various elastomers. They can be employed singly, mixed, or copolymerized for use.

Acrylic polymers (resins with main chains in the form of acrylic copolymers, styrene copolymers) are preferred as non-liquid-crystal binder polymers; the fact that they are soluble in organic solvents is particularly desirable.

Known radical polymerization methods, for example, can be applied to manufacture acrylic polymers. The polymerization conditions, such as the temperature, pressure, type of radical initiator, quantity thereof, and type of solvent in the course of manufacturing by radical polymerization can be readily established by a person having ordinary skill in the art, and can also be determined by experimentation.

Examples of specific copolymerization components of the above acrylic polymers are: unsaturated carboxylic acids (such as (meth)acrylic acid, crotonic acid, itaconic acid, maleic acid, and fumaric acid), aromatic vinyl compounds (such as styrene, α-methylstyrene, vinyltoluene, 2-vinylpyridine, 4-vinylpyridine, and N-vinylimidazole), (meth)acrylic acid alkyl esters (such as methyl (meth)acrylate, ethyl (meth)acrylate, n-butyl (meth)acrylate, i-butyl (meth)acrylate, hexyl (meth)acrylate, cyclohexyl (meth)acrylate, and dodecyl (meth)acrylate), (meth)acrylic acid alkyl aryl esters (such as benzyl (meth)acrylate), (meth)acrylic acid substituted alkyl esters (such as glycidyl (meth)acrylate and 2-hydroxyethyl (meth)acrylate), carboxylic acid vinyl esters (such as vinyl acetate and vinyl propionate), vinyl cyanides (such as (meth)acrylonitrile and α-chloroacrylonitrile), and aliphatic conjugated dienes (such as 1,3-butadiene and isoprene). Of these, unsaturated carboxylic acids, aromatic vinyl compounds, (meth)acrylic acid alkyl esters, (meth)acrylic acid alkyl aryl esters, and carboxylic acid vinyl esters are desirable. Here, the term "(meth)acrylic acid" is a collective reference to both acrylic acid and methacrylic acid. Similarly, "(meth)acrylate" shall be used to collectively refer to the acrylate and methacrylate below.

Acrylic polymers further comprising a (meth)acryloyl group on a side chain and acrylic graft polymers comprising copolymer components in the form of macromonomers (such as polystyrene macromonomers, polymethyl methacrylate macromonomers, polyethylene glycol mono(meth)acrylate, polypropylene glycol mono(meth)acrylate, and polyethylene glycol polypropylene glycol mono(meth)acrylate) are also desirable.

The content of the non-liquid-crystal polymer in the total solid component excluding solvent in the above composition is desirably 0.5 to 90% by mass, preferably 1 to 80% by mass, and more preferably, 5 to 70% by mass.

The Solvent:

The above composition is desirably prepared as a coating liquid. The solvent employed in the preparation of the coating liquid is desirably an organic solvent. Examples of organic solvents that can be employed are: amides (such as N,N-dimethylformamide), sulfoxides (such as dimethylsulfoxide), heterocyclic compounds (such as pyridine), hydrocarbons (such as benzene, toluene, and hexane), alkyl halides (such as chloroform and dicyclomethane), esters (such as methyl acetate and butyl acetate), ketones (such as acetone and methyl ethyl ketone), and ethers (such as tetrahydrofuran and 1,2-dimethoxyethane). Hydrocarbons, alkyl halides, and ketones are desirable. Two or more organic solvents can be employed in combination.

The method of preparing the coating liquid of the composition is not specifically limited. It is prepared by dissolving one or more liquid-crystal compounds and one or more additives added as desired (such as surfactants and horizontal orientation agents) in a solvent. All of the components in the coating liquid do not have to be completely dissolved. They only need to be uniformly dispersed.

The composition is desirably prepared as a coating liquid in which the concentration of the total solid component is about 0.1 to 10% by mass, preferably about 0.5 to 5% by mass. When a coating liquid with a concentration falling within this range is prepared, it is possible to stably form a polarizing layer by a wet film-forming method.

3. The Light Absorption Anisotropic Film

The present invention further relates to a light absorption anisotropic film (polarizing film) comprising the liquid-crystal composition of the present invention. The laminate that is obtained by forming the light absorption anisotropic film on a substrate can be employed in a liquid-crystal display device as a polarizer. The polarizer is particularly useful as an in-cell polarizer.

An example of a method of manufacturing the light absorption anisotropic film of the present invention is given below.

The composition that has been prepared as a coating liquid is coated on a surface to form a coating. Coating can be conducted by a known, customary method such as spin coating, gravure printing, flexo printing, the ink-jet method, die coating, slit die coating, cap coating, or dipping. Normally, a solution that has been diluted with a solvent is coated, so drying is conducted following application to obtain a coating.

Solutes such as the organic solvent are evaporated from the coating of the composition and the composition is oriented. Natural drying at room temperature is desirable. Care is desirably exercised so as not to disrupt (thermal relaxation and the like are avoided) the oriented state of the azo dye molecules that has been formed by the coating. It is desirable to evaporate off the solvent by processing under reduced pressure and to conduct drying at low temperature.

The "processing under reduced pressure" referred to here means placing the substrate with the coating under conditions of reduced pressure and removing the solvent by evaporation. In this process, the substrate with the coating is desirably maintained horizontal so that there is no flowing from high spots to low spots.

The sooner the coating is processed under reduced pressure following application the better. The period that elapses is desirably one second or more but not more than 30 seconds.

Examples of the method of processing under reduced pressure are given below. The coating that has been obtained by coating the coating liquid is placed along with the substrate in a reduced pressure processing device and processed under reduced pressure. A reduced pressure processing device such as that shown in FIGS. 9 and 10 of Japanese Unexamined Patent Publication (KOKAI) No. 2006-201759 can be employed, for example. The details of the reduced pressure processing device are given in Japanese Unexamined Patent Publication (KOKAI) No. 2004-169975.

The reduced pressure processing conditions are as follows. The pressure within the system in which the coating is present is desirably $2 \times 10^4$ Pa or lower, preferably $1 \times 10^4$ Pa or lower, more preferably $1 \times 10^3$ Pa or lower. It is also desirably 1 Pa or higher, preferably $1 \times 10^1$ Pa or higher. Normally, the pressure that is ultimately reached within the system is desirably as set forth above. When the upper limit is exceeded, there is a risk of disrupting the orientation while precluding drying. When the lower limit is exceeded, drying occurs excessively rapidly, risking the formation of defects.

The reduced-pressure processing time is desirably 5 seconds or more but not more than 180 seconds. When the upper limit is exceeded, the coating cannot dry rapidly before orientation relaxation sets in, risking disruption of orientation. When the lower limit is exceeded, drying is precluded, risking disruption of orientation.

The temperature within the system during processing under reduced pressure is desirably 10° C. or higher and 60° C. or lower. When the upper limit is exceeded, convection occurs during drying, risking the generation of nonuniformity in the coating. When the lower limit is exceeded, drying does not occur, risking disruption of orientation.

When drying the coating and orienting the liquid-crystal composition, heating can be conducted to promote orientation. The temperature is desirably 50° C. or higher and 200° C. or lower, preferably 70° C. or higher and 180° C. or lower. Additives such as plasticizers can be employed in combination with the liquid-crystal composition to lower the orientation temperature.

For example, when the composition is coated on the surface of a photo alignment film, the molecules of one or more liquid-crystal compounds orient at the tilt angle of the alignment film at the interface with the alignment film, and orient with the tilt angle of the air interface at the interface with air. It is desirable for the azo dye to be oriented horizontally at both of the interfaces and for it to be fixed in that state of orientation to manufacture a polarizing layer with a high degree of polarization.

In the present Description, the term "tilt angle" means the angle formed between the long axis direction of the molecules of the azo dye and the interface (alignment film interface or air interface). From the perspective of polarizing performance, the tilt angle on the alignment film side is desirably 0 to 10° C., preferably 0 to 5° C., more preferably 0 to 2° C., and still more preferably, 0 to 1° C. The tilt angle on the air interface side is desirably 0 to 10° C., preferably 0 to 5° C., and more preferably, 0 to 2° C.

To reduce the tilt angle of the molecules of the liquid-crystal compound on the air interface side to within the above range, the composition desirably contains (1) either the fluoroaliphatic group-containing compound denoted by general formula (III), or (2) a fluoroaliphatic group-containing copolymer comprising at least one polymerization unit selected from the group consisting of the polymerization units of the fluoroaliphatic group-containing monomers denoted by general formulas (IV) and (V), and the amide group-containing monomer denoted by general formula (VI). Orienting the molecules of the liquid-crystal compound in the presence of at least one of these reduces the tilt angle on the air interface side to within the stated range.

The tilt angle on the alignment film side tends to be reduced more than the tilt angle on the air interface side due to the effect of the alignment film. However, adding the tilt controlling agent of an alignment film set forth above to the composition further mitigates the tilt angle on the alignment film side, making it possible to achieve a stable horizontal orientation state in the azo dye molecules.

Once the azo dye molecules have been oriented in a desired state in the composition containing the non-liquid-crystal polyfunctional monomer undergoing radical polymerization and curable components such as the polymerization initiator set forth above, it is desirable to conduct polymerization curing by irradiation with light (desirably irradiation with UV radiation), heating, or a combination of the two.

Reference can be made to the description in paragraphs [0050] and [0051] of Japanese Unexamined Patent Publication (KOKAI) No. 2001-91741 for the level of energy of the light that is irradiated for polymerization and the like.

A light absorption anisotropic film (polarizing film) can be formed in the manner set forth above. The thickness of the light absorption anisotropic film is desirably 0.01 to 2 µm, preferably 0.05 to 2 µm.

The Alignment Film:

The use of an alignment film is desirable in the manufacturing of the light absorption anisotropic film of the present invention. The alignment film employed in the present invention can be any sort of layer so long as the molecules of the liquid-crystal azo dye can be oriented to a desired state on the alignment film. It can be provided by a means such as subjecting the surface of a film of an organic compound (desirably a polymer) to a rubbing treatment, vapor deposition of a nonorganic compound at an inclined angle, the formation of a layer with microgrooves, or accumulating an organic compound (such as w-tricosanoic acid, dioctadecylmethyl ammonium chloride, or methyl stearate) by the Langmuir Blodgett method (LB film). Oriented films that perform an orienting function when subjected to an electric field, subjected to a magnetic field, or irradiated with light are also known. Of these, from the perspective of controlling the pretilt angle of the alignment film, the alignment film is desirably formed by a rubbing treatment in the present invention. From the perspective of the uniformity of orientation, a photo alignment film formed by irradiation with light is desirable.

Oriented Films Prepared by Rubbing Treatment

Numerous polymer materials that are employed in alignment films formed by rubbing treatments are described in the literature, and numerous commercial products are available. Polyvinyl alcohols, polyamides, and their derivatives are desirably employed in the alignment film of the present invention. Reference can be made to the description from line 4, page 43, to line 8, page 49 in publication WO 01/88574A1 for alignment films.

The alignment film is desirably 0.01 to 10 µm, preferably 0.01 to 1 µm in thickness, The rubbing treatment can generally be implemented by rubbing the surface of a polymer layer with paper or cloth a number of times in a prescribed direction. In the present invention, it is preferably conducted by the method described in the *Liquid Crystal Handbook* (published by Maruzen on Oct. 30, 2000).

The method described in the *Liquid Crystal Handbook* (published by Maruzen) can be employed to change the rubbing density. The rubbing density (L) is quantified by equation (A) below.

$$L=Nl(1+2\pi rn/60v) \qquad \text{Equation (A)}$$

In the equation, N is the rubbing frequency, l is the contact length of the rubbing roller, r is the radius of the roller, n is the rotational speed of the roller (rpm), and v is the stage displacement rate (per second).

It suffices to increase the rubbing frequency, increase the contact length of the rubbing roller, increase the radius of the roller, increase the rotational speed of the roller, and slow down the stage displacement rate to increase the rubbing density. The reverse suffices to decrease the rubbing density.

The relation between the rubbing density and the pretilt angle of the alignment film is such that increasing the rubbing density reduces the pretilt angle and reducing the rubbing density increases the pretilt angle.

The Photo Alignment Film

Numerous optically orienting materials that can be used in alignment films formed by irradiation with light are described in the literature. Desirable examples for use in the alignment film of the present invention are: the azo compounds described in Japanese Unexamined Patent Publication (KOKAI) Nos. 2006-285197, 2007-76839, 2007-138138, 2007-94071, 2007-121721, 2007-140465, 2007-156439, 2007-133184, and 2009-109831 and U.S. Pat. Nos. 3,883,848 and 4,151,746; the aromatic ester compound described in Japanese Unexamined Patent Publication (KOKAI) No. 2002-229039; the maleimide and/or alkenyl substituted nadimide compounds having optically oriented units described in Japanese Unexamined Patent Publication (KOKAI) Nos. 2002-265541 and 2002-317013; the photocrosslinkable silane derivatives described in U.S. Pat. Nos. 4,205,195 and 4,205,198; and the photocrosslinkable polyimides, polyamides, and esters described in Published Japanese Translation (TOKUHYO) Nos. 2003-520878 and 2004-529220 of PCT International Applications and U.S. Pat. No. 4,162,850. Azo compounds and photocrosslinkable polyimides, polyamides, and esters are preferred.

The photo alignment film formed of the above materials is irradiated with linearly polarized or non-polarized light to manufacture a photo alignment film.

In the present Description, the term "irradiated with linearly polarized light" is an operation to cause the optically oriented material to undergo a photoreaction. The wavelength of the light employed varies with the optically oriented material employed. It is not specifically limited beyond that it be the wavelength that is required for the photoreaction. The peak wavelength of the light that is employed in irradiation with light is desirably 200 to 700 nm. UV light with a peak wavelength of 400 nm or lower is preferably employed.

Examples of the light source that is used to irradiate light are ordinary light sources such as lamps in the form of tungsten lamps, halogen lamps, xenon lamps, xenon flash lamps, mercury lamps, mercury-xenon lamps, and carbon-arc lamps; various lasers (such as semiconductor lasers, helium-neon lasers, argon ion lasers, helium-cadmium lasers, and YAG lasers), light-emitting diodes, and cathode ray tubes.

Means of obtaining linearly polarized light that can be adopted are methods employing polarizing plates (such as iodine polarizing plates, dichroic dye polarizing plates, wire grid polarizing plates); methods employing prism elements (such as Glan-Thompson prisms) and reflective polarizers utilizing Brewster's angle; and methods employing light emitted by a polarized laser beam source. It is also possible to employ filters, wavelength-converting elements, and the like to selectively radiate just light of the required wavelength.

When irradiating linearly polarized light, the method is adopted of irradiating light vertically or diagonally onto the surface of the alignment film from the front or rear surface relative to the alignment film. The angle of incidence of the light varies with the optically oriented material. By way of example, it is 0 to 90° C. (perpendicular), desirably 40 to 90° C.

When non-polarized light is employed, the non-polarized light is irradiated diagonally. The angle of incidence is 10 to 80°, desirably 20 to 60°, and preferably, 30 to 50°.

The period of irradiation is desirably 1 to 60 minutes, preferably 1 to 10 minutes.

When patterning is required, the method of irradiating light a necessary number of times to form patterns using a photomask or the method of writing a pattern by scanning with a laser beam can be adopted.

The thickness of the light absorption anisotropic film of the present invention formed of the composition set forth above is desirably 0.01 to 2 μm, preferably 0.05 to 2 μm.

Generally, as a characteristic required of a polarizing film, it is considered desirable for the transmitted light to achieve $0.28<x<0.36$ and $0.28<y<0.36$ in the xy chromaticity diagram when a C light source is employed as light source. The light absorption anisotropic film of the present invention that is fabricated using the compound of formula (I) above satisfies this characteristic and is useful as a polarizing film. There are detailed descriptions of C light sources, the xy chromaticity diagram, and how to calculate x and y in *JIS Handbook [61] Color* released by the Japanese Standards Association. Reference can be made thereto.

The light absorption anisotropic film can also be formed on a substrate. The substrates that can be used in the present invention can be selected based on the application of the light absorption anisotropic film. Examples are the non-alkali glass, soda glass, Pyrex (registered trademark) glass, and quartz glass that are employed in liquid-crystal display elements, OLED elements, and the like; the photoelectric conversion element substrates that are employed in fixed image pickup elements and the like; silicon substrates; plastic substrates; and substrates comprised of these materials on which functional layers have been formed such as transparent conductive films, color filter films, electrodes, and TFTs. A black matrix separating each picture element, or a transparent resin layer to enhance adhesion or the like can be provided on these substrates. It is also desirable for a gas barrier layer and/or a solvent-resistant layer to be present on the surface of a plastic substrate.

The light transmittance of the above substrate is desirably 80% or higher. The use of an optically isotropic polymer film as a plastic substrate is desirable. The description of detailed examples and desirable forms of the polymer that is given in paragraph [0013] of Japanese Unexamined Patent Publication (KOKAI) No. 2002-22942 can be applied. Even polymers tending to exhibit birefringence, such as conventionally known polycarbonates and polysulfones, can be employed by reducing this tendency by means of the molecular modification described in International Publication WO 00/26705.

Other Functional Layers:

An alignment film can be present between the substrate and the light absorption anisotropic film. Examples of the alignment film, materials used to form it, and methods of formation are all as set forth above.

Further, a color filter layer can be present between the substrate and the light absorption anisotropic film. In addition to a color filter layer, functional layers such as a transparent conductive film, a color filter film, an electrode, and a TFT can also be present. A black matrix separating individual picture elements can also be formed.

A transparent cured resin layer can be present on the light absorption anisotropic film. The materials and methods used to form the transparent cured resin layer are as set forth above.

4. The Display Device

The present invention further relates to a display device, such as a liquid-crystal display device, that is equipped with at least one light absorption anisotropic film (polarizing film) in accordance with the present invention. The configuration and the like thereof is not specifically limited. Specific examples are transmitting, reflecting, and semi-transmitting liquid-crystal display devices, OLEDs, and the like of various modes such as TN, STN, VA, ECB, IPS, and OCB. A display device in which the light absorption anisotropic film of the present invention is positioned on the inner surface side of the substrate as a so-called "in-cell polarizer" is preferred. And a display device in which the light absorption anisotropic film of the present invention is laminated on a color filter substrate is of even greater preference. Such a configuration diminishes the reduction in contrast due to scattered light caused by depolarization by the color filter layer.

EMBODIMENTS

The characteristics of the present invention are described with greater specificity below through embodiments and comparative examples. The materials, quantities employed, proportions, processing contents, processing procedures, and the like that are set forth in the embodiments can be suitably modified without departing from the scope or spirit of the present invention. Accordingly, the scope of the present invention is not to be interpreted as being limited by the specific examples given below.

Synthesis Example 1

Synthesis examples of the compound of the present invention are set forth below. However, additional dyes can also be synthesized by the same methods. Herein, "parts" refer to parts by weight. In the schemes shown, Me denotes a methyl group, Et denotes an ethyl group, and Ac denotes an acetyl group. In the following synthesis examples, the measurements relating to various properties were conducted as follows.

<Maximum Absorption Wavelength>

The maximum absorption wavelength of the dye in N-methylpyrrolidone solvent was measured with a UV-2550 spectrophotometer (made by Shimadzu Corp.).

<Phase Transition Temperature>

The phase transition temperature was determined by thermal analysis with a DSC measurement apparatus (made by Seiko Instruments) and by visual observation with a polarizing microscope.

Synthesis Example 1

Example of Synthesis of Exemplary Compound A-4

Exemplary Compound A-4 was synthesized by the following synthesis scheme.

[Chem. 81]

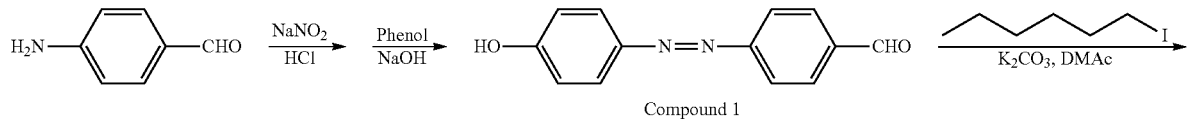

Compound 1

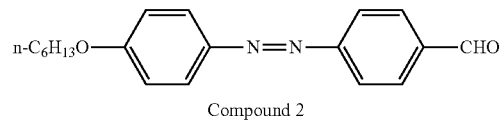

Compound 2

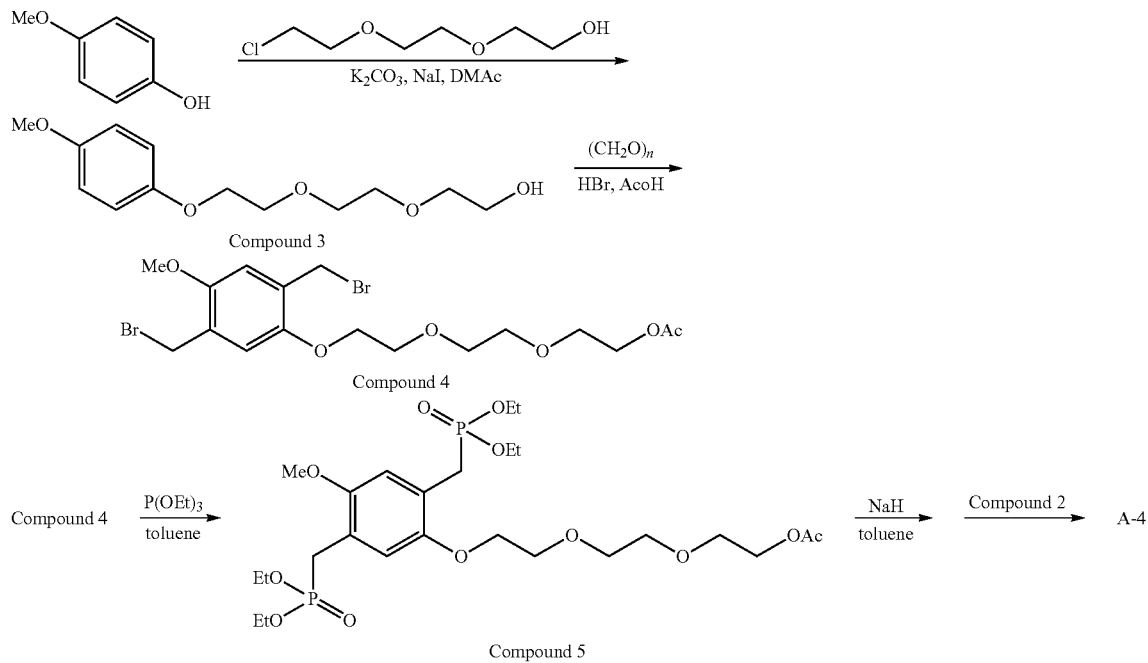

In 170 mL of 3.5 N aqueous hydrochloric acid were dissolved 24.2 parts of 4-aminobenzaldehyde and the solution was cooled with ice to 0° C. To this was added dropwise a solution of 15.2 parts of sodium nitrite in 40 mL of water while maintaining a temperature of 5° C. The mixture was stirred for about an hour while maintaining the temperature. The production of diazonium salt was confirmed, after which 1.94 parts of amidosulfuric acid were added and an aqueous solution of diazonium salt was prepared. In 200 mL of an aqueous solution of 1.9 N sodium hydroxide were dissolved 18.8 parts of phenol and the mixture was cooled to 0° C. with ice. To this was added dropwise the diazonium aqueous solution while maintaining a temperature of 25° C. or lower.

Stirring was conducted for a while at room temperature, after which the product that precipitated out was filtered, washed with water, and dried. Following drying, 33.4 parts of Compound 1 were obtained.

In 50 mL of dimethylacetamide were dissolved 11.3 parts of Compound 1 and 13.8 parts of potassium carbonate. To this were added 12.7 parts of 1-iodo-n-hexane and the mixture was stirred for 1 hour at 70° C. After confirming that the reaction had ended, the mixture was returned to room temperature and 100 mL of water was added. The product that precipitated out was filtered, washed with water, and dried. Following drying, 13.5 parts of Compound 2 were obtained.

In 50 mL of dimethylacetamide were dissolved 12.4 parts of 4-methoxyphenol, 41.5 parts of potassium carbonate, and 16.5 parts of sodium iodide. To this were added 18.5 parts of triethylene glycol monochlorohydrin and the mixture was stirred for an hour at 70° C. After confirming that the reaction had ended, the mixture was returned to room temperature, 150 mL of water was added, and the mixture was extracted with 150 mL of ethyl acetate. The product was dried with sodium sulfate, concentrated, and isolated and purified by column chromatography, yielding 21.5 parts of Compound 3.

In 34 mL of acetic acid were dissolved 8.65 parts of Compound 3 and 3.04 parts of paraformaldehyde. To this was added dropwise 17.7 mL of a 33% acetic acid solution of hydrogen bromide and the mixture was stirred for 3 hours at 50° C. Water was added. The product that precipitated was filtered and then isolated and purified by column chromatography, yielding 9.66 parts of Compound 4.

In 48 mL of toluene were dissolved 4.85 parts of Compound 4. To this was added 4.29 mL of triethyl phosphite and the mixture was stirred for 5 hours with refluxing. After confirming that the reaction had ended, the toluene was distilled off, yielding Compound 5 in the form of a crude product.

In 5 mL of toluene was dissolved in 0.19 part of oily sodium hydride (50 to 72% content). To this was added dropwise a solution of 1.20 parts of compound 5 (crude product) dissolved in 5 mL of toluene under a nitrogen atmosphere. Bubbling of the hydrogen was confirmed, after which a solution of 1.24 parts of Compound 2 in 5 mL of toluene was added dropwise and the mixture was stirred for an hour at 50° C. The mixture was cooled to room temperature, after which 20 mL of methanol was added. The product that precipitated was filtered, washed with methanol, and dried. Following drying, 1.04 parts of Exemplary Compound A-4 were obtained.

The λmax of Exemplary Compound A-4 in N-methylpyrrolidone solvent was 463.8 nm.

The details of $^1$H-NMR (CDCl$_3$) of Exemplary Compound A-4 were: 7.90 (t, 8H), 7.68 (d, 4H), 7.60 (m, 2H), 7.20 (m, 4H), 7.00 (d, 4H), 4.28 (t, 2H), 4.14 (t, 4H), 3.95 (m, 5H), 3.80 (m, 2H), 3.73 (m, 4H), 3.61 (m, 2H), 2.32 (s, 1H), 1.72 (m, 4H), 1.49 (m, 4H), 1.35 (m, 8H), 0.93 (t, 6H).

Exemplary Compound A-4 had liquid crystallinity; nematic liquid crystallinity was confirmed at a range of 133 to 299° C. Observation under a polarizing microscope revealed that it was a dichroic dye.

Synthesis Example 2

With the exception that the triethylene glycol monochlorohydrin in Synthesis Example 1 was changed to triethylene glycol monochloromonomethyl ether, Exemplary Compound A-3 was synthesized by the same method as in Synthesis Example 1.

The λmax of Exemplary Compound A-3 in N-methylpyrrolidone solvent was 463.3 nm.

The details of $^1$H-NMR (CDCl$_3$) of Exemplary Compound A-3 were: 7.91 (t, 8H), 7.69 (d, 4H), 7.60 (m, 2H), 7.20 (m, 4H), 7.00 (d, 4H), 4.28 (t, 2H), 4.14 (t, 4H), 3.95 (m, 5H), 3.80 (m, 2H), 3.73 (m, 2H), 3.65 (m, 2H), 3.55 (m, 2H), 3.32 (s, 3H), 1.72 (m, 4H), 1.49 (m, 4H), 1.35 (m, 8H), 0.93 (t, 6H).

Exemplary Compound A-3 had liquid crystallinity; nematic liquid crystallinity was confirmed at a range of 138 to 284° C. Observation under a polarizing microscope revealed that it was a dichroic dye.

Synthesis Example 3

With the exception that the triethylene glycol monochlorohydrin in Synthesis Example 1 was changed to 1-iodo-n-octadecane, Exemplary Compound A-9 was synthesized by the same method as in Synthesis Example 1.

The λmax of Exemplary Compound A-9 in N-methylpyrrolidone solvent was 460.0 nm.

The details of $^1$H-NMR (CDCl$_3$) of Exemplary Compound A-9 were: 7.91 (t, 8H), 7.69 (d, 4H), 7.60 (m, 2H), 7.20 (m, 4H), 7.00 (d, 4H), 4.08 (m, 6H), 4.00 (s, 3H), 1.80 (m, 6H), 1.52 (m, 6H), 1.40 (m, 14H), 1.25, (m, 22H), 0.93 (t, 9H).

Exemplary Compound A-9 had liquid crystallinity; nematic liquid crystallinity was confirmed at a range of 148 to 212° C. Observation under a polarizing microscope revealed that it was a dichroic dye.

Synthesis Example 4

With the exception that the 4-methoxyphenol in Synthesis Example 1 was changed to hydroquinone, Exemplary Compound A-10 was synthesized by the same method as in Synthesis Example 1.

The λmax of Exemplary Compound A-10 in N-methylpyrrolidone solvent was 457.5 nm.

The details of $^1$H-NMR (CDCl$_3$) of Exemplary Compound A-10 were: 7.90 (t, 8H), 7.65 (d, 4H), 7.58 (d, 2H), 7.20 (m, 4H), 7.00 (d, 4H), 4.28, (t, 4H), 4.05 (t, 4H), 3.95 (t, 4H), 3.80 (t, 4H), 3.71 (t, 4H), 3.64 (t, 4H), 3.52 (t, 4H), 3.33 (s, 6H), 1.71 (m, 4H), 1.49 (m, 4H), 1.34 (m, 8H), 0.91 (t, 6H).

Exemplary Compound A-10 had liquid crystallinity; nematic liquid crystallinity was confirmed at a range of 110 to 201° C. Observation under a polarizing microscope revealed that it was a dichroic dye.

Synthesis Example 5

In 20 mL of tetrahydrofuran were dissolved 1.00 part of Exemplary Compound A-4 and 0.76 part of pyridine. The solution was cooled to 0° C., after which 0.89 part of acryloyl chloride was added dropwise. The reaction solution was stirred for 3 hours at room temperature, after which 20 mL of acetonitrile was added dropwise. The product that precipitated was filtered, washed with acetonitrile, and dried. Following drying, 0.86 part of Exemplary Compound A-6 was obtained.

The λmax of Exemplary Compound A-6 in N-methylpyrrolidone solvent was 460.6 nm.

The details of $^1$H-NMR (CDCl$_3$) of Exemplary Compound A-6 were: 7.90 (t, 8H), 7.68 (d, 4H), 7.58 (m, 2H), 7.20 (m, 4H), 7.00 (d, 4H), 6.59 (d, 1H), 6.10 (d, 1H), 5.78 (d, 1H), 4.29 (m, 4H), 4.05 (t, 4H), 3.95 (m, 5H), 3.75 (m, 6H), 1.80 (m, 4H), 1.49 (m, 4H), 1.34 (m, 8H), 0.91 (t, 6H).

Exemplary Compound A-6 had liquid crystallinity; nematic liquid crystallinity was confirmed at a range of 113 to 275° C. Observation under a polarizing microscope revealed that it was a dichroic dye.

Synthesis Example 6

In 20 mL of toluene was dissolved 1.00 part of Exemplary Compound A-4, after which 0.63 part of succinic anhydride was added. The mixture was then stirred for 2 hours with refluxing. The reaction solution cooled to room temperature. The product that precipitated was filtered, washed with methanol, and dried. Following drying, 0.91 part of Exemplary Compound A-7 was obtained.

The λmax of Exemplary Compound A-7 in N-methylpyrrolidone solvent was 460.2 nm.

The details of $^1$H-NMR (CDCl$_3$) of Exemplary Compound A-7 were: 7.90 (t, 8H), 7.68 (d, 4H), 7.58 (m, 2H), 7.20 (m, 4H), 7.00 (d, 4H), 4.28 (m, 4H), 4.03 (t, 4H), 3.97 (m, 5H), 3.81 (m, 2H), 3.69 (m, 5H), 2.60 (m, 6H), 1.81 (m, 4H), 1.49 (m, 4H), 1.34 (m, 8H), 0.91 (t, 6H).

Exemplary Compound A-7 had liquid crystallinity; nematic liquid crystallinity was confirmed at a range of 135 to 270° C. Observation under a polarizing microscope revealed that it was a dichroic dye.

Synthesis Example 7

With the exception that the 4-methoxyphenol in Synthesis Example 1 was changed to dimethylhydroquinone, Exemplary Compound A-34 was synthesized by the same method as in Synthesis Example 1.

The λmax of Exemplary Compound A-34 in N-methylpyrrolidone solvent was 463.4 nm.

The details of $^1$H-NMR (CDCl$_3$) of Exemplary Compound A-34 were: 7.90 (t, 8H), 7.64 (d, 4H), 7.58 (d, 2H), 7.18 (m, 4H), 7.02 (d, 4H), 4.07 (t, 4H), 3.90 (s, 6H), 1.73 (m, 4H), 1.49 (m, 4H), 1.33 (m, 8H), 0.90 (t, 6H).
[Two Redundant Lines from [0243] Omitted]

Exemplary Compound A-34 had liquid crystallinity; nematic liquid crystallinity was confirmed at 247° C. and above. It exhibited liquid crystallinity even at the heating limit of 300° C.
Observation under a polarizing microscope revealed that it was a dichroic dye.

Based on the above results, all of the compounds of formula (I) that were synthesized in Synthesis Examples 1 to 7 exhibited nematic crystallinity and were found to be dichroic dyes.

The solubility of these compounds in chloroform was measured. The solubility in chloroform of a comparison dichroic azo dye in the form of Comparative Compound 1 below, which had a symmetric polyazo skeleton, was also measured. Comparison Compound 1, recorded below, is an azo dichroic dye that exhibits nematic liquid crystallinity at 220° C. and above.

In contrast to Comparative Compound 1, which had almost no solubility in chloroform, Exemplary Compounds A-4, A-3, A-10, A-6, and A-7 each exhibited high solubility of 2% by mass or greater in chloroform. Exemplary Compound A-9 dissolved to greater than 1% by mass in chloroform, but did not reach 2% by mass. Exemplary Compound A-34 exhibited lower solubility in chloroform.

Based on these results, it will be understood that the compounds of formula (I) of Exemplary Examples 1 to 7 had better solubility than the symmetric polyazo dye of Comparative Compound 1. Among them, those in which one from among R$^1$ and R$^2$ was a short-chain substituent and the other was a long-chain substituent exhibited even better solubility, and when the long-chain substituent was present on the polyoxyethylene chain, solubility was even further enhanced.

Embodiment 1

Next, the compounds synthesized in Synthesis Examples 1 to 6 were used to manufacture light absorption anisotropic films.

Specifically, one weight part of each of the compounds synthesized in Synthesis Examples 1 to 6 was separately added to 99 weight parts of chloroform. Following stirring and dissolution, a liquid-crystal composition coating liquid was obtained. Each of the coating liquids was then coated on an alignment film that had been formed on a glass substrate and had been rubbed. Subsequently, the chloroform was allowed to dry naturally at room temperature, yielding individual light absorption anisotropic films. The polyvinylalcohol indicated below was employed as the alignment film.

[Chem. 83]

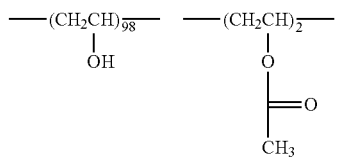

It proved impossible to prepare a coating liquid with a concentration of 1 weight part of Exemplary Compound A-34, synthesized in Synthesis Example 7, in 99 weight parts of chloroform. A film could not be formed under the same conditions.

The orientation order of each of the light absorption anisotropic films obtained was determined by measuring the following dichroic ratio.

<The Dichroic Ratio>

The dichroic ratio was calculated using the following equation after measuring the absorbance of the light absorption anisotropic film with a spectrophotometer with an iodine polarizing element disposed in the entering light optical system.

Dichroic ratio$(D)=A_z/A_y$

[Chem. 82]

Comparison Compound 1 (a symmetric polyazo dye)

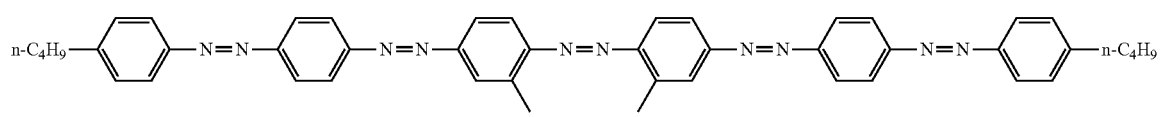

Az: Absorbance of polarized light in the direction of the absorption axis of the light absorption anisotropic film Ay: Absorbance of polarized light in the direction of the polarizing axis of the light absorption anisotropic film <The Orientation Order>

The orientation order was calculated from the dichroic ratio using the following equation.

Orientation order$(S)=(D-1)/(D+2)$

<Light Resistance>

While being heated from room temperature to 200° C., each of the light absorption anisotropic films that had been prepared was irradiated with 10 mW of light and the light resistance was determined based on the change in the intensity of absorption.

Comparative Example

With the exception that the compound was changed to Comparative Compound 2 below, a light absorption anisotropic film was prepared in the same manner as in the embodiment. The results of measurement of the orientation degree and light resistance of the light absorption anisotropic film obtained are given in Table 1.

Comparative Compound 2 was a compound described in above-cited Nonpatent Reference 5. It had nematic liquid crystallinity and good solubility, but poor light resistance. When irradiated with light while being heated, it was observed to fade rapidly.

An attempt was also made to prepare a light absorption anisotropic film using Comparative Compound 1, but Comparative Compound 1 had almost no solubility in chloroform, precluding preparation of a coating liquid.

[Chem. 84]

The results of measurement of the orientation order and light resistance of each of the light absorption anisotropic films obtained have been collected into Table 1 below. The phase transition temperatures are also given.

TABLE 1

| | Phase transition temperatures | | Order S | Light resistance |
|---|---|---|---|---|
| A-3 | K $\xrightarrow{138° C.}$ N $\underset{282° C.}{\xrightleftharpoons{284° C.}}$ I | | 0.94 | Good |
| A-4 | K $\xrightarrow{133° C.}$ N $\underset{293° C.}{\xrightleftharpoons{299° C.}}$ I | | 0.93 | Good |

TABLE 1-continued

| | Phase transition temperatures | | Order S | Light resistance |
|---|---|---|---|---|
| A-6 | K $\xrightarrow{113° C.}$ N $\underset{243° C.}{\xrightleftharpoons{275° C.}}$ I | | 0.95 | Good |
| A-7 | K $\xrightarrow{135° C.}$ N $\underset{270° C.}{\xrightleftharpoons{290° C.}}$ I | | 0.90 | Good |
| A-9 | K $\xrightarrow{148° C.}$ N $\underset{210° C.}{\xrightleftharpoons{212° C.}}$ I | | 0.72 | Good |
| A-10 | K $\xrightarrow{110° C.}$ N $\underset{201° C.}{\xrightleftharpoons{201° C.}}$ I | | 0.87 | Good |
| Comp. Comp 2 | K $\xrightarrow{265° C.}$ N $\underset{290° C.}{\xrightleftharpoons{290° C.}}$ I | | 0.90 | Poor |

Based on the above results, it will be understood that the compounds of formula (I) afforded high degrees of order and good light resistance.

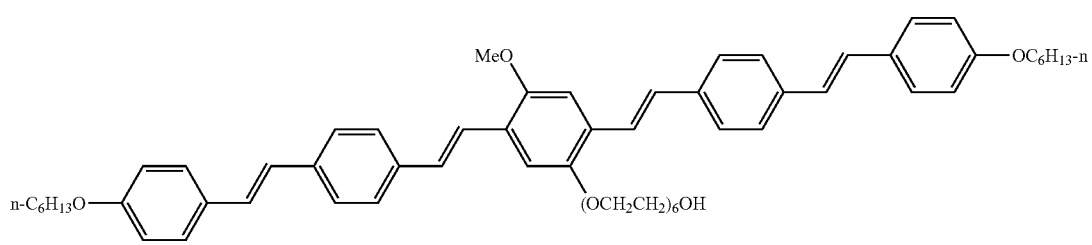

Comparative Compound 2

Additionally, Comparative Compound 2 exhibited poor light resistance. With an original absorption wavelength of 432.5 nm, it exhibited inadequate color generation as a dichroic dye.

Embodiment 2

To 99 weight parts of chloroform were added 0.2 part of Exemplary Compound A-3, 0.4 part of dye 1, and 0.4 part of dye 2 below. The mixture was stirred and dissolved, yielding a liquid-crystal composition coating liquid. Next, the coating liquid was coated on an alignment film that had been formed on a glass substrate and had been rubbed. Subsequently, the chloroform was allowed to dry naturally at room temperature. The same alignment film was employed as in Embodiment 1.

[Chem. 85]

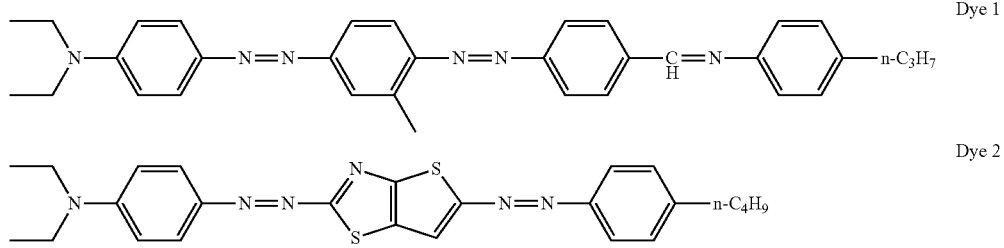

Dye 1

Dye 2

The order of the light absorption anisotropic film obtained was 0.92. The light transmittance in the xy chromaticity diagram when employing a C light source as light source was x=0.34 and y=0.29. Thus, the hue was adequate for use as a polarizing plate.

The invention claimed is:

1. The liquid-crystal compound denoted by general formula (I) below:

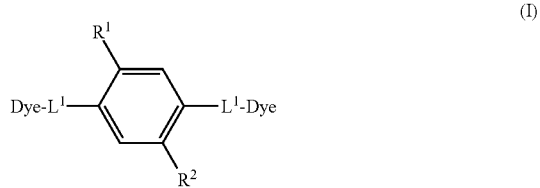

(I)

wherein each of $R^1$ and $R^2$ denotes a hydrogen atom, alkyl group, alkoxy group, or substituent denoted by -$L^2$-Y, with at least one of the two denoting a group other than a hydrogen atom, provided that at least one of $R^1$ and $R^2$ denotes a substituent denoted by -$L^2$-Y; $L^2$ denotes an alkylene group with 5 to 30 carbon atoms, in which one $CH_2$ group, or two or more nonadjacent $CH_2$ groups, are optionally substituted with —O—, —COO—, —OCO—, —OCOO—, —NRCOO—, —OCONR—, —CO—, —S—, —$SO_2$—, —NR—, —$NRSO_2$—, or —$SO_2NR$— (where R denotes a hydrogen atom or an alkyl group with 1 to 4 carbon atoms); Y denotes a hydrogen atom, hydroxy group, alkoxy group, carboxyl group, halogen atom, or polymerizable group; each instance of $L^1$ denotes a linking group selected from the group consisting of azo groups (—N=N—), carbonyloxy groups (—C(=O)O—), oxycarbonyl groups (—O—C(=O)—) imino groups (—N=CH—), and vinylene groups —CH=CH—; and each instance of Dye denotes an azo dye residue denoted by general formula (II):

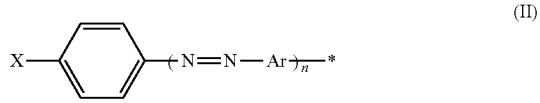

(II)

where in formula (II), * denotes a bond with $L^1$; X denotes a hydroxy group, a substituted or unsubstituted alkyl group, a substituted or unsubstituted alkoxy group, an unsubstituted amino group, or a mono or dialkylamine group; Ar denotes an optionally substituted aromatic hydrocarbon ring or optionally substituted aromatic hetero ring; and n denotes an integer of 1 to 3 such that when n is 2 or greater, the multiple instances of Ar may be identical or mutually different.

2. The liquid-crystal compound according to claim 1, wherein in formula (I), $R^1$ denotes a hydrogen atom, an alkyl group with 1 to 10 carbon atoms, or an alkoxy group with 1 to 9 carbon atoms; $R^2$ denotes a substituent denoted by -$L^2$-Y, wherein $L^2$ denotes an alkylene group with 5 to 30 carbon atoms, in which one $CH_2$ group, or two or more nonadjacent $CH_2$ groups, are optionally substituted with —O—, —COO—, —OCO—, —OCOO—, —CO—, —S—, —$SO_2$—, —NR—, —$NRSO_2$—, or —$SO_2NR$— (where R denotes a hydrogen atom or an alkyl group with 1 to 4 carbon atoms); and Y denotes a hydrogen atom, hydroxy group, alkoxy group, carboxyl group, halogen atom, or polymerizable group.

3. The liquid-crystal compound according to claim 1, wherein $L^1$ in general formula (I) is a vinylene group.

4. The liquid-crystal compound according to claim 1, wherein $L^2$ in general formula (I) comprises a group denoted by —$(OCH_2CH_2)_p$— (where p denotes a number of 3 or greater).

5. The liquid-crystal compound according to claim 1, wherein in formula (I), $R^1$ denotes a hydrogen atom, an alkyl group with 1 to 10 carbon atoms, or an alkoxy group with 1 to 9 carbon atoms; $R^2$ denotes a substituent denoted by -$L^2$-Y, wherein $L^2$ in general formula (I) comprises a group denoted by —$(OCH_2CH_2)_p$— (where p denotes a number of 3 or greater), and Y denotes a hydrogen atom, hydroxy group, alkoxy group, carboxyl group, halogen atom, or polymerizable group.

6. The liquid-crystal compound according to claim 1, wherein $L^1$ in general formula (I) is a vinylene group, and $L^2$ in general formula (I) comprises a group denoted by —$(OCH_2CH_2)_p$— (where p denotes a number of 3 or greater).

7. The liquid-crystal compound according to claim 1, wherein in formula (I), $R^1$ denotes a hydrogen atom, an alkyl group with 1 to 10 carbon atoms, or an alkoxy group with 1 to 9 carbon atoms; $R^2$ denotes a substituent denoted by -$L^2$-Y, wherein $L^2$ in general formula (I) comprises a group denoted by —$(OCH_2CH_2)_p$— (where p denotes a number of 3 or greater) and Y denotes a hydrogen atom, hydroxy group, alkoxy group, carboxyl group, halogen atom, or polymerizable group; and $L^1$ in general formula (I) is a vinylene group.

8. The liquid-crystal compound according to claim 1, wherein Y in general formula (I) is a polymerizable group.

9. The liquid-crystal compound according to claim 1, wherein in formula (I), $R^1$ denotes a hydrogen atom, an alkyl group with 1 to 10 carbon atoms, or an alkoxy group with 1 to 9 carbon atoms; $R^2$ denotes a substituent denoted by -$L^2$-Y, wherein $L^2$ denotes an alkylene group with 5 to 30 carbon atoms, in which one $CH_2$ group, or two or more nonadjacent $CH_2$ groups, are optionally substituted with —O—, —COO—, —OCO—, —OCOO—, —CO—, —S—, —$SO_2$—, —NR—, —$NRSO_2$—, or —$SO_2NR$— (where R denotes a hydrogen atom or an alkyl group with 1 to 4 carbon atoms), and Y in general formula (I) is a polymerizable group.

10. The liquid-crystal compound according to claim 1, wherein $L^1$ in general formula (I) is a vinylene group, and Y in general formula (I) is a polymerizable group.

11. The liquid-crystal compound according to claim 1, wherein $L^2$ in general formula (I) comprises a group denoted by —$(OCH_2CH_2)_p$— (where p denotes a number of 3 or greater), and Y in general formula (I) is a polymerizable group.

12. The liquid-crystal compound according to claim 1, wherein in formula (I), $R^1$ denotes a hydrogen atom, an alkyl group with 1 to 10 carbon atoms, or an alkoxy group with 1 to 9 carbon atoms; $R^2$ denotes a substituent denoted by -$L^2$-Y, wherein $L^2$ in general formula (I) comprises a group denoted by —$(OCH_2CH_2)_p$— (where p denotes a number of 3 or greater), and Y in general formula (I) is a polymerizable group.

13. The liquid-crystal compound according to claim 1, wherein $L^1$ in general formula (I) is a vinylene group, $L^2$ in general formula (I) comprises a group denoted by —$(OCH_2CH_2)_p$— (where p denotes a number of 3 or greater), and Y in general formula (I) is a polymerizable group.

14. The liquid-crystal compound according to claim 1, wherein in formula (I), $R^1$ denotes a hydrogen atom, an alkyl group with 1 to 10 carbon atoms, or an alkoxy group with 1 to 9 carbon atoms; $R^2$ denotes a substituent denoted by -$L^2$-Y, wherein $L^2$ in general formula (I) comprises a group denoted by —$(OCH_2CH_2)_p$— (where p denotes a number of 3 or greater), $L^1$ in general formula (I) is a vinylene group, and Y in general formula (I) is a polymerizable group.

15. A liquid-crystal composition comprising the liquid-crystal compound according to claim 1.

16. The liquid-crystal composition according to claim 15, further comprising one or more dichroic dyes.

17. A film comprising the liquid-crystal composition according to claim 15.

18. A light-absorbing anisotropic film comprising the liquid-crystal composition according to claim 15.

19. The light-absorbing anisotropic film according to claim 18, wherein the light that is transmitted when a C light source is employed as the light source satisfies 0.28<x<0.36 and 0.28<y<0.36 in the xy chromaticity diagram.

20. A liquid-crystal display device comprising the light-absorbing anisotropic film according to claim 18.

* * * * *